US007115139B2

United States Patent
McClurken et al.

(10) Patent No.: US 7,115,139 B2
(45) Date of Patent: Oct. 3, 2006

(54) FLUID-ASSISTED MEDICAL DEVICES, FLUID DELIVERY SYSTEMS AND CONTROLLERS FOR SUCH DEVICES, AND METHODS

(75) Inventors: Michael E. McClurken, Durham, NH (US); Robert Luzzi, Exeter, NH (US); Arnold E. Oyola, Raymond, NH (US); Mark T. Charbonneau, Reading, MA (US)

(73) Assignee: Tissuelink Medical Inc., Dover, NH (US)

( * ) Notice: Subject to any disclaimer, the term of this patent is extended or adjusted under 35 U.S.C. 154(b) by 65 days.

(21) Appl. No.: 09/947,658

(22) Filed: Sep. 5, 2001

(65) Prior Publication Data

US 2002/0062123 A1 May 23, 2002

Related U.S. Application Data

(63) Continuation-in-part of application No. 09/797,049, filed on Mar. 1, 2001, now Pat. No. 6,702,810.

(60) Provisional application No. 60/187,114, filed on Mar. 6, 2000.

(51) Int. Cl.
*A61F 7/00* (2006.01)
(52) U.S. Cl. .................. 607/96; 607/104; 128/898
(58) Field of Classification Search .................. 606/32, 606/39–42, 45–50; 607/99, 101, 102, 104, 607/105, 106, 113, 96; 128/898
See application file for complete search history.

(56) References Cited

U.S. PATENT DOCUMENTS

| 623,022 A | 4/1899 | Johnson |
| 2,002,594 A | 5/1935 | Wappler et al. |
| 3,163,166 A | 12/1964 | Brant et al. |
| 3,901,241 A | 8/1975 | Allen, Jr. |
| 4,037,590 A | 7/1977 | Dohring et al. |
| 4,307,720 A | 12/1981 | Weber, Jr. |
| 4,326,529 A | 4/1982 | Doss et al. |
| 4,567,890 A | 2/1986 | Ohta et al. |

(Continued)

FOREIGN PATENT DOCUMENTS

EP 0895756 2/1999

(Continued)

OTHER PUBLICATIONS

U.S. Appl. No. 09/347,635, "Apparatus and Method for Creating, Maintaining, and Controlling a Virtual Electrode Used for the Ablation of Tissue", Hoey et al., filed Jul. 6, 1999.

(Continued)

*Primary Examiner*—Rosiland Rollins
(74) *Attorney, Agent, or Firm*—Merchant & Gould P.C.

(57) ABSTRACT

Medical devices, methods and systems for treating tissue are provided. An exemplary system comprises a fluid from a fluid source, a surgical device which provides energy and the fluid to the tissue and a control mechanism which changes a flow rate of fluid provided from the surgical device and changes a rate of energy provided from the surgical device. The fluid flow rate changes between at least two non-zero flow rates and the energy rate changes between at least two non-zero energy rates. An exemplary method comprises providing a fluid from a fluid source, providing a surgical device which provides energy and the fluid to the tissue, and changing a flow rate of fluid provided from the surgical device with a change in a rate of energy provided from the surgical device. Exemplary devices comprise a tip portion configured to provide energy and a fluid to a tissue.

45 Claims, 24 Drawing Sheets

U.S. PATENT DOCUMENTS

| | | | |
|---|---|---|---|
| 4,602,628 A | 7/1986 | Allen, Jr. | |
| 4,674,499 A | 6/1987 | Pao | |
| 4,920,982 A | 5/1990 | Goldstein | |
| 4,985,030 A | 1/1991 | Melzer et al. | |
| 5,009,656 A | 4/1991 | Reimels | |
| 5,035,696 A | 7/1991 | Rydell | |
| 5,071,419 A | 12/1991 | Rydell et al. | |
| 5,122,138 A | 6/1992 | Manwaring | |
| 5,151,102 A | 9/1992 | Kamiyama et al. | |
| 5,156,613 A | 10/1992 | Sawyer | |
| 5,167,659 A | 12/1992 | Ohtomo et al. | |
| 5,190,541 A | 3/1993 | Abele et al. | |
| 5,217,460 A | 6/1993 | Knoepfler | |
| 5,242,441 A | 9/1993 | Avitall | |
| 5,242,442 A | 9/1993 | Hirschfeld | |
| 5,269,781 A | 12/1993 | Hewell, III | |
| 5,277,696 A | 1/1994 | Hagen | |
| 5,282,799 A | 2/1994 | Rydell | |
| 5,300,087 A | 4/1994 | Knoepfler | |
| 5,313,943 A | 5/1994 | Houser et al. | |
| 5,318,589 A | 6/1994 | Lichtman | |
| 5,322,503 A | 6/1994 | Desai | |
| 5,334,193 A | 8/1994 | Nardella | |
| 5,342,357 A | 8/1994 | Nardella | |
| 5,348,554 A * | 9/1994 | Imran et al. | 606/41 |
| 5,364,394 A | 11/1994 | Mehl | |
| 5,395,312 A | 3/1995 | Desai | |
| 5,395,363 A | 3/1995 | Billings et al. | |
| 5,401,272 A | 3/1995 | Perkins | |
| 5,403,311 A | 4/1995 | Abele et al. | |
| 5,403,312 A | 4/1995 | Yates et al. | |
| 5,405,376 A | 4/1995 | Mulier et al. | |
| 5,431,649 A | 7/1995 | Mulier et al. | |
| 5,433,708 A | 7/1995 | Nichols et al. | |
| 5,437,664 A | 8/1995 | Cohen et al. | |
| 5,456,682 A | 10/1995 | Edwards et al. | |
| 5,458,596 A | 10/1995 | Lax et al. | |
| 5,458,597 A | 10/1995 | Edwards et al. | |
| 5,458,598 A | 10/1995 | Feinberg et al. | |
| 5,462,521 A | 10/1995 | Brucker et al. | |
| 5,472,441 A | 12/1995 | Edwards et al. | |
| 5,487,385 A | 1/1996 | Avitall | |
| 5,514,130 A | 5/1996 | Baker | |
| 5,536,267 A | 7/1996 | Edwards et al. | |
| 5,542,928 A | 8/1996 | Evans et al. | |
| 5,558,671 A | 9/1996 | Yates | |
| 5,562,703 A | 10/1996 | Desai | |
| 5,564,440 A | 10/1996 | Swartz et al. | |
| 5,569,242 A | 10/1996 | Lax et al. | |
| 5,575,810 A | 11/1996 | Swanson et al. | |
| 5,584,872 A | 12/1996 | LaFontaine et al. | |
| 5,605,539 A | 2/1997 | Buelna et al. | |
| 5,609,151 A | 3/1997 | Mulier et al. | |
| 5,637,110 A | 6/1997 | Pennybacker et al. | |
| 5,640,955 A | 6/1997 | Ockuly et al. | |
| 5,643,197 A | 7/1997 | Brucker et al. | |
| 5,647,871 A | 7/1997 | Levine et al. | |
| 5,653,692 A | 8/1997 | Masterson et al. | |
| 5,660,836 A | 8/1997 | Knowlton | |
| 5,676,662 A | 10/1997 | Fleischhacker et al. | |
| 5,676,693 A | 10/1997 | LaFontaine | |
| 5,681,282 A | 10/1997 | Eggers et al. | |
| 5,683,366 A | 11/1997 | Eggers et al. | |
| 5,683,384 A | 11/1997 | Gough et al. | |
| 5,687,723 A | 11/1997 | Avitall | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,697,927 A | 12/1997 | Imran et al. | |
| 5,713,896 A | 2/1998 | Nardella | |
| 5,718,241 A | 2/1998 | Ben-Haim et al. | |
| 5,718,701 A | 2/1998 | Shai et al. | |
| 5,722,400 A | 3/1998 | Ockuly et al. | |
| 5,725,524 A | 3/1998 | Mulier et al. | |
| 5,730,127 A | 3/1998 | Avitall | |
| 5,735,846 A | 4/1998 | Panescu et al. | |
| 5,746,739 A | 5/1998 | Sutter | |
| 5,749,869 A | 5/1998 | Lindenmeier et al. | |
| 5,755,753 A | 5/1998 | Knowlton | |
| 5,766,153 A | 6/1998 | Eggers et al. | |
| 5,797,960 A | 8/1998 | Stevens et al. | |
| 5,800,413 A | 9/1998 | Swartz et al. | |
| 5,800,482 A | 9/1998 | Pomeranz et al. | |
| 5,807,395 A | 9/1998 | Mulier et al. | |
| 5,810,764 A | 9/1998 | Eggers et al. | |
| 5,823,956 A | 10/1998 | Roth et al. | |
| 5,827,271 A | 10/1998 | Buysse et al. | |
| 5,833,703 A | 11/1998 | Manushakian | |
| 5,843,019 A | 12/1998 | Eggers et al. | |
| 5,843,078 A | 12/1998 | Sharkey | |
| 5,843,152 A | 12/1998 | Tu et al. | |
| 5,855,614 A | 1/1999 | Stevens et al. | |
| 5,860,951 A | 1/1999 | Eggers et al. | |
| 5,860,974 A | 1/1999 | Abele | |
| 5,861,002 A | 1/1999 | Desai | |
| 5,868,739 A | 2/1999 | Lindenmeier et al. | |
| 5,871,469 A | 2/1999 | Eggers et al. | |
| 5,873,855 A | 2/1999 | Eggers et al. | |
| 5,876,398 A | 3/1999 | Mulier et al. | |
| 5,888,198 A | 3/1999 | Eggers et al. | |
| 5,891,095 A | 4/1999 | Eggers et al. | |
| 5,895,417 A | 4/1999 | Pomeranz et al. | |
| 5,897,553 A | 4/1999 | Mulier et al. | |
| 5,902,272 A | 5/1999 | Eggers et al. | |
| 5,902,328 A | 5/1999 | LaFontaine et al. | |
| 5,906,613 A | 5/1999 | Mulier et al. | |
| 5,913,854 A | 6/1999 | Maguire et al. | |
| 5,913,856 A | 6/1999 | Chia et al. | |
| 5,954,716 A | 9/1999 | Sharkey et al. | |
| 5,964,755 A | 10/1999 | Edwards | |
| 5,976,128 A | 11/1999 | Schilling et al. | |
| 5,980,516 A | 11/1999 | Mulier et al. | |
| 5,992,418 A | 11/1999 | de la Rama et al. | |
| 6,015,407 A | 1/2000 | Rieb et al. | |
| 6,016,809 A | 1/2000 | Mulier et al. | |
| 6,017,338 A | 1/2000 | Brucker et al. | |
| 6,024,733 A | 2/2000 | Eggers et al. | |
| 6,027,501 A | 2/2000 | Goble et al. | |
| 6,030,379 A | 2/2000 | Panescu et al. | |
| 6,032,077 A | 2/2000 | Pomeranz | |
| 6,032,674 A | 3/2000 | Eggers et al. | |
| 6,045,532 A | 4/2000 | Eggers et al. | |
| 6,047,700 A | 4/2000 | Eggers et al. | |
| 6,053,172 A | 4/2000 | Hovda et al. | |
| 6,053,912 A | 4/2000 | Panescu et al. | |
| 6,056,745 A | 5/2000 | Panescu et al. | |
| 6,056,747 A | 5/2000 | Saadat et al. | |
| 6,063,079 A | 5/2000 | Hovda et al. | |
| 6,063,081 A | 5/2000 | Mulier et al. | |
| 6,066,134 A | 5/2000 | Eggers et al. | |
| 6,071,280 A | 6/2000 | Edwards et al. | |
| 6,080,151 A | 6/2000 | Swartz et al. | |
| 6,086,585 A | 7/2000 | Hovda et al. | |
| 6,093,186 A | 7/2000 | Goble | |
| 6,096,037 A | 8/2000 | Mulier et al. | |
| 6,102,046 A | 8/2000 | Weinstein et al. | |
| 6,105,581 A | 8/2000 | Eggers et al. | |
| 6,109,268 A | 8/2000 | Thapliyal et al. | |
| 6,113,597 A | 9/2000 | Eggers et al. | |
| 6,117,109 A | 9/2000 | Eggers et al. | |
| 6,135,999 A | 10/2000 | Fanton et al. | |
| 6,142,992 A | 11/2000 | Cheng et al. | |
| 6,149,620 A | 11/2000 | Baker et al. | |

| Patent Number | Date | Inventor(s) |
|---|---|---|
| 6,159,194 A | 12/2000 | Eggers et al. |
| 6,159,208 A | 12/2000 | Hovda et al. |
| 6,168,594 B1 | 1/2001 | LaFontaine et al. |
| 6,171,275 B1 | 1/2001 | Webster, Jr. |
| 6,174,308 B1 | 1/2001 | Goble et al. |
| 6,174,309 B1 | 1/2001 | Wrublewski et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,210,411 B1 | 4/2001 | Hofmann et al. |
| 6,216,704 B1 | 4/2001 | Ingle et al. |
| 6,217,576 B1 | 4/2001 | Tu et al. |
| 6,221,039 B1 | 4/2001 | Durgin et al. |
| 6,224,592 B1 | 5/2001 | Eggers et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,254,600 B1 | 7/2001 | Willink et al. |
| 6,258,086 B1 | 7/2001 | Ashley et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,302,903 B1 | 10/2001 | Mulier et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,315,777 B1 | 11/2001 | Comben |
| 6,322,549 B1 | 11/2001 | Eggers et al. |
| 6,327,505 B1 | 12/2001 | Medhkour et al. |
| 6,328,735 B1 * | 12/2001 | Curley et al. ............... 606/41 |
| 6,328,736 B1 | 12/2001 | Mulier et al. |
| 6,336,926 B1 | 1/2002 | Goble |
| 6,350,276 B1 | 2/2002 | Knowlton |
| 6,355,032 B1 | 3/2002 | Hovda et al. |
| 6,358,248 B1 | 3/2002 | Mulier et al. |
| 6,363,937 B1 | 4/2002 | Hovda et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,402,742 B1 | 6/2002 | Blewett et al. |
| 6,409,722 B1 * | 6/2002 | Hoey et al. ............... 606/34 |
| 6,409,723 B1 | 6/2002 | Edwards |
| 6,416,507 B1 | 7/2002 | Eggers et al. |
| 6,416,508 B1 | 7/2002 | Eggers et al. |
| 6,416,509 B1 * | 7/2002 | Goble et al. ............... 606/37 |
| 6,425,877 B1 | 7/2002 | Edwards |
| 6,432,103 B1 | 8/2002 | Ellsberry et al. |
| 6,458,123 B1 | 10/2002 | Brucker et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B1 | 10/2002 | Hovda et al. |
| 6,468,270 B1 | 10/2002 | Hovda et al. |
| 6,468,274 B1 | 10/2002 | Alleyne et al. |
| 6,493,589 B1 | 12/2002 | Medhkour et al. |
| 6,558,385 B1 | 5/2003 | McClurken et al. |
| 2001/0020167 A1 | 9/2001 | Woloszko et al. |
| 2001/0032002 A1 | 10/2001 | McClurken et al. |
| 2001/0039419 A1 | 11/2001 | Francischelli et al. |
| 2001/0051802 A1 | 12/2001 | Woloszko et al. |
| 2002/0002393 A1 | 1/2002 | Mitchell |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel |
| 2003/0004510 A1 | 1/2003 | Wham et al. |
| 2003/0114850 A1 | 6/2003 | McClurken et al. |
| 2004/0024395 A1 | 2/2004 | Ellman et al. |

FOREIGN PATENT DOCUMENTS

| | | |
|---|---|---|
| EP | 1 095 627 A1 | 5/2001 |
| EP | 1 157 666 A1 | 11/2001 |
| EP | 1 181 896 A1 | 2/2002 |
| JP | 57-117843 | 7/1982 |
| WO | WO 90/03152 A1 | 4/1990 |
| WO | WO 94/02077 A2 | 2/1994 |
| WO | WO 94/26228 A1 | 11/1994 |
| WO | WO 95/05781 A1 | 3/1995 |
| WO | WO 95/09570 A1 | 4/1995 |
| WO | WO 95/17222 A1 | 6/1995 |
| WO | WO 9634571 | 11/1996 |
| WO | WO 97/05829 A1 | 2/1997 |
| WO | WO 97/16127 A1 | 5/1997 |
| WO | WO 98/14131 A1 | 4/1998 |
| WO | WO 99/03414 A1 | 1/1999 |
| WO | WO 99/20213 A1 | 4/1999 |
| WO | WO 99/58070 A2 | 11/1999 |
| WO | WO 01/26570 A1 | 4/2001 |
| WO | WO 01/28444 A1 | 4/2001 |
| WO | WO 01/35845 A1 | 5/2001 |
| WO | WO 01/60273 A1 | 8/2001 |
| WO | WO 01/66026 A2 | 9/2001 |
| WO | WO 01/70114 A1 | 9/2001 |
| WO | WO 01/80757 A2 | 11/2001 |
| WO | WO 01/82812 A1 | 11/2001 |
| WO | WO 02/11635 A1 | 2/2002 |
| WO | WO 02/24089 A1 | 3/2002 |
| WO | WO 02/069821 A1 | 9/2002 |
| WO | WO 02/071966 A1 | 9/2002 |

OTHER PUBLICATIONS

TissueLink Medical, Inc. Floating Ball device brochure #71-100001-001 Rev A, 4 pages.
TissueLink Medical, Inc. Floating Ball device brochure #71-100001-001 Rev B, 4 pages.
TissueLink Medical, Inc. Floating Ball device brochure #71-100001-001 Rev C, 4 pages.

Beer, Edwin, "Removal of Neoplasms of the Urinary Bladder", JAMA., Sep. 9, 1983; 250(10): pp. 1324-1325.

Carter, James, "Suture? Staple? Electrosugery? How to Decide What is Best For You", JSLS., Apr.-Jun. 1997; 1(2): pp. 171-174.

Matek et al., "Modified Electrocoagulation and Its Possibilities in the Control of Gastrointestinal Bleeding", Endoscopy., Nov. 1979; 11(4): pp. 253-258.

Mittleman et al., "Use of the Saline Infusion Electrode Catheter for Improved Energy Delivery and Increased Lesion Size in Radiofrequency Catheter Ablation", PACE., May 1995;18(5 Pt 1): pp. 1022-1027.

Sakatani et al., "Isotonic Mannitol and the Prevention of Local Heat Generation and Tissue Adherence to Bipolar Diathermy Forceps Tips during Electrical Coagulation", J. Neurosurg., Apr. 1995; 82(4): pp. 669-671.

Takao, T., "Effect of Cautery with Irrigation Forceps on the Remnant Liver after Hepatectomy in Rats", Eur. Surg. Res., 1999; 31(2): pp. 173-179.

Yasargil, M.G., "Microsurgery Applied to Neurosurgery", New York: Academic Press, 1969, pp. 41-45.

Yamamoto et al., "New Simple Technique for Hepatic Parenchymal Resection Using a Cavitron Ultrasonic Surgical Aspirator and Bipolar Cautery Equipped with a Channel for Water Dripping", World. J. Surg., Oct. 1999; 23(10): pp. 1032-1037.

\* cited by examiner

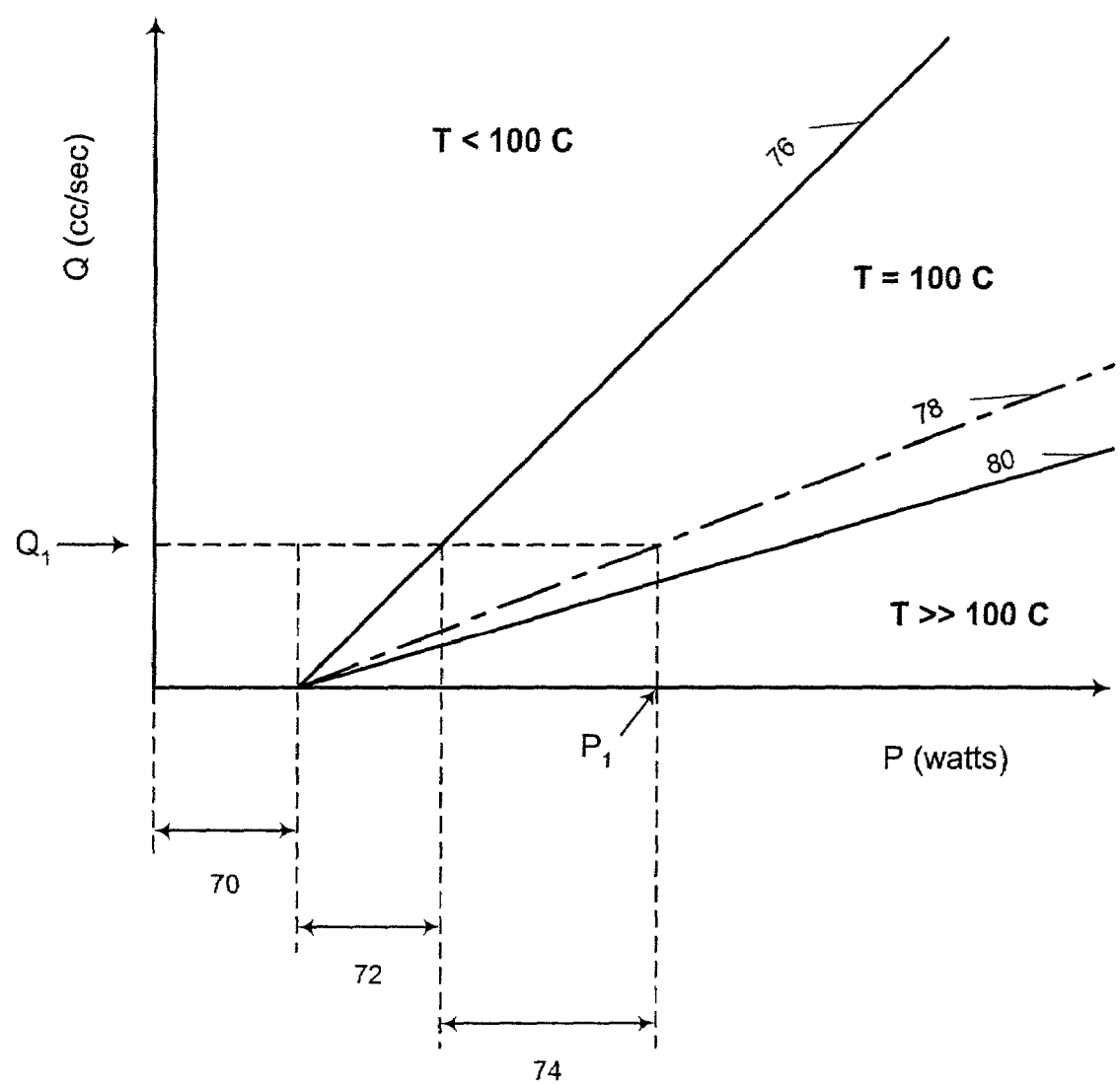

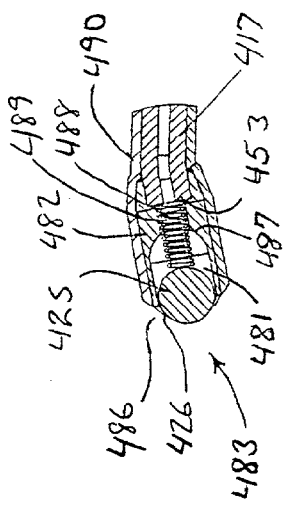
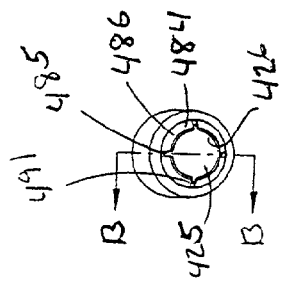
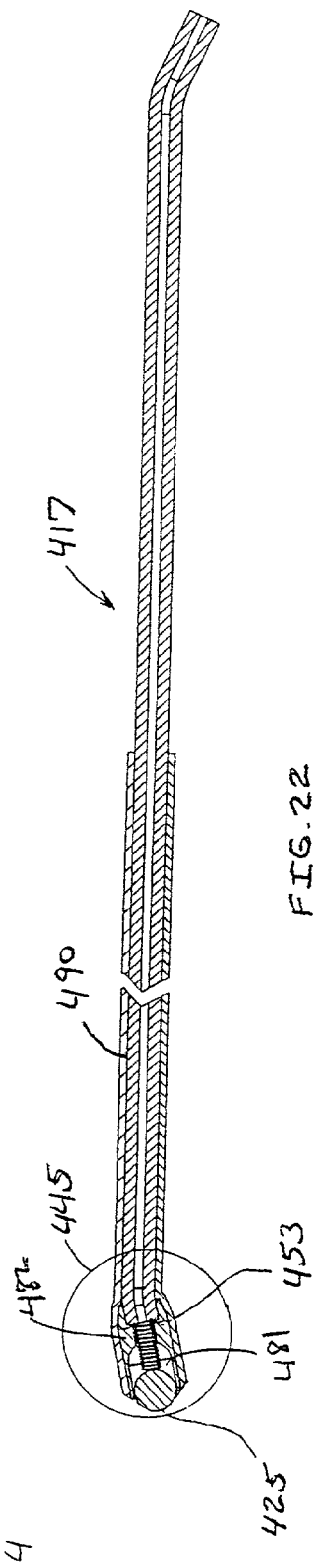

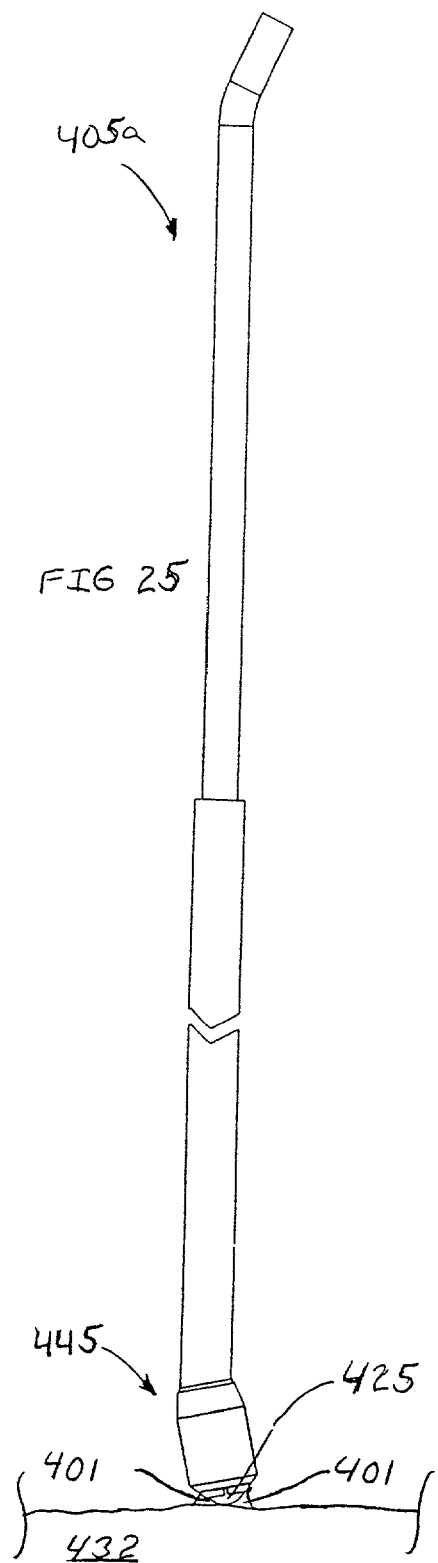

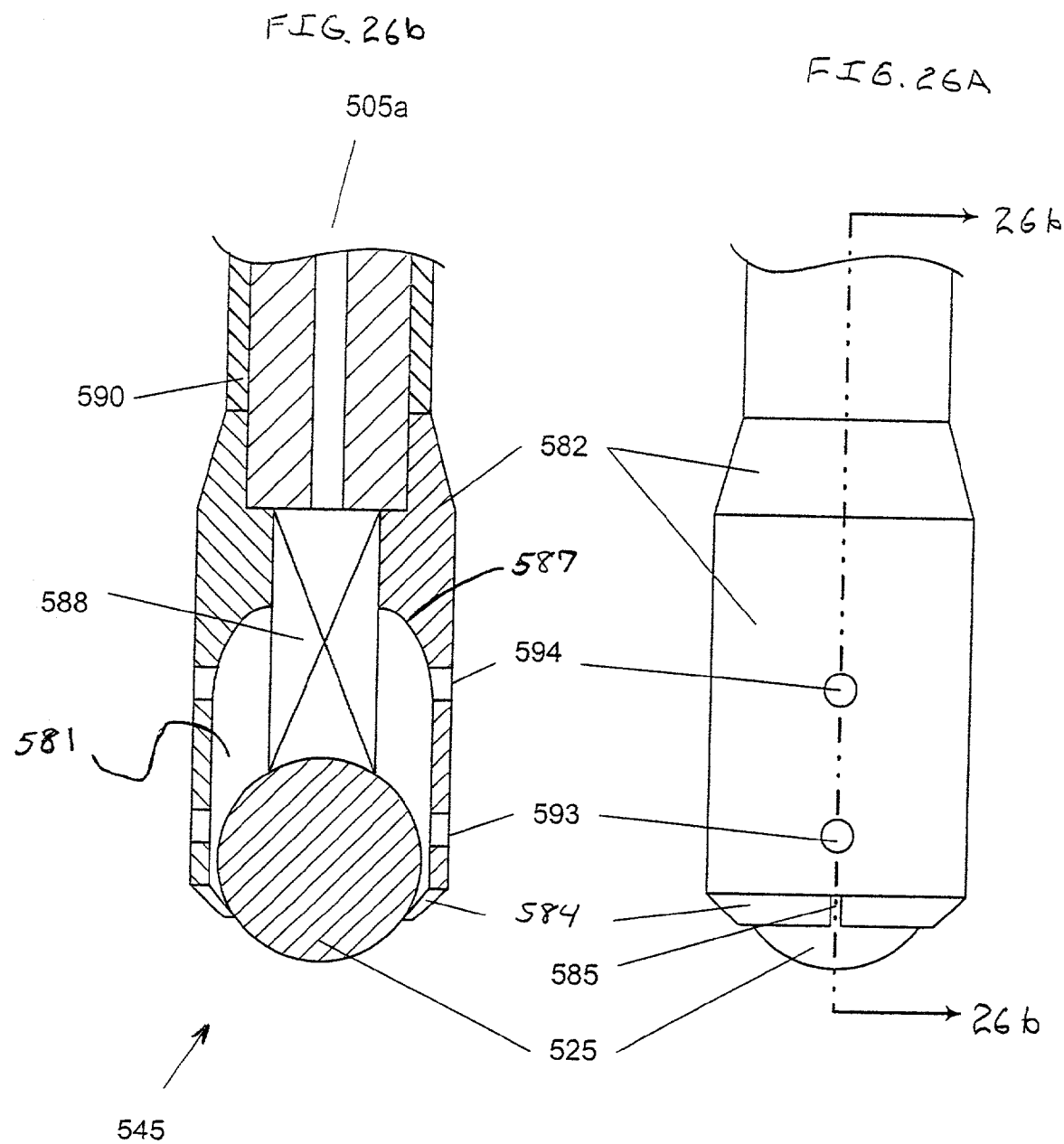

FLUID-ASSISTED MEDICAL DEVICES, FLUID DELIVERY SYSTEMS AND CONTROLLERS FOR SUCH DEVICES, AND METHODS

CROSS REFERENCE TO RELATED APPLICATIONS

This patent is a continuation-in-part of and application claims the benefit of priority of U.S. patent application Ser. No. 09/797,049, filed Mar. 1, 2001, now U.S. Pat. No. 6,702,810, the entire disclosure of which is incorporated by reference, which is a continuation of U.S. patent application Ser. No. 60/187,114, filed Mar. 6, 2000. This patent application also claims the benefit of priority of U.S. patent application Ser. No. 60/187,114, filed Mar. 6, 2000, the entire disclosure of which is incorporated herein by reference.

FIELD OF THE INVENTION

This invention relates generally to the field of medical devices, methods and systems for use upon a body during surgery. More particularly, the invention relates to electrosurgical devices, methods and systems for use upon tissues of a human body during surgery.

BACKGROUND

Electrosurgical devices use electrical energy, most commonly radio frequency (RF) energy, to cut tissue or to cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to stop the bleeding from severed blood vessels.

Current electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 320° C., and such high temperatures can be transmitted to adjacent tissue via thermal diffusion. Undesirable results of such transmission to adjacent tissue include unintended thermal damage to the tissue.

Using saline to couple RF electrical energy to tissue inhibits such undesirable effects as sticking, desiccation, smoke production and char formation. One key factor is inhibiting tissue desiccation, which occurs if tissue temperature exceeds 100° C. and all of the intracellular water boils away, leaving the tissue extremely dry and much less electrically conductive. However, an uncontrolled flow rate of saline can provide too much cooling at the electrode/tissue interface. This cooling reduces the temperature of the target tissue being treated, and the rate at which tissue thermal coagulation occurs is determined by tissue temperature. This, in turn, can result in longer treatment time, to achieve the desired tissue temperature for cauterization or cutting of the tissue. Long treatment times are undesirable for surgeons since it is in the best interest of the patient, physician and hospital to perform surgical procedures as quickly as possible.

RF energy delivered to tissue is unpredictable and often not optimal when using general-purpose generators. Most general-purpose RF generators have modes for different waveforms (cut, coagulation, or a blend of these two) and device types (monopolar, bipolar), as well as power levels that can be set in watts. However, once these settings are chosen, the actual power delivered to tissue can vary dramatically over time as tissue impedance changes over the course of RF treatment. This is because the power delivered by most generators is a function of tissue impedance, with the power ramping down as impedance either decreases toward zero or increases significantly to several thousand ohms.

A further limitation of current electrosurgical devices arises from size constraints of the device in comparison to tissue that is encountered during a single surgical procedure. During the course of a single procedure, for example, a surgeon often encounters a wide variety of tissue sizes. Surgical devices often come in a variety of sizes because larger segments of tissue physically require commensurately larger electrode jaws or tips, but smaller segments of tissue often are not optimally treated by the much larger size RF device. It is undesirable to require numerous surgical devices during a single procedure, because this wastes valuable operating room time, can make it difficult to precisely relocate the treatment site, increases the risk of infection, and increases the cost by increasing the number of different surgical devices that are needed to complete the surgical procedure.

For example, a bipolar saline-enhanced tissue sealing forceps that has jaws long enough to effectively seal a 30 mm length of tissue may not be desirable for sealing a segment of tissue that is 10 mm in length. Excess saline from one of the electrode jaws (for a bipolar device) can flow to the other electrode in the space where there is no intervening tissue. This flow of electrically conductive saline can act as an electrical resistor in parallel with the electrical pathway through the target tissue. Electrical current flow through the saline can divert or shunt RF energy away from going through the target tissue, and slow down the rate at which the target tissue is heated and treated.

A surgeon may first be sealing and cutting lung tissue as part of a wedge resection using the full 30 mm jaw length 2–3 times to remove a tip of a lobe of lung for biopsy. If the intraoperative histopathology indicates that the suspected tissue has a malignant tumor, then the surgeon may convert the procedure to a lobectomy. As part of the lobectomy the surgeon will want to seal and cut large blood vessels that supply the lobe. Alternatively, the surgeon may want to toughen up or coagulate large vessels with RF and then apply a ligating clip to assure hemostasis before cutting. Even compressed, these blood vessels might only fill a small fraction of the 30 mm length of electrode jaw. For at least the reasons identified above, this is an undesirable situation with current electrosurgical devices.

SUMMARY OF THE INVENTION

The invention provides a system for treating tissue comprising a power measurement device, a flow rate controller coupled to the power measurement device, and an electrosurgical device configured and arranged to provide radio frequency power and conductive fluid to the tissue, wherein the flow rate controller is configured and arranged to modify a flow rate of the conductive fluid to the tissue, based on signals from the power measurement device.

Preferably, the flow rate controller modifies the flow rate of the conductive fluid to the tissue based on heat used to warm the conductive fluid and heat used to convert the conductive fluid to vapor. In a preferred embodiment, the flow rate controller modifies the flow rate of the conductive fluid to the tissue using the relationship:

$$Q = K \times P$$

where the flow rate Q is proportional to the power P, and where the proportionality constant K is given by:

$$K = \frac{1}{\{\rho c_p \Delta T + \rho h_v Q_b / Q_l\}}$$

In another embodiment, the invention provides a device for modifying flow rate of conductive fluid to tissue based on measurement of radio frequency power delivered to the tissue. The device comprises a flow rate controller configured and arranged to modify flow rate of the conductive fluid to the tissue, based on heat used to warm the conductive fluid and heat used to convert the conductive fluid to vapor. Preferably, the device modifies the flow rate of the conductive fluid to the tissue using the relationship:

$$K = \frac{1}{\{\rho c_p \Delta T + \rho h_v Q_b / Q_l\}}$$

In an alternative embodiment, the invention provides a device for treating tissue using radio frequency power and conductive fluid. The device comprises a sensing device, and a processor coupled to the sensing device, wherein the processor is configured and arranged to adjust the flow rate of the conductive fluid to the tissue, by determining a level of radio frequency power applied to the tissue using the sensing device, and adjusting the flow rate of the conductive fluid to the tissue. Preferably, the processor is configured and arranged to adjust the flow rate of the conductive fluid to the tissue based on heat used to warm the conductive fluid and heat used to convert the conductive fluid to vapor. Preferably, the flow rate controller modifies the flow rate of the conductive fluid to the tissue using the relationship:

$$K = \frac{1}{\{\rho c_p \Delta T + \rho h_v Q_b / Q_l\}}$$

In another embodiment, the invention provides a method for treating tissue comprising applying radio frequency power and conductive fluid to the tissue using a surgical device, wherein the conductive fluid is provided to the tissue at a fluid flow rate, determining an amount of radio frequency power applied to the tissue, and modifying the fluid flow rate based on the power applied to the tissue. Preferably, the step of modifying the fluid flow rate based on the power applied to the tissue comprises modifying the flow rate of the conductive fluid to the tissue based on heat used to warm the conductive fluid and heat used to convert the conductive fluid to vapor. Preferably, the step of modifying the fluid flow rate based on the power applied to the tissue comprises determining the fluid flow rate using the relationship:

$$K = \frac{1}{\{\rho c_p \Delta T + \rho h_v Q_b / Q_l\}}$$

In an alternative embodiment, the invention provides a method for treating tissue comprising providing a surgical device comprising an electrode, wherein the surgical device is configured and arranged to receive radio frequency power and conductive fluid and deliver the radio frequency power and conductive fluid to the tissue, determining the radio frequency power applied to the tissue, and providing the conductive fluid to the tissue at a fluid flow rate, wherein the fluid flow rate is modified to control boiling of the conductive fluid at the tissue. Preferably, the step of providing the conductive fluid to the tissue at a fluid flow rate comprises providing the conductive fluid to the tissue based on heat used to warm the conductive fluid and heat used to convert the conductive fluid to vapor. In a preferred embodiment, the step of providing the conductive fluid to the tissue at a fluid flow rate comprises providing the conductive fluid to the tissue using the relationship:

$$K = \frac{1}{\{\rho c_p \Delta T + \rho h_v Q_b / Q_l\}}$$

In another embodiment, the invention provides a system for treating tissue comprising a power measurement device, a flow rate controller coupled to the power measurement device, a flow control device coupled to the flow rate controller, and an electrosurgical device coupled to the flow control device and the power measurement device, wherein the electrosurgical device is configured and arranged to provide radio frequency power and conductive fluid to the tissue, and wherein the flow rate controller is configured and arranged to modify a flow rate of the conductive fluid to the electrosurgical device, based on signals from the power measurement device. Preferably, the flow control device comprises a pump. In one embodiment, the pump comprises a peristaltic pump. In another embodiment, the pump comprises a syringe pump. Preferably, the electrosurgical device comprises a bipolar electrosurgical device.

According to this embodiment, the flow rate controller is preferably configured and arranged to modify the flow rate of the conductive fluid to the flow control device based on heat used to warm the conductive fluid and heat used to convert the conductive fluid to vapor. In a preferred embodiment, the flow rate controller is configured and arranged to modify the flow rate of the conductive fluid to the tissue using the relationship:

$$K = \frac{1}{\{\rho c_p \Delta T + \rho h_v Q_b / Q_l\}}$$

The invention can improve the speed of tissue coagulation provided by fluid-enhanced electrosurgery by assuring that the electrode-tissue interface is within a desired temperature range (for example, not significantly hotter than 100° C.) through the control of the fraction of conductive fluid that is boiled off at the electrode-tissue interface. This improvement can be achieved by measuring power provided to the device and regulating the flow of fluid to the device. Preferably, tissue sensors (for example, that would measure tissue temperature or tissue impedance) are not required according to the invention.

Some embodiments of the invention can provide one or more advantages, such as the ability to achieve the desired tissue effect (for example, coagulation, cutting, or the like) in a fast, effective manner. The invention can also provide the ability to treat tissue quickly without using a tissue sensor (for example, a temperature sensor) built into the device or a custom special-purpose generator. The invention can allow a surgeon to use a variety of electrosurgical devices with a wide variety of general-purpose generators. Further, the invention can provide the ability to use an electrosurgical device that is capable of quickly and effectively sealing a wide variety of tissue sizes and thicknesses.

In certain applications, a system for treating tissue is provided. The system comprises energy from energy source, a fluid from a fluid source, a surgical device which provides the energy and the fluid to the tissue and a fluid flow control mechanism which changes a flow rate of fluid provided from the surgical device with a change in a rate of energy provided from the surgical device. The flow rate of fluid changes between at least two non-zero flow rates, and the rate of energy changes between at least two non-zero rates of energy.

In some applications, the fluid flow control mechanism increases or decreases the flow rate of fluid with an increase or decrease in the rate of energy provided from the surgical device, respectively. Additionally or alternatively, the fluid flow control mechanism can increase or decrease the fluid flow rate linearly with an increase or decrease in the rate of energy provided from the surgical device, respectively.

In some applications, the energy provided from the surgical device leads to a heating of at least a portion of the fluid provided from the surgical device and the heating of the fluid results in a property change of at least a portion of the fluid. In some instances, the property change of the fluid comprises a color change due to dye present in the fluid, or a phase change from a liquid phase to a vapor phase. Additionally or alternatively, heating of the fluid results in vaporization of at least a portion of the fluid.

The energy provided from the surgical device generally leads to a heating of the tissue, and vaporization of the fluid provides a temperature control mechanism for the heating of the tissue. According to another aspect of the invention, the temperature control mechanism comprises the heat of vaporization of the fluid.

In some applications of the techniques described herein, the fluid flow control mechanism increases the flow rate of fluid provided from the surgical device with an increase in a boiling percentage of the fluid provided from the surgical device. Alternately or additionally, the fluid flow control mechanism decreases the flow rate of fluid with a decrease in the boiling percentage of the fluid.

In some systems, a fluid flow rate controller and energy source output measurement device are provided, with the fluid flow rate controller providing an output signal to change the flow rate of fluid provided from the surgical device as a result of a change in an input signal that is received from the energy source output measurement device signifying a change in the rate of energy provided from the surgical device.

In some applications, the energy source comprises an electrical generator and the energy comprises alternating current electrical energy. Furthermore, the alternating current electrical energy has a frequency, which is within a frequency band, the frequency band being about 9 kilohertz to 300 gigahertz.

In some systems, the fluid source comprises the fluid within an intravenous bag and the fluid comprises an electrically conductive fluid. The electrically conductive fluid can comprise saline. According to some applications, the flow rate of fluid from the surgical device is about 1 cubic centimeter per minute to 100 cubic centimeters per minute.

In one application, the rate of energy provided from the surgical device is about 1 watt to 400 watts.

In some applications, the energy source comprises a transducer and the energy comprises mechanical energy. In other applications, the energy source comprises a laser and the energy comprises radiant energy.

The surgical device, in some applications, is a monopolar electrosurgical device or a bipolar electrosurgical device.

In select applications, the fluid flow control mechanism comprises a manually activated device for changing, i.e., increasing or decreasing, the flow rate of fluid provided from the surgical device. This manually activated device can be at least one of a roller clamp, a flow rate controller, and a pump. In another select application, the energy control mechanism comprises a manually activated device for increasing or decreasing the rate of energy provided from the surgical device, and can be a selector switch of the energy source.

In other select applications, the fluid flow control mechanism comprises an automatically activated device for increasing or decreasing the fluid flow rate of fluid, and can be a flow rate controller. In another select application, the energy control mechanism comprises an automatically activated device for increasing or decreasing the rate of energy provided from the surgical device, such as an internal component of the energy source.

In some instances, the fluid flow control mechanism changes the flow rate as a result of a change in a rate of energy provided from the surgical device. The flow rate can change from a first non-zero flow rate to a second, non-zero flow rate, or, between any two non-zero flow rates. Similarly, the change in the rate of energy can be from a first non-zero rate of energy to a second non-zero rate of energy, or, between any two non-zero rates of energy.

According to certain selected applications, a surgical device for treating tissue comprises a tip portion comprising a housing and a contact element, the surgical device configured to provide energy and a fluid to a tissue. The housing comprises a cavity, a distal end, a proximal end, a fluid inlet opening and at least one fluid outlet opening with the fluid outlet opening located at the distal end of the housing. The contact element comprises a contact element portion retained within the cavity of the housing and a contact element portion extending distally through the fluid outlet opening located at the distal end of the housing. The contact element is retractable into the cavity of the housing upon the application of a proximally directed force against the portion of the contact element extending distally beyond the distal opening located at the distal end of the housing.

In some applications, the contact element has a shape, at least a portion of which is defined by a portion of a ball or a sphere. Typically, the contact element extends distally through the fluid outlet opening located at the distal end of the housing and comprises a blunt surface.

In some instances, the energy comprises electrical energy and the fluid comprises an electrically conductive fluid. The energy can be electrical energy, mechanical energy, thermal energy, radiant energy, and ultrasonic energy. The fluid can be electrically conductive fluid or non-electrically conductive fluid.

In one select application, at least one of the housing and the contact element provides the energy to the tissue. Additionally or alternatively, at least one of the housing and the contact element provides the fluid to the tissue. In some instances, the tip portion of the surgical device provides the energy and the fluid, either simultaneously or sequentially, to the tissue.

In another application, at least one of the housing and the contact element comprises an electrically conductive material. Further, in yet another application, at least one of the housing or the contact element comprises a porous material.

The fluid outlet opening located at the distal end of the housing can comprise a fluid outlet opening first portion and a fluid outlet opening second portion, with a contact element portion extending distally through the fluid outlet opening first portion and not extending distally through the fluid outlet opening second portion.

In certain applications, the contact element portion extends distally through the fluid outlet opening first portion and has a complementary shape to the fluid outlet opening first portion. The complementary shape of the contact element portion can be circular.

In certain other applications, the fluid outlet opening second portion comprises at least one slot. Additionally or alternatively, the fluid outlet opening second portion comprises at least one slot and further comprises a plurality of slots positioned around the fluid outlet opening first portion. According to another aspect of the invention, the fluid outlet opening second portion comprising a plurality of slots positioned around the fluid outlet opening first portion further comprises four slots equally positioned around the fluid outlet opening first portion.

The fluid outlet opening second portion can comprise at least one tissue separating edge.

In certain applications, the housing comprises a side wall relative to the distal end of the housing and at least one fluid outlet opening located in the side wall.

The retraction of the contact element can be biased by a retraction biasing member, and example of which is a spring.

A surgical device for treating tissue is provided by some embodiments. The surgical device comprises a tip portion configured to provide energy and a fluid to a tissue, the tip portion having a first tissue treating surface configured for blunt dissection of the tissue. In some configurations, the first tissue treating surface comprises a tissue separating edge adjacent a blunt surface. The tip portion can further comprise a second tissue treating surface configured for coagulation of a tissue. This second tissue treating surface could comprise a side surface of the tip portion. In some applications, the side surface of the tip portion further comprises a longitudinal side surface of the tip portion adjacent the first tissue treating surface.

Certain techniques disclosed provide a surgical method for treating tissue. The method comprises providing a surgical device which provides energy and a fluid to the tissue from a tip portion and blunt dissenting with the tip portion. The surgical method can be for treating a liver.

Certain additional embodiments provide a surgical device for treating tissues. The surgical devices comprises a tip portion comprising a tissue manipulator, the tissue manipulator having cooperating jaws, an energy-providing element operatively associated with the jaws to provide energy to the tissue manipulated by the jaws, a plurality of fluid outlets defined by and along the jaws, the fluid outlets to provide a fluid to the tissue manipulated by the jaws, and at least a portion of the jaws comprising a porous material, the porous material comprising at least one porous material fluid inlet surface and at least one porous material fluid outlet surface, the fluid inlet surface and the fluid outlet surface connected by a plurality of tortuous pathways in the porous material. The porous material can be hydrophilic.

In some applications, at least a portion of the jaws comprise a tissue-manipulating surface; the tissue-manipulating surface interrupted by a recess forming a fluid flow channel comprising a first side wall, a second opposing side wall and a bottom wall, at least a portion of the bottom wall of the flow channel comprising the energy-providing element, the fluid outlets provided through the energy-providing element from a manifold located beneath at least a portion of the energy-providing element, at least a portion of one of the first side wall or second side wall of the fluid flow channel comprising the porous material and at least a portion of the first side wall or second side wall surface comprising the fluid inlet surface and a tissue non-manipulating surface of the jaw comprising the fluid outlet surface.

In a certain embodiment, the surgical device comprises a cutting mechanism configured to retract proximally and extend distally along the jaws.

In some applications, the portion of one of the first side wall or second side wall of the fluid flow channel in the porous material comprises a portion of an outer side wall of the jaw, the portion of the first side wall or second side wall surface comprising the fluid inlet surface comprises an inner surface of an outer side wall and the tissue non-manipulating surface of the jaw comprises an outer surface of the outer side wall.

The porous material can further comprise a second porous material fluid outlet surface, and the second porous material fluid outlet surface can comprise at least a portion of the tissue-manipulating surface.

Another surgical device for treating tissue is also provided by the disclosure. This device comprises a tip portion comprising a tissue manipulator, the tissue manipulator having cooperating jaws, an energy-providing element operatively associated with the jaws to provide energy to the tissue manipulated by the jaws, a plurality of fluid outlets defined by and along the jaws, the fluid outlets to provide a fluid to the tissue manipulated by the jaws and an output related to the magnitude of a tissue within the jaws.

In some embodiments, the output is configured to provide an estimated tissue treatment time for the tissue or to provide a measurement on a measurement scale. This measurement could be unitless, or the measurement could comprise a tissue dimension (tissue length, tissue width or tissue thickness), or tissue area, or tissue volume. The measurement scale could be located on the surgical device (e.g. jaw, handle), and may comprise a scale of a dial gauge.

In some applications, a surgical device for treating tissue is provided, the device comprising a tip portion comprising a tissue manipulator, the tissue manipulator having cooperating jaws, an energy-providing element operatively associated with the jaws to provide energy to the tissue manipulated by the jaws, a plurality of fluid outlets defined along the jaws, the fluid outlets to provide a fluid to the tissue manipulated by the jaws and a fluid application mechanism which directs application of the fluid only to a portion of the jaws occupied by tissue.

In a further application disclosed, the fluid application mechanism can comprise a plurality of fluid valves which open the fluid outlets as a result of tissue contacting the valves or a gutter which retracts distally along the jaw as a result of tissue contacting a distal end of the gutter and directs fluid application from the distal end of the gutter to tissue.

According to certain techniques of this disclosure, a surgical method for treating tissue is provided. The surgical method comprises providing a surgical device comprising a tip portion, the tip portion comprising a tissue manipulator, the tissue manipulator having cooperating jaws, providing an energy-providing element operatively associated with the jaws to provide energy to the tissue manipulated by the jaws, providing a plurality of fluid outlets defined by and along the jaws, the fluid outlets to provide a fluid to the tissue manipulated by the jaws and providing an output related to the magnitude of a tissue within the jaws.

According to other techniques, a surgical method for treating tissue is provided, the method comprising providing a surgical device comprising a tip portion, the tip portion comprising a tissue manipulator, the tissue manipulator having cooperating jaws, providing an energy-providing element operatively associated with the jaws to provide energy to the tissue manipulated by the jaws, providing a plurality of fluid outlets defined along the jaws, the fluid outlets to provide a fluid to the tissue manipulated by the jaws and providing a fluid application mechanism which directs application of the fluid only to a portion of the jaws occupied by tissue.

Still further techniques provide a surgical method for treating tissue, the method comprising providing energy from energy source, providing a fluid from a fluid source, providing a surgical device which provides the energy and the fluid to the tissue, and changing a flow rate of fluid provided from the surgical device between at least two non-zero flow rates with a change in a rate of energy provided from the surgical device, which changes between at least two non-zero energy rates.

The change in the flow rate of fluid can be performed manually or automatically, and the change in the rate of energy can performed manually or automatically. The change in the flow rate of fluid can be performed independently of the change in the rate of energy provided from the surgical device. Alternately, the change in the flow rate of fluid can be performed dependently on the change in the rate of energy provided from the surgical device.

A further surgical method for treating tissue is provided, the method comprising providing energy from an energy source, providing a fluid from a fluid source, providing a surgical device which provides the energy and the fluid to the tissue, heating the tissue with the energy and controlling the heating of the tissue by vaporizing at least a portion of the fluid.

Another surgical method for treating tissue is provided, the method comprising providing energy from an energy source, providing a fluid from a fluid source, providing a surgical device which provides the energy and the fluid to the tissue, heating and vaporizing at least a portion of the fluid with the energy and changing a flow rate of the fluid to change a boiling percentage of the fluid.

Increasing or decreasing the flow rate of fluid provided from the surgical device preferably respectively increases or decreases the boiling percentage of the fluid.

A surgical method of treating tissue is provided which comprises providing energy from an energy source, providing a fluid from a fluid source, providing a surgical device which provides the energy and the fluid to the tissue, heating the tissue and the fluid with the energy, and dissipating heat from the fluid by vaporizing at least a portion of the fluid.

And further, a surgical method of treating tissue is provided that comprises providing energy from energy source, providing a fluid from a fluid source, the fluid having a boiling temperature, providing a surgical device which provides the energy and the fluid to the tissue, heating the tissue and the fluid with the energy and maintaining the temperature of the tissue at or below the boiling temperature of the fluid by dissipating heat from the fluid by vaporizing at least a portion of the fluid.

BRIEF DESCRIPTION OF THE DRAWINGS

FIG. 2 is a schematic graph that describes the relationship between RF power to tissue (P), flow rate of saline (Q), and tissue temperature (T) when heat conduction to adjacent tissue is considered;

FIG. 22 is a schematic section side view of the tip and shaft of the device shown in FIG. 21 and taken along line B—B of FIG. 24;

FIG. 23 is a schematic close-up section side view of the tip of the device bounded by circle 445 shown in FIG. 22 and taken along line B—B of FIG. 24;

FIG. 24 is a schematic end view of the tip of the device bound by circle 445 shown in FIG. 21;

FIG. 25 is a schematic close-up side view of tip of the device bounded by circle 445 in fluid coupling with tissue;

FIG. 26A is a schematic close-up view of an alternative tip of the device shown in FIG. 21;

FIG. 26B is a schematic close-up section side view of the tip of the device shown in FIG. 26A and taken along line 26b—26b of FIG. 26A

DETAILED DESCRIPTION

Figure 1:
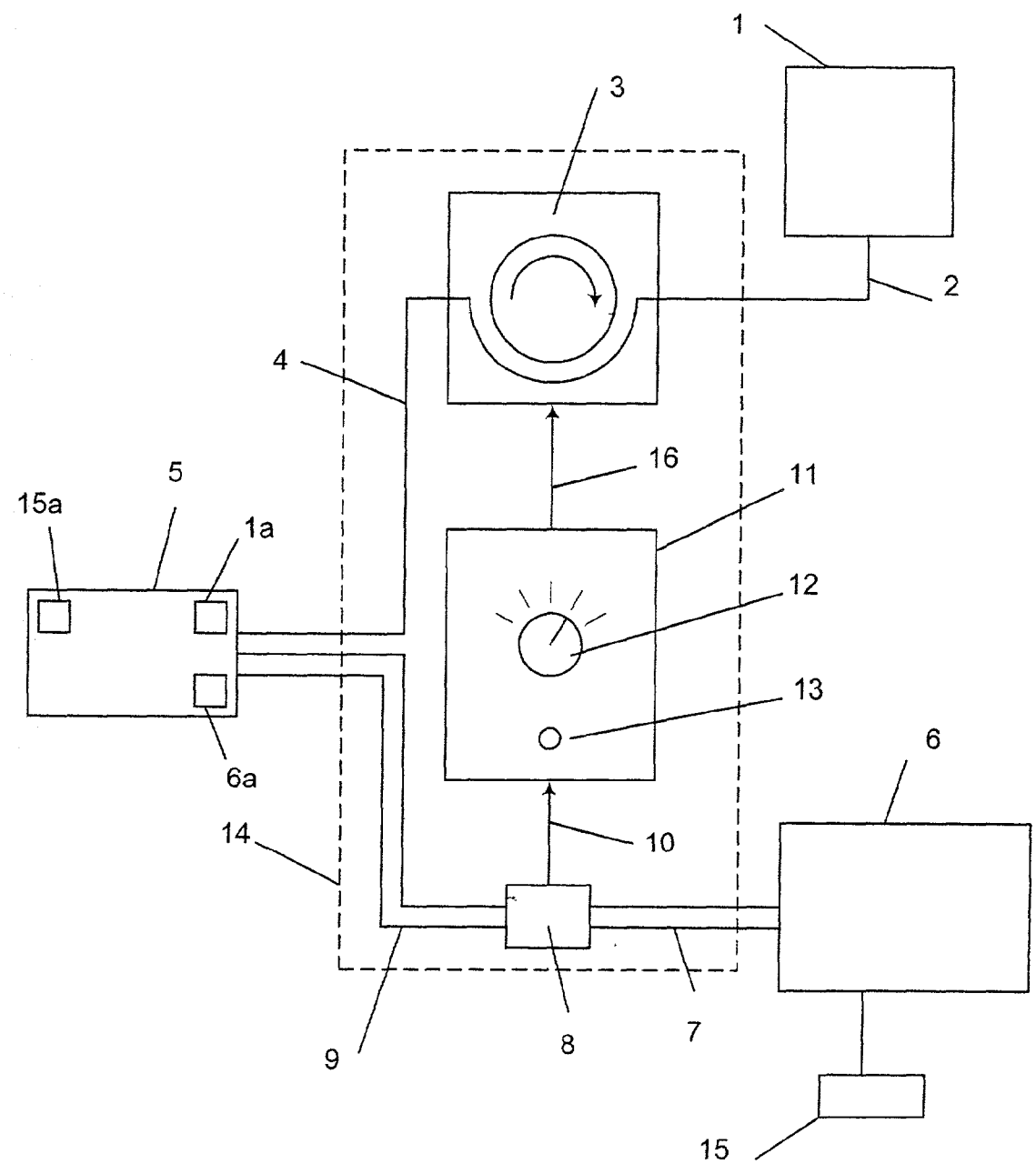
FIG. 1 is a block diagram showing one embodiment of the overall control system of the invention, and an electrosurgical device.

Throughout the present description, like reference numerals and letters indicate corresponding structure throughout the several views, and such corresponding structure need not be separately discussed. For elements similar to the various exemplary embodiments of the invention, an attempt has been made to hold each reference character within a particular numerical series constant. In other words, for example, an element referenced at 10 in one exemplary embodiment is correspondingly referenced at 110, 210, and so forth in subsequent exemplary embodiments. Thus, where an exemplary embodiment description uses a reference numeral to refer to an element, the reference numeral generally applies equally, as distinguished by series, to the other exemplary embodiments where the element is common. Furthermore, any particular feature(s) of a particular exemplary embodiment may be equally applied to any other exemplary embodiment(s) of this specification as suitable. In other words, features between the various exemplary embodiments described herein are interchangeable, and not exclusive.

The invention provides systems, devices and methods that preferably improve control of tissue temperature at a treatment site during a medical procedure. The invention is particularly useful during surgical procedures upon tissues of the body, where tissue is often cut and coagulated. The invention preferably involves the use of electrosurgical procedures, which preferably utilize RF power and conductive fluid to treat tissue. Preferably, a desired tissue temperature range is achieved through adjusting parameters, such as conductive fluid flow rate, that affect the temperature at the tissue/electrode interface. Preferably, the device achieves a desired tissue temperature utilizing a desired percentage boiling of the conductive solution at the tissue/electrode interface. In a preferred embodiment, the invention provides a control device, the device comprising a flow rate controller that receives a signal indicating power applied to the system, and adjusts the flow rate of conductive fluid from a fluid source to an electrosurgical device. The invention also contemplates a control system comprising a flow rate controller, a measurement device that measures power applied to the system, and a pump that provides fluid at a selected flow rate.

The invention will be discussed generally with reference to FIG. 1. FIG. 1 shows a block diagram of one exemplary embodiment of a system of the invention. Preferably, as shown in FIG. 1, an electrically conductive fluid is provided from a fluid source 1, through a fluid line 2, to a pump 3, which has an outlet fluid line 4 that is connected to an electrosurgical device 5. In a preferred embodiment, the conductive fluid comprises a saline solution. More preferably, the saline comprises sterile, and even more preferably, normal saline. Although the description herein will specifically describe the use of saline as the fluid, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

While a conductive fluid is preferred, as will become more apparent with further reading of this specification, the fluid may also comprise an electrically non-conductive fluid. The use of a non-conductive fluid is less preferred to that of a conductive fluid as the non-conductive fluid does not conduct electricity. However, the use of a non-conductive fluid still provides certain advantages over the use of a dry electrode including, for example, reduced occurrence of tissue sticking to the electrode. Therefore, it is also within the scope of the invention to include the use of a non-conducting fluid, such as, for example, dionized water.

Energy to heat tissue is provided from energy source, such as an electrical generator 6 which preferably provides RF alternating current energy via a cable 7 to energy source output measurement device, such as a power measurement device 8 that measures the RF alternating current electrical power. In this exemplary embodiment, preferably the power measurement device 8 does not turn the power off or on, or alter the power in any way. A power switch 15 connected to the generator 6 is preferably provided by the generator manufacturer and is used to turn the generator 6 on and off. The power switch 15 can comprise any switch to turn the power on and off, and is commonly provided in the form of a footswitch or other easily operated switch, such as a switch 15a mounted on the electrosurgical device 5. The power switch may also function as a manually activated device for increasing or decreasing the rate of energy provided from the surgical device 5. Alternatively, internal circuitry and other components of the generator 6 may be used for automatically increasing or decreasing the rate of energy provided from the surgical device 5. A cable 9 preferably carries RF energy from the power measurement device 8 to the electrosurgical device 5. Power, or any other energy source output, is preferably measured before it reaches the electrosurgical device 5.

For the situation where capacitation and induction effects are negligibly small, from Ohm's law, power P, or the rate of energy delivery (e.g. joules/sec), may be expressed by the product of current times voltage (i.e. I×V), the current squared times resistance (i.e. $I^2 \times R$), or the voltage squared divided by the resistance (i.e. $V^2/R$); where the current I may be measured in amperes, the voltage V may be measured in volts, the electrical resistance R may be measured in ohms, and the power P may be measured in watts (joules/sec). Given that power P is a function of current I, voltage V, and resistance R as indicated above, it should be understood, that a change in power P is reflective of a change in at least one of the input variables. Thus, one may alternatively measure changes in such input variables themselves, rather than power P directly, with such changes in the input variables mathematically corresponding to a changes in power P as indicated above.

As to the frequency of the RF electrical energy, it is preferably provided within a frequency band (i.e. a continuous range of frequencies extending between two limiting frequencies) in the range between and including about 9 kHz (kilohertz) to 300 GHz (gigahertz). More preferably, the RF energy is provided within a frequency band in the range between and including about 50 kHz (kilohertz) to 50 MHz (megahertz). Even more preferably, the RF energy is provided within a frequency band in the range between and including about 200 kHz (kilohertz) to 2 MHz (megahertz). Most preferably, RF energy is provided within a frequency band in the range between and including about 400 kHz (kilohertz) to 600 kHz (kilohertz). Further, it should also be understood that, for any frequency band identified above, the range of frequencies may be further narrowed in increments of 1 (one) hertz anywhere between the lower and upper limiting frequencies.

While RF electrical energy is preferred, it should be understood that the electrical energy (i.e., energy made available by the flow of electric charge, typically through a conductor or by self-propagating waves) may comprise any frequency of the electromagnetic spectrum (i.e. the entire range of radiation extending in frequency from $10^{23}$ hertz to 0 hertz) and including, but not limited to, gamma rays, x-rays, ultraviolet radiation, visible light, infrared radiation, microwaves, and any combinations thereof.

With respect to the use of electrical energy, heating of the tissue is preferably performed by means of resistance heating. In other words, increasing the temperature of the tissue as a result of electric current flow through the tissue, with the electrical energy being absorbed from the voltage and transformed into thermal energy (i.e. heat) via accelerated movement of ions as a function of the tissue's electrical resistance.

Heating with electrical energy may also be performed by means of dielectric heating (capacitation). In other words, increasing the temperature of the tissue through the dissipation of electrical energy as a result of internal dielectric loss when the tissue is placed in a varying electric field, such as a high-frequency (e.g. microwave), alternating electromagnetic field.

Dielectric loss is the electrical energy lost as heat in the polarization process in the presence of the applied electric field. In the case of an alternating current field, the energy is absorbed from the alternating current voltage and converted to heat during the polarization of the molecules.

However, it should be understood that energy provided to heat the tissue may comprise surgical devices other than electrosurgical devices, energy sources other than generators, energy forms other than electrical energy and mechanisms other than resistance heating. For example, providing thermal energy to the tissue from energy source with a difference (e.g. higher) in temperature. Such may be provided, for example, to the tissue from a heated device, which heats tissue through direct contact with the energy source (conduction), heats through contact with a flowing fluid (convection), or from a remote heat source (radiation).

Also, for example, providing energy to the tissue may be provided via mechanical energy which is transformed into thermal energy via accelerated movement of the molecules, such as by mechanical vibration provided, for example, by energy source such as a transducer containing a piezoelectric substance (e.g., a quartz-crystal oscillator) that converts high-frequency electric current into vibrating ultrasonic waves which may be used by, for example, an ultrasonic surgical device.

Also, for example, providing energy to the tissue may be provided via radiant energy (i.e. energy which is transmitted by radiation/waves) which is transformed into thermal energy via absorption of the radiant energy by the tissue. Preferably the radiation/waves comprise electromagnetic radiation/waves which include, but is not limited to, radio waves, microwaves, infrared radiation, visible light radiation, ultraviolet radiation, x-rays and gamma rays. More preferably, such radiant energy comprises energy with a frequency of $3 \times 10^{11}$ hertz to $3 \times 10^{16}$ hertz (i.e. the infrared, visible, and ultraviolet frequency bands of the electromagnetic spectrum). Also preferably the electromagnetic waves are coherent and the electromagnetic radiation is emitted from energy source such as a laser device. A flow rate controller 11 preferably includes a selection switch 12 that can be set to achieve desired levels of percentage fluid boiling (for example, 100%, 98%, 80% boiling). Preferably, the flow rate controller 11 receives an input signal 10 from the power measurement device 8 and calculates an appropriate mathematically predetermined fluid flow rate based on percentage boiling indicated by the selection switch 12. In a preferred embodiment, a fluid switch 13 is provided so that the fluid system can be primed (air eliminated) before turning the generator 6 on. The output signal 16 of the flow rate controller 11 is preferably sent to the pump 3 motor to regulate the flow rate of conductive fluid, and thereby provide an appropriate fluid flow rate which corresponds to the amount of power being delivered.

In one exemplary embodiment, the invention comprises a flow rate controller that is configured and arranged to be connected to a source of RF power, and a source of fluid, for example, a source of conductive fluid. The device of the invention receives information about the level of RF power applied to an electrosurgical device, and adjusts the flow rate of the fluid to the electrosurgical device, thereby controlling temperature at the tissue treatment site.

In another exemplary embodiment, elements of the system are physically included together in one electronic enclosure. One such embodiment is shown by enclosure within the outline box 14 of FIG. 1. In the illustrated embodiment, the pump 3, flow rate controller 11, and power measurement device 8 are enclosed within an enclosure, and these elements are connected through electrical connections to allow signal 10 to pass from the power measurement device 8 to the flow rate controller 11, and signal 16 to pass from the flow rate controller 11 to the pump 3. Other elements of a system can also be included within one enclosure, depending upon such factors as the desired application of the system, and the requirements of the user.

The pump 3 can be any suitable pump used in surgical procedures to provide saline or other fluid at a desired flow rate. Preferably, the pump 3 comprises a peristaltic pump. With a rotary peristaltic pump, typically a fluid is conveyed within the confines of a flexible tube by waves of contraction placed externally on the tube which are produced mechanically, typically by rotating rollers which squeeze the flexible tubing against a support intermittently. Alternatively, with a linear peristaltic pump, typically a fluid is conveyed within the confines of a flexible tube by waves of contraction placed externally on the tube which are produced mechanically, typically by a series of compression fingers or pads which squeeze the flexible tubing against a support sequentially. Peristaltic pumps are generally preferred for use as the electromechanical force mechanism (e.g. rollers driven by electric motor) does not make contact the fluid, thus reducing the likelihood of inadvertent contamination.

Alternatively, pump 3 can be a "syringe pump", with a built-in fluid supply. With such a pump, typically a filled syringe is located on an electromechanical force mechanism (e.g. ram driven by electric motor) which acts on the plunger of the syringe to force delivery of the fluid contained therein. Alternatively, the syringe pump may comprise a double-acting syringe pump with two syringes such that they can draw saline from a reservoir, either simultaneously or intermittently. With a double acting syringe pump, the pumping mechanism is generally capable of both infusion and withdrawal. Typically, while fluid is being expelled from one syringe, the other syringe is receiving fluid therein from a separate reservoir. In this manner, the delivery of fluid remains continuous and uninterrupted as the syringes function in series. Alternatively, it should be understood that a multiple syringe pump with two syringes, or any number of syringes, may be used in accordance with the invention.

Furthermore, fluid, such as conductive fluid, can also be provided from an intravenous (IV) bag full of saline that flows under the influence (i.e. force) of gravity. In such a manner, the fluid may flow directly to the electrosurgical device 5, or first to the pump 3 located there between. Alternatively, fluid from a fluid source such as an IV bag can be provided through an IV flow controller that may provide a desired flow rate by adjusting the cross sectional area of a flow orifice (e.g. lumen of the connective tubing with the electrosurgical device) while sensing the flow rate with a sensor such as an optical drop counter. Furthermore, fluid from a fluid source such as an IV bag an be provided through a manually or automatically activated device such as a flow controller, such as a roller clamp, which also adjusts the cross sectional area of a flow orifice and may be adjusted manually by, for example, the user of the device in response to their visual observation (e.g. fluid boiling) at the tissue treatment site or a pump.

Similar pumps can be used in connection with the invention, and the illustrated embodiments are exemplary only. The precise configuration of the pump 3 is not critical to the invention. For example, pump 3 may include other types of infusion and withdrawal pumps.

Furthermore, pump 3 may comprise pumps which may be categorized as piston pumps, rotary vane pumps (e.g. blower, axial impeller, centrifugal impeller), cartridge pumps and diaphragm pumps. In some embodiments, the pump can be substituted with any type of flow controller, such as a manual roller clamp used in conjunction with an IV bag, or combined with the flow controller to allow the user to control the flow rate of conductive fluid to the device. Alternatively, a valve configuration can be substituted for pump 3.

Furthermore, similar configurations of the system can be used in connection with the invention, and the illustrated embodiments are exemplary only. For example, the fluid source 1 pump 3, generator 6, power measurement device 8 or flow rate controller 11, or any other components of the system not expressly recited above, may comprise a portion of the electrosurgical device 5. For example, in one exemplary embodiment the fluid source may comprise a compartment of the electrosurgical device 5 which contains fluid, as indicated at reference character 1*a*. In another exemplary embodiment, the compartment may be detachably connected to the electrosurgical device 5, such as a canister which may be attached via threaded engagement with the device 5. In yet another exemplary embodiment, the compartment may be configured to hold a pre-filled cartridge of fluid, rather than the fluid directly.

Also for example, with regards to the generator, energy source, such as a direct current (DC) battery used in conjunction with inverter circuitry and a transformer to produce alternating current at a particular frequency, may comprise a portion of the electrosurgical device 5, as indicated at reference character 6*a*. In one embodiment the battery element of the energy source may comprise a rechargeable battery. In yet another exemplary embodiment, the battery element may be detachably connected to the electrosurgical device 5, such as for recharging. In yet other exemplary embodiments, either the fluid or the energy source may be located on (e.g. within) the proximal (to the user of the device 5*a*) handle 20 (see FIG. 7) of the electrosurgical device 5, or the shaft 17 of the electrosurgical device 5. Handle 20 is preferably made of a sterilizable, rigid, and non-conductive material, such as a polymer (e.g. polycarbonate). The components of the system will now be described in further detail. From the specification, it should be clear that any use of the terms "distal" and "proximal" are made in reference from the user of the device, and not the patient.

Figure 2A:
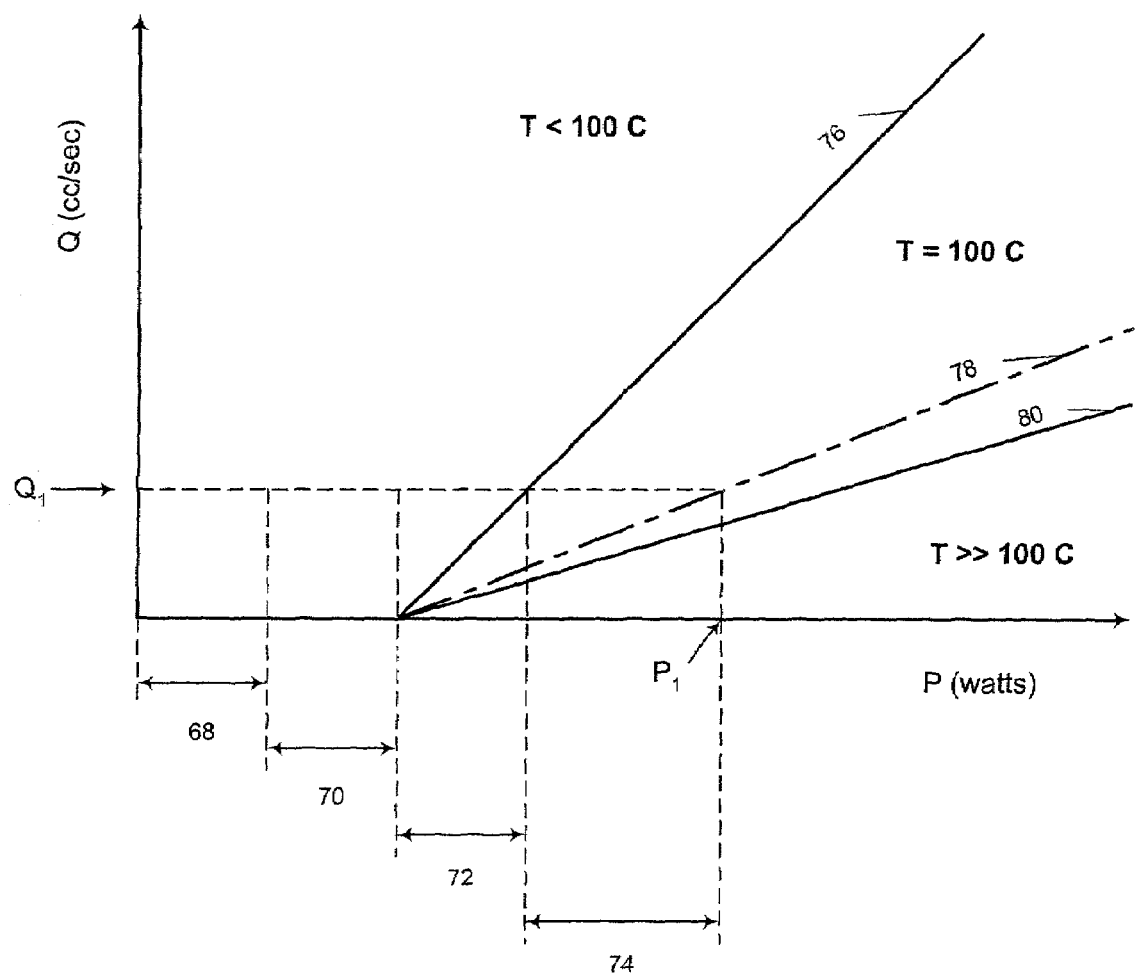
FIG. 2A is a schematic graph that describes the relationship between RF power to tissue (P), flow rate of saline (Q), and tissue temperature (T) when the heat required to warm the tissue to the peak temperature (T) 68 is considered.

The flow rate controller 11 controls the rate of flow from the fluid source 1. Preferably, the rate of fluid flow from the fluid source 1 is based upon the amount of RF power provided from the generator 6 to the electrosurgical device 5. In other words, as shown in FIG. 2, preferably there is a relationship between the rate of fluid flow and the RF power. More precisely, as shown in FIG. 2, the relationship between the rate of fluid flow and RF power may be expressed as a direct, linear relationship. The flow rate of conductive fluid, such as saline, interacts with the RF power and various modes of heat transfer away from the target tissue, as described herein.

Throughout this disclosure, when the terms "boiling point of saline", "vaporization point of saline", and variations thereof are used, what is intended is the boiling point of the water in the saline solution.

FIG. 2 shows a schematic graph that describes the relationship between the flow rate of saline, RF power to tissue, and regimes of boiling as detailed below. Based on a simple one-dimensional lumped parameter model of the heat transfer, the peak tissue temperature can be estimated, and once tissue temperature is estimated, it follows directly whether it is hot enough to boil saline.

$$P = \Delta T/R + \rho c_p Q_1 \Delta T + \rho Q_b h_v \qquad (1)$$

where P=the total RF electrical power that is converted into heat.

Conduction. The first term [$\Delta T/R$] in equation (1) is heat conducted to adjacent tissue, represented as 70 in FIG. 2, where:
- $\Delta T = (T - T_\infty)$ the difference in temperature between the peak tissue temperature (T) and the normal temperature ($T_\infty$) of the body tissue (° C.). Normal temperature of the body tissue is generally 37° C.; and
- R=Thermal resistance of surrounding tissue, the ratio of the temperature difference to the heat flow (° C./watt).

This thermal resistance can be estimated from published data gathered in experiments on human tissue (Phipps, J. H., "Thermometry studies with bipolar diathermy during hysterectomy," *Gynaecological Endoscopy*, 3:5–7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320 - 37)/50 = 5.7 \approx 6° \text{ C./watt}$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than about 100° C. to inhibit desiccation of the tissue. Assuming that saline boils at about 100° C., the first term in equation (1) ($\Delta T/R$) is equal to (100−37)/6=10.5 watts. Thus, based on this example, the maximum amount of heat conducted to adjacent tissue without any significant risk of tissue desiccation is 10.5 watts.

Referring to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection. The second term [$\rho c_p Q_1 \Delta T$] in equation (1) is heat used to warm up the flow of saline without boiling the saline, represented as 72 in FIG. 2, where:
- $\rho$=Density of the saline fluid that gets hot but does not boil (approximately 1.0 gm/cm$^3$);
- $c_p$=Specific heat of the saline (approximately 4.1 watt-sec/gm-° C.);
- $Q_1$=Flow rate of the saline that is heated (cm$^3$/sec); and
- $\Delta T$=Temperature rise of the saline. Assuming that the saline is heated to body temperature before it gets to the electrode, and that the peak saline temperature is similar to the peak tissue temperature, this is the same $\Delta T$ as for the conduction calculation above.

The onset of boiling can be predicted using equation (1) with the last term on the right set to zero (no boiling) ($\rho Q_b h_v = 0$), and solving equation (1) for $Q_1$ leads to:

$$Q_1 = [P - \Delta T/R]/\rho c_p \Delta T \qquad (2)$$

This equation defines the line shown in FIG. 2 as the line of onset of boiling 76.

Boiling. The third term [$\rho Q_b h_v$] in equation (1) relates to heat that goes into converting the water in liquid saline to water vapor, and is represented as 74 in FIG. 2, where:
- $Q_b$=Flow rate of saline that boils (cm$^3$/sec); and
- $h_v$=Heat of vaporization of saline (approximately 2,000 watt-sec/gm).

A flow rate of only 1 cc/min will absorb a significant amount of heat if it is completely boiled, or about $\rho Q_b h_v = (1)(\frac{1}{60})(2,000) = 33.3$ watts. The heat needed to warm this flow rate from body temperature to 100° C. is much less, or $\rho c_p Q_1 \Delta T = (1)(4.1)(\frac{1}{60})(100-37) = 4.3$ watts. In other words, the most significant factor contributing to heat transfer from a wet electrode device can be fractional boiling. The present invention recognizes this fact and exploits it.

Fractional boiling can be described by equation (3) below:

$$Q_1 = \frac{\{P - \Delta T/R\}}{\{\rho c_p \Delta T + \rho h_v Q_b/Q_l\}} \qquad (3)$$

If the ratio of $Q_b/Q_1$ is 0.50 this is the 50% boiling line 78 shown in FIG. 2. If the ratio is 1.0 this is the 100% boiling line 80 shown in FIG. 2.

As indicated previously in the specification, using a fluid to couple energy to tissue inhibits such undesirable effects as sticking, desiccation, smoke production and char formation, and that one key factor is inhibiting tissue desiccation, which occur if the tissue temperature exceeds 100° C. and all the intracellular water boils away, leaving the tissue extremely dry and much less electrically conductive.

As shown in FIG. 2, one control strategy or mechanism which can be employed for the electrosurgical device 5 is to adjust the power P and flow rate Q such that the power P used at a corresponding flow rate Q is equal to or less than the power P required to boil 100% of the fluid and does not exceed the power P required to boil 100% of the fluid. In other words, this control strategy targets using the electrosurgical device 5 in the regions of FIG. 2 identified as T<100° C. and T=100° C., and includes the 100% boiling line 80. Stated another way, this control strategy targets not using the electrosurgical device 5 only in the region of FIG. 2 identified as T>>100° C.

Another control strategy that can be used for the electrosurgical device 5 is to operate the device 5 in the region T<100° C., but at high enough temperature to shrink tissue containing Type I collagen (e.g., walls of blood vessels, bronchi, bile ducts, etc.), which shrinks when exposed to about 85° C. for an exposure time of 0.01 seconds, or when exposed to about 65° C. for an exposure time of 15 minutes. An exemplary target temperature/time for tissue shrinkage is about 75° C. with an exposure time of about 1 second. As discussed herein, a determination of the high end of the scale (i.e., when the fluid reaches 100° C.) can be made by the phase change in the fluid from liquid to vapor. However, a determination at the low end of the scale (e.g., when the fluid reaches, for example, 75° C. for 1 second) requires a different mechanism as the temperature of the fluid is below the boiling temperature and no such phase change is apparent. In order to determine when the fluid reaches a temperature that will facilitate tissue shrinkage, for example 75° C., a thermochromic material, such as a thermochromic dye (e.g., leuco dye), may be added to the fluid. The dye can be formulated to provide a first predetermined color to the fluid at temperatures below a threshold temperature, such as 75° C., then, upon heating above 75° C., the dye provides a second color, such as clear, thus turning the fluid clear (i.e. no color or reduction in color). This color change may be gradual, incremental, or instant. Thus, a change in the color of the fluid, from a first color to a second color (or lack thereof) provides a visual indication to the user of the electrosurgical device 5 as to when a threshold fluid temperature below boiling has been achieved. Thermochromic dyes are available, for example, from Color Change Corporation, 1740 Cortland Court, Unit A, Addison, Ill. 60101.

It is also noted that the above mechanism (i.e., a change in the color of the fluid due to a dye) may also be used to detect when the fluid reaches a temperature which will facilitate tissue necrosis; this generally varies from about 60° C. for an exposure time of 0.01 seconds and decreasing to about 45° C. for an exposure time of 15 minutes. An exemplary target temperature/time for tissue necrosis is about 55° C. for an exposure time of about 1 second.

In order to reduce coagulation time, use of the electrosurgical device 5 in the region T=100° C. of FIG. 2 is preferable to use of the electrosurgical device 5 in the region T<100° C. Consequently, as shown in FIG. 2, another control strategy which may be employed for the electrosurgical device 5 is to adjust the power P and flow rate Q such that the power P used at a corresponding flow rate Q is equal to or more than the power P required to initiate boiling of the fluid, but still less than the power P required to boil 100% of the fluid. In other words, this control strategy targets using the electrosurgical device 5 in the region of FIG. 2 identified as T=100° C., and includes the lines of the onset of boiling 76 and 100% boiling line 80. Stated another way, this control strategy targets use using the electrosurgical device 5 on or between the lines of the onset of boiling 76 and 100% boiling line 80, and not using the electrosurgical device 5 in the regions of FIG. 2 identified as T<100° C. and T>>100° C.

For consistent tissue effect, it is desirable to control the saline flow rate so that it is always on a "line of constant % boiling" as, for example, the line of the onset of boiling 76 or the 100% boiling line 80 or any line of constant % boiling located in between (e.g. 50% boiling line 78) as shown in FIG. 2. Consequently, another control strategy that can be used for the electrosurgical device 5 is to adjust power P and flow rate Q such that the power P used at a corresponding flow rate Q targets a line of constant % boiling.

It should be noted, from the preceding equations, that the slope of any line of constant % boiling is known. For example, for the line of the onset of boiling 76, the slope of the line is given by $(\rho c_p \Delta T)$, while the slope of the 100% boiling line 80 is given by $1/(\rho c_p \Delta T + \rho h_v)$. As for the 50% boiling line 78, for example, the slope is given by $1/(\rho c_p \Delta T + \rho h_v 0.5)$.

If, upon application of the electrosurgical device 5 to the tissue, boiling of the fluid is not detected, such indicates that the temperature is less than 100° C. as indicated in the area of FIG. 2, and the flow rate Q must be decreased to initiate boiling. The flow rate Q may then decreased until boiling of the fluid is first detected, at which time the line of the onset of boiling 76 is transgressed and the point of transgression on the line 76 is determined. From the determination of a point on the line of the onset of boiling 76 for a particular power P and flow rate Q, and the known slope of the line 76 as outlined above (i.e. $1/\rho c_p \Delta T$), it is also possible to determine the heat conducted to adjacent tissue 70.

Conversely, if upon application of the electrosurgical device 5 to the tissue, boiling of the fluid is detected, such indicates that the temperature is approximately equal to 100° C. as indicated in the areas of FIG. 2, and the flow rate Q must be increased to reduce boiling until boiling stops, at which time the line of the onset of boiling 76 is transgressed and the point of transgression on the line 76 determined. As with above, from the determination of a point on the line of the onset of boiling 76 for a particular power P and flow rate Q, and the known slope of the line 76, it is also possible to determine the heat conducted to adjacent tissue 70.

With regards to the detection of boiling of the fluid, such may be physically detected by the user (e.g. visually by the naked eye) of the electrosurgical device 5 in the form of either bubbles or steam evolving from the fluid coupling at the electrode/tissue interface.

Alternatively, such a phase change (i.e. from liquid to vapor or vice-versa) may be measured by a sensor (See FIG. 10 at 79) which preferably senses either an absolute change (e.g. existence or non-existence of boiling with binary response such as yes or no) or a change in a physical quantity or intensity and converts the change into a useful input signal for an information-gathering system. For example, the phase change associated with the onset of boiling may be detected by a pressure sensor, such as a pressure transducer, located on the electrosurgical device 5. Alternatively, the phase change associated with the onset of boiling may be detected by a temperature sensor, such as a thermistor or thermocouple, located on the electrosurgical device 5, such as adjacent to the electrode. Also alternatively, the phase change associated with the onset of boiling may be detected by a change in the electric properties of the fluid itself. For example, a change in the electrical resistance of the fluid may be detected by an ohm meter; a change in the amperage may be measured by an amp meter; as change in the voltage may be detected by a volt meter; and a change in the power may be determined by a power meter.

Figure 3:
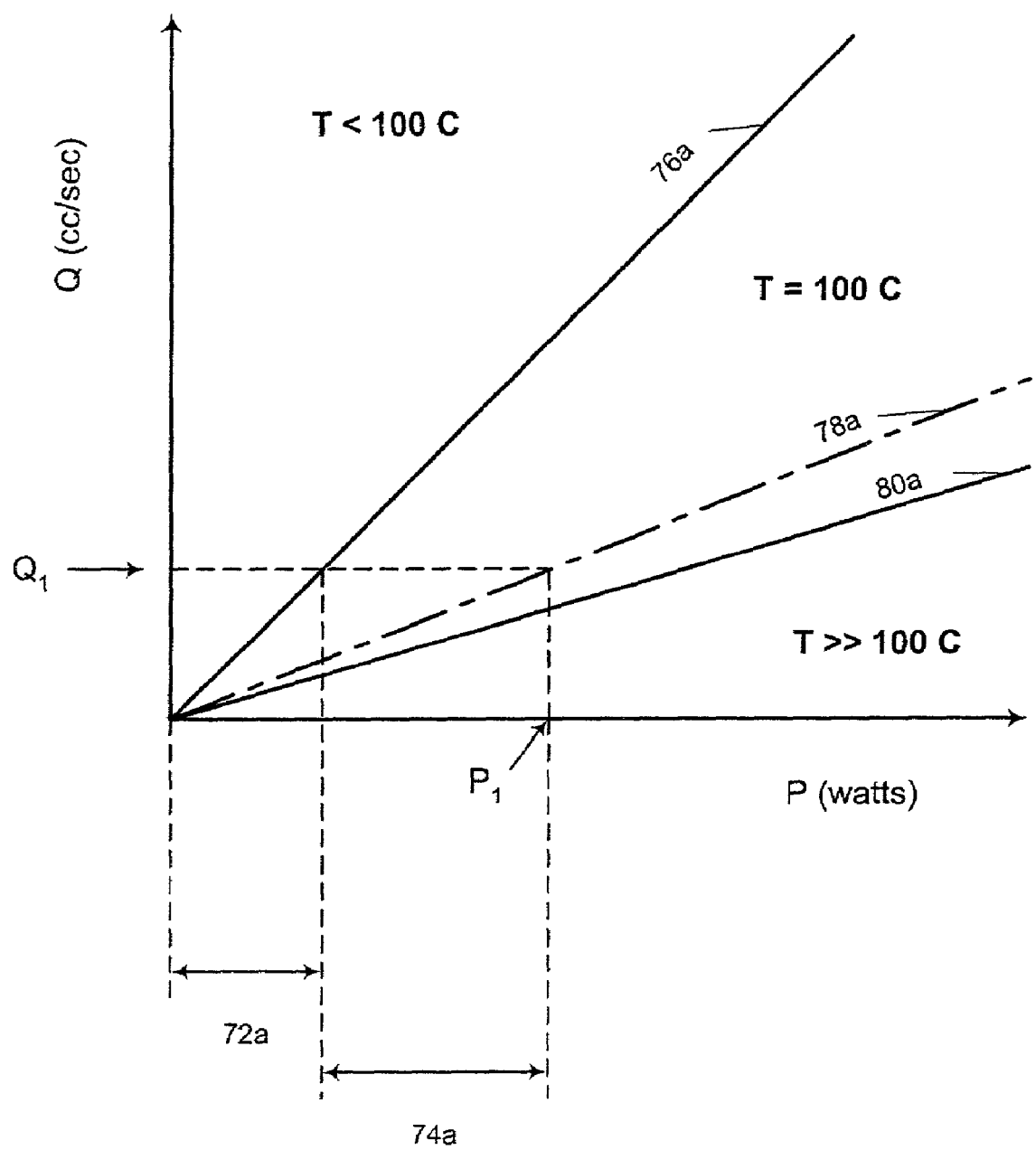
FIG. 3 is schematic graph that describes the relationship between RF power to tissue (P), flow rate of saline (Q), and tissue temperature (T) when heat conduction to adjacent tissue is neglected.

Yet another control strategy which may be employed for the electrosurgical device 5 is to eliminate the heat conduction term of equation (1) (i.e. $\Delta T/R$). Since the amount of heat conducted away to adjacent tissue can be difficult to precisely predict, as it may vary, for example, by tissue type, it may be preferable, from a control point of view, to assume the worst case situation of zero heat conduction, and provide enough saline so that if necessary, all the RF power could be used to heat up and boil the saline, thus providing that the peak tissue temperature will not go over 100° C. a significant amount. This situation is shown in the schematic graph of FIG. 3.

Stated another way, if the heat conducted to adjacent tissue 70 is overestimated, the power P required to intersect the 100% boiling line 80 will, in turn, be overestimated and the 100% boiling line 80 will be transgressed into the T>>100° C. region of FIG. 2, which is undesirable as established above. Thus, assuming the worse case situation of zero heat conduction provides a "safety factor" to avoid transgressing the 100% boiling line 80.

Assuming heat conduction to adjacent tissue 70 to be zero also provides the advantage of eliminating the only term from equation (1) which is tissue dependent, i.e., depends on tissue type. Thus, provided $\rho$, $c_p$, $\Delta T$, and $h_v$ are known as indicated above, the equation of the line for any line of constant % boiling is known. Thus, for example, the 98% boiling line, 80% boiling line, etc. can be determined in response to a corresponding input from the selection switch 12. In order to promote flexibility, it should be understood that the input from the selection switch preferably may comprise any percentage of boiling. Preferably the percentage of boiling may be selected in single percent increments (i.e. 100%, 99%, 98%, etc.).

Upon determination of the line of the onset of boiling 76, the 100% boiling line 80 or any line of constant % boiling there between, it is generally desirable to control the flow rate Q so that it is always on a particular line of constant % boiling for consistent tissue effect. In such a situation, the flow rate controller 11 will adjust the flow rate Q of the fluid to reflect changes in power P provided by the generator 6, as discussed in greater detail below. For such a use the flow rate controller may be set in a line of constant boiling mode, upon which the % boiling is then correspondingly selected.

As indicated above, it is desirable to control the saline flow rate Q so that it is always on a line of constant % boiling for consistent tissue effect. However, the preferred line of constant % boiling may vary based on the type of electrosurgical device 5. For example, if the device is monopolar and shunting through saline is not an issue, then it can be preferable to operate close to or directly on, but not over the line of the onset of boiling, such as 76a in FIG. 3. This preferably keeps tissue as hot as possible without causing desiccation. Alternatively, if the device is bipolar and shunting of electrical energy through excess saline is an issue, then it can be preferable to operate along a line of constant boiling, such as line 78a in FIG. 3, the 50% line. This simple proportional control will have the flow rate determined by equation (4), where K is the proportionality constant:

$$Q_1 = K \times P \quad (4)$$

In essence, when power P goes up, the flow rate Q will be proportionately increased. Conversely, when power P goes down, the flow rate Q will be proportionately decreased.

The proportionality constant K is primarily dependent on the fraction of saline that boils, as shown in equation (5), which is equation (3) solved for K after eliminating P using equation (4), and neglecting the conduction term ($\Delta T/R$):

$$K = \frac{1}{\{\rho c_p \Delta T + \rho h_v Q_b / Q_l\}} \quad (5)$$

Thus, the present invention provides a method of controlling boiling of fluid, such as a conductive fluid, at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

Figure 4:
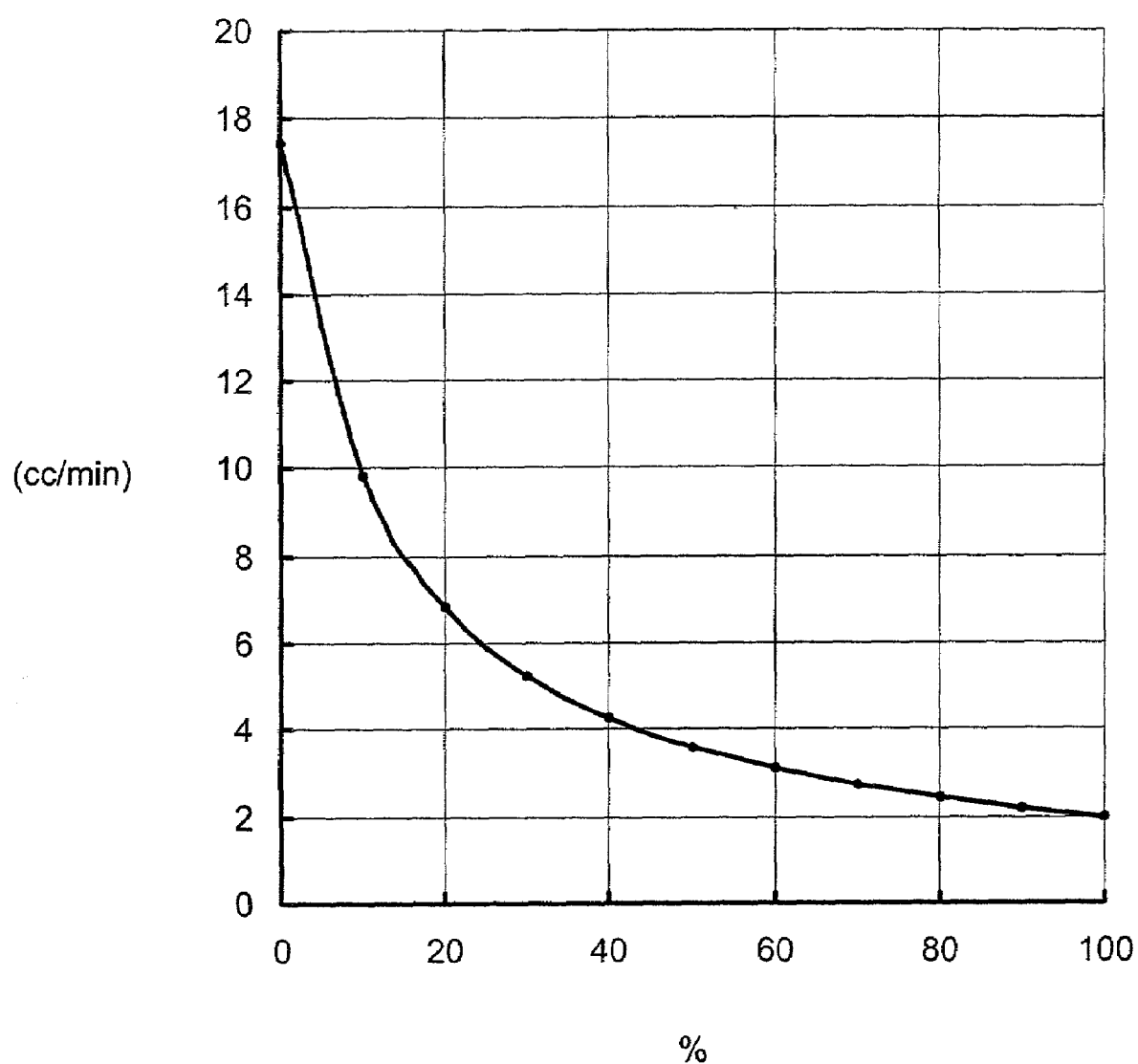
FIG. 4 is a graph showing the relationship of percentage saline boiling and saline flow rate (cc/min) for an exemplary RF generator output of 75 watts.

FIG. 4 shows an exemplary graph of flow rate Q versus % boiling for a situation where the RF power P is 75 watts. The percent boiling is represented on the X-axis, and the saline flow rate Q (cc/min) is represented on the Y-axis. According to this example, at 100% boiling the most desirable predetermined saline flow rate Q is 2 cc/min. Also according to this example, flow rate Q versus % boiling at the remaining points of the graft illustrates a non-linear relationship as follows:

TABLE 1

| % Boiling and Flow Rate Q (cc/min) at RF Power P of 75 watts | |
| --- | --- |
| 0% | 17.4 |
| 10% | 9.8 |
| 20% | 6.8 |
| 30% | 5.2 |
| 40% | 4.3 |
| 50% | 3.6 |
| 60% | 3.1 |
| 70% | 2.7 |
| 80% | 2.4 |
| 90% | 2.2 |
| 100% | 2.0 |

Typical RF generators used in the field have a power selector switch to 300 watts of power, and on occasion some have been found to be selectable up to 400 watts of power. In conformance with the above methodology, at 0% boiling with a corresponding power of 300 watts, the calculated flow rate Q is 69.7 cc/min and with a corresponding power of 400 watts the calculated flow rate Q is 92.9 cc/min. Thus, when used with typical RF generators in the field, a fluid flow rate Q of about 100 cc/min or less with the present invention is expected to suffice for the vast majority of applications.

Figure 5:
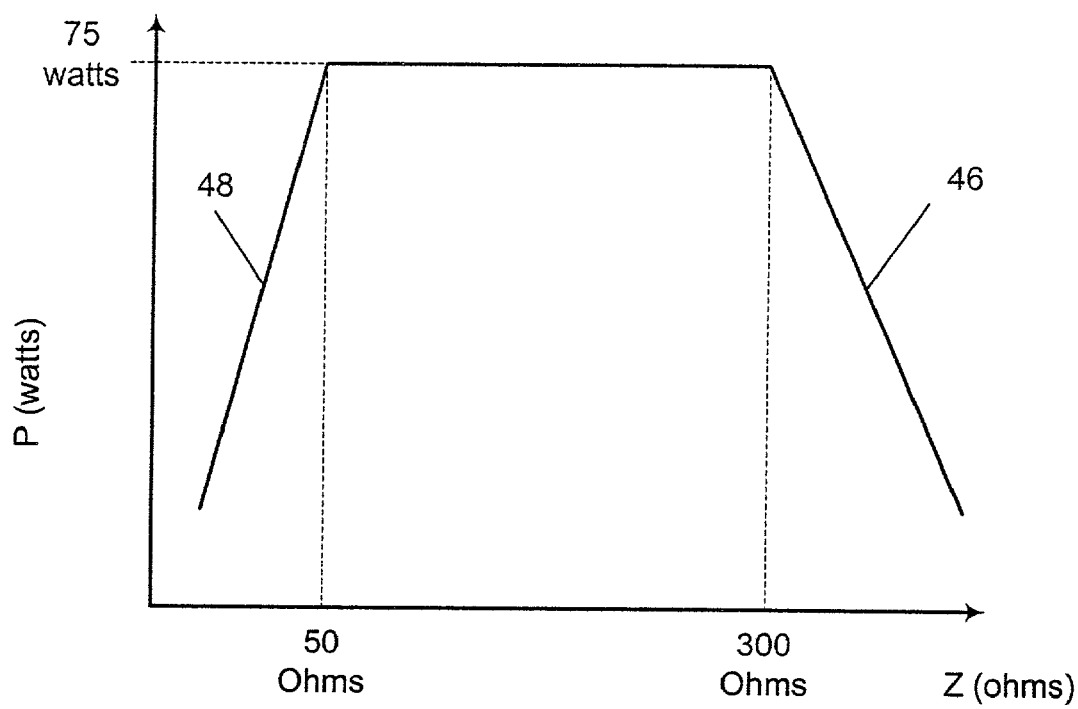
FIG. 5 is a schematic graph that describes the relationship of load impedance (Z, in ohms) and generator output power (P, in watts), for an exemplary generator output of 75 watts in a bipolar mode.

As discussed herein, RF energy delivery to tissue can be unpredictable and vary with time, even though the generator has been "set" to a fixed wattage. The schematic graph of FIG. 5 shows the general trends of the output curve of a typical general-purpose generator, with the output power changing as load (tissue plus cables) impedance Z changes. Load impedance Z (in ohms) is represented on the X-axis, and generator output power P (in watts) is represented on the Y-axis. In the illustrated embodiment, the electrosurgical power (RF) is set to 75 watts in a bipolar mode. As shown in the figure, the power will remain constant as it was set as long as the impedance Z stays between two cut-offs, low and high, of impedance, that is, for example, between 50 ohms and 300 ohms in the illustrated embodiment. Below load impedance Z of 50 ohms, the power P will decrease, as shown by the low impedance ramp 48. Above load impedance Z of 300 ohms, the power P will decrease, as shown by the high impedance ramp 46. Of particular interest to saline-enhanced electrosurgery is the low impedance cut-off (low impedance ramp 48), where power starts to ramp down as impedance Z drops further. This change in output is invisible to the user of the generator and not evident when the generator is in use, such as in an operating room.

Figure 6:
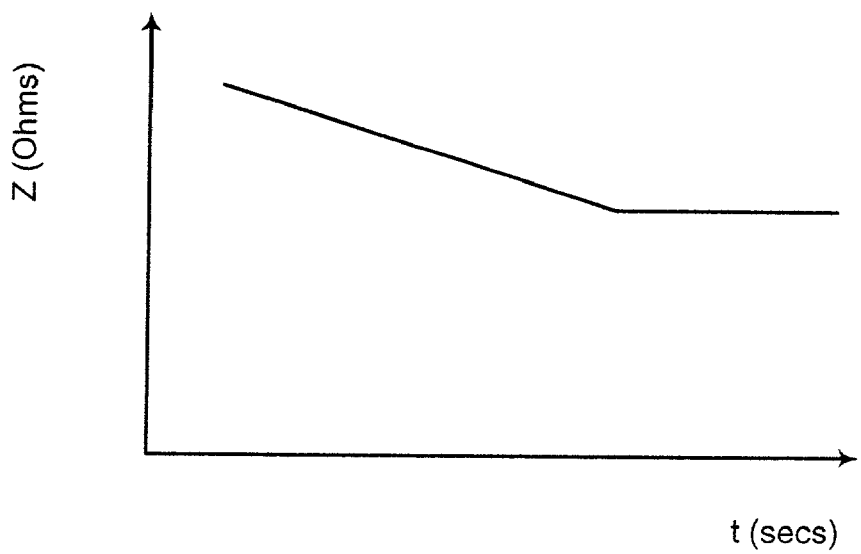
FIG. 6 is a schematic graph that describes the relationship of time (t, in seconds) and tissue impedance (Z, in ohms) after RF activation.

FIG. 6 shows the general trend of how tissue impedance generally changes with time for saline-enhanced electrosurgery. As tissue heats up, the temperature coefficient of the tissue and saline in the cells is such that the tissue impedance decreases until a steady-state temperature is reached upon which time the impedance remains constant. Thus, as tissue heats up, the load impedance Z decreases, potentially approaching the impedance Z cut-off of 50 ohms. If tissue is sufficiently heated, such that the low impedance cut-off is passed, the power P decreases along the lines of the low impedance ramp 48 of FIG. 5.

Combining the effects shown in FIG. 5 and FIG. 6, it becomes clear that when using a general-purpose generator set to a "fixed" power, the actual power delivered can change dramatically over time as tissue heats up and impedance drops. Looking at FIG. 5, if the impedance Z drops from 100 to 75 ohms over time, the power output would not change because the curve is "flat" in that region of impedances. If, however, the impedance Z drops from 75 to 30 ohms one would transgress the low impedance cut-off and "turn the corner" onto the low impedance ramp 48 portion of the curve and the power output would decrease dramatically.

According to one exemplary embodiment of the invention, the control device, such as flow rate controller 11, receives a signal indicating the drop in actual power delivered to the tissue and adjusts the flow rate Q of saline to maintain the tissue/electrode interface at a desired temperature. In a preferred embodiment, the drop in actual power P delivered is sensed by the power measurement device 8 (shown in FIG. 1), and the flow rate Q of saline is decreased by the flow rate controller 11 (also shown in FIG. 1). Preferably, this reduction in saline flow rate Q allows the tissue temperature to stay as hot as possible without desiccation. If the control device was not in operation and the flow rate Q allowed to remain higher, the tissue would be over-cooled at the lower power input. This would result in decreasing the temperature of the tissue at the treatment site.

The flow rate controller 11 of FIG. 1 can be a simple "hard-wired" analog or digital device that requires no programming by the user or the manufacturer. The flow rate controller 11 can alternatively include a processor, with or without a storage medium, in which the determination procedure is performed by software, hardware, or a combination thereof. In another embodiment, the flow rate controller 11 can include semi-programmable hardware configured, for example, using a hardware descriptive language, such as Verilog. In another embodiment, the flow rate controller 11 of FIG. 1 is a computer, microprocessor-driven controller with software embedded. In yet another embodiment, the flow rate controller 11 can include additional features, such as a delay mechanism, such as a timer, to automatically keep the saline flow on for several seconds after the RF is turned off to provide a post-coagulation cooling of the tissue or "quench," which can increase the strength of the tissue seal. Also, in another embodiment, the flow rate controller 11 can include a delay mechanism, such as a timer, to automatically turn on the saline flow several seconds before the RF is turned on to inhibit the possibility of undesirable effects as sticking, desiccation, smoke production and char formation. Also in another embodiment, the flow rate controller 11 can include a low level flow standby mechanism, such as a valve, which continues the saline flow at a standby flow level (which prevents the flow rate from going to zero when the RF power is turned off) below the surgical flow level ordinarily encountered during use of the electrosurgical device 5. As already discussed herein, the saline can act as a shunt and divert energy away from target tissue. This is a phenomenon that can only occur with a bipolar device. In a monopolar device, saline can "pool" in the treatment area, and can, in some situations, divert energy by pooling. However, before further discussion of a monopolar device and pooling, shunting in connection with a bipolar device will first be discussed.

In order to describe the underlying issue of saline shunting, an exemplary bipolar endoscopic electrosurgical device according to the present invention will be described in some detail. While the bipolar electrosurgical device of the present invention is described with reference to use with the remainder of the system of the invention, it should be understood that the description of the combination is for purposes of illustrating the remainder of the system of the invention only. Consequently, it should be understood that the bipolar electrosurgical device of the present invention can be used alone, or in conduction with the remainder of the system of the invention, or that, conversely, a wide variety of electrosurgical devices can be used in connection with the remainder of the system of the invention.

Preferably, the control device of the invention is used in connection with an electrosurgical device that is capable of controlling saline flow (for example, by controlling the location from which the saline is released from the electrosurgical device to the tissue). Any electrosurgical device that is capable of controlling saline flow is preferably used in connection with the invention described herein.

Figure 7:
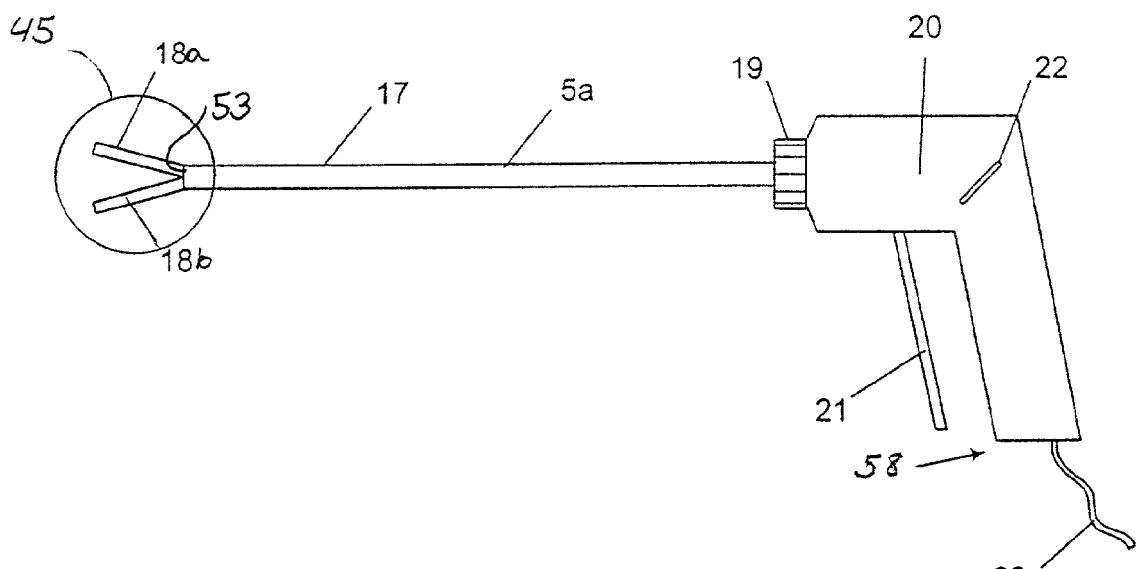
FIG. 7 is a schematic side view of one embodiment of a bipolar electrosurgical device.

FIG. 7 shows an overall simple side schematic view of one exemplary embodiment of an electrosurgical device 5a that is bipolar, and which is designed and configured to manipulate (e.g. grasp, coagulate and then cut) tissue. The electrosurgical device 5a preferably includes an intermediate segment comprising a hollow shaft 17, which is preferably connected to a tissue manipulator preferably comprising two opposing cooperating jaws 18a, 18b located at the distal tip or end 53 of the shaft 17. The electrosurgical device 5a also preferably includes a collar 19 for rotating the entire shaft 17, and connecting a proximal handle 20 at the proximal end of the shaft 17, an actuation mechanism 66 preferably comprising an actuation lever 21 and more preferably comprising a first-class lever (i.e. a lever with the fulcrum between the input force and the output force) which when squeezed will close the opposing jaws 18a, 18b, a pair of paddles 22 to activate the built-in cutting mechanism 31 (not shown in the figure), and a cable 23 attached to and extending from the handle 20 that contains two electrical wires and one fluid channel which extend from the jaws 18a, 18b through the shaft 17 and handle 20 (not shown individually in the figure).

Figure 7A:
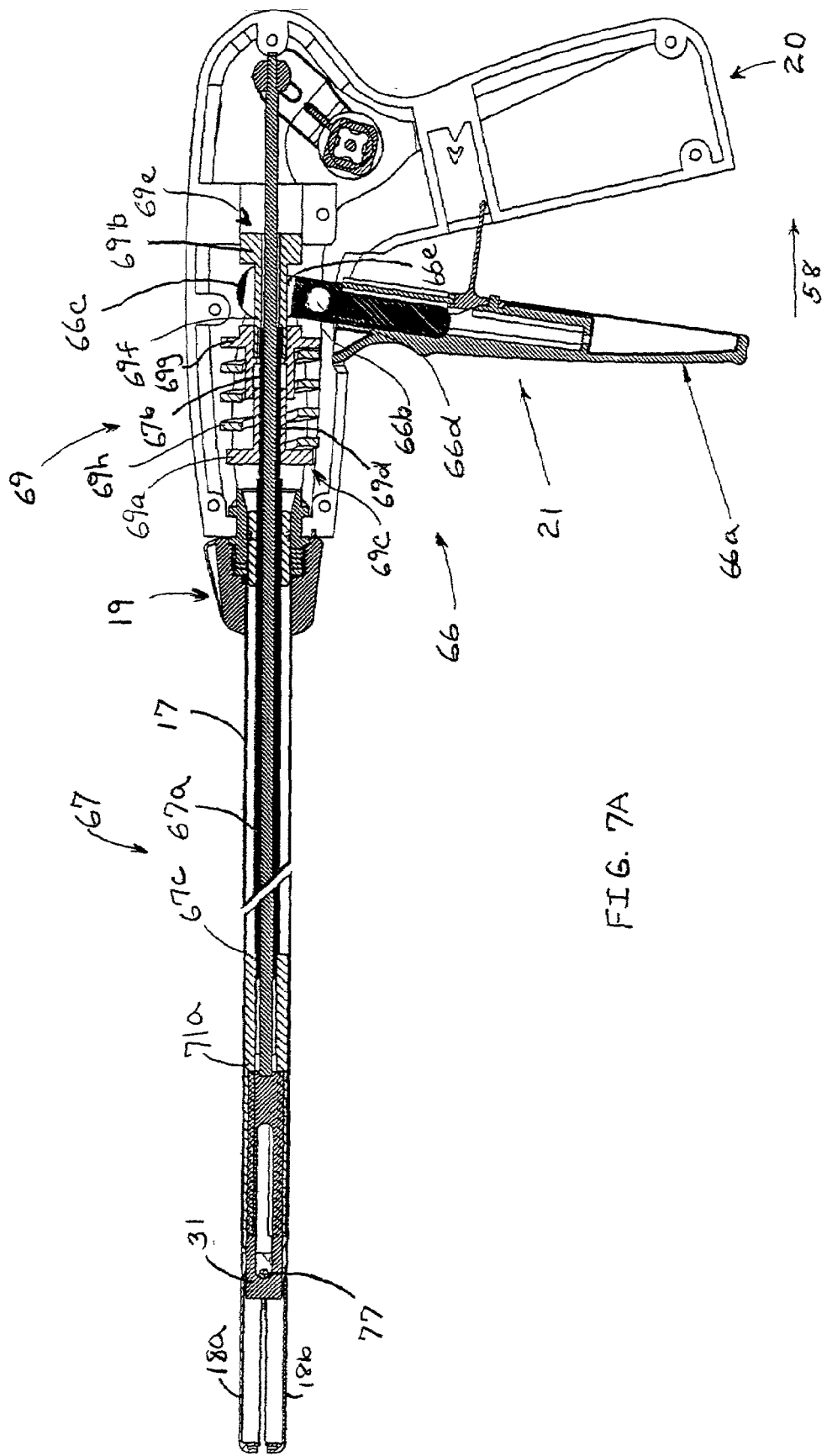
FIG. 7A is schematic section side view of one embodiment of a bipolar electrosurgical device.

In use, tissue to be treated is positioned between the jaws 18a, 18b of the device 5a. As shown in FIG. 7A, the hand grip portion 66a of the actuation lever 21 is then moved in direction of arrow 58 and squeezed towards the handle 20 causing the lever 21 to rotate about a fixed axis or rotation provided by a pivot 66b, and also causing the head portion 66c of the lever 21 to move distally. Preferably, the actuation lever 21 is held about the pivot by a fixing mechanism comprising a pin 66d extending through aligned holes in the actuation lever 21 and each side of the handle 20. The lever 21, is coupled, preferably mechanically, to an actuator 67 (i.e. a device which operates another device, in this case the jaws 18a, 18b) which receives an input from the actuation mechanism 66, here output displacement and/or force, from lever 21, and operates the jaws 18a, 18b.

More particularly, the actuator 67 preferably comprises a hollow elongated member 67a mechanically coupled at the proximal end to the actuation lever 21 by an actuation mechanism connector 69. The actuation mechanism connector 69 preferably comprises a spool configuration comprising a fixed distal flange 69a and a fixed proximal flange 69b separated by a spindle there between. As explained below, the distal flange 69a and the proximal flange 69b are fixed relative to the hollow elongation member 67a.

Preferably, the spool comprises a two piece configuration with a distal spool portion 69c comprising the distal flange 69a and a first portion of the spindle 69d and the proximal spool portion 69e comprising the proximal flange 69b and the second portion of the spindle 69f. Preferably, the distal spool portion 69c comprising the distal flange 69a and a first portion of the spindle 69d comprise a unitary piece, while the proximal spool portion 69e comprising the proximal flange 69b and the second portion of the spindle 69f also comprise a unitary piece.

Preferably both the distal portion of the spool 69c and the proximal portion of the spool 69e are fixed relative to the hollow elongated member 67a by being threaded over the proximal end 67b of the hollow elongated member 67a with internal threads for each hollow spool portion 69c, 69e threadedly engaging external threads on the hollow elongated member 67a. However, in other embodiments, at least a portion of the actuation mechanism connector 69 (e.g. spool) may be unitarily formed with the actuator 67, particularly elongated member 67a, or the actuation mechanism connector 69 may be connected to the elongated member 67a by, but not limited to welding, pining or press fitting.

Spindle 69d, 69f also preferably supports a movable flange 69g thereon which slides along at least a portion of the spindle 69d, 69f. As shown in FIG. 7A, preferably a force manipulating member 69h, preferably comprising a coil compression spring, is located between the distal flange 69a and the movable flange 69g. Also as shown in FIG. 7A, preferably, the head portion 66c of the lever 21 is configured to mechanically couple with the actuation mechanism connector 69 by a yoke structure including two substantially parallel tabs 66e extending on both sides of the spindle portion which engage the movable flange 69g and the proximal flange 69b. This structure of head portion 66c and actuation mechanism connector 69 advantageously allows for the pivotable engagement of head portion 66c with actuation mechanism connector 69.

The distal end of the hollow elongated member portion of the actuator is preferably mechanically coupled to jaws 18a, 18b by a tissue manipulator connector 71. The actuator 67, and more particularly elongated member 67a, and the tissue manipulator connector 71 may comprise a unitarily formed piece, or the tissue manipulator connector 71 may be connected to the elongated member 67a by, but not limited to welding, threaded engagement, pining or press fitting.

Preferably, the tissue manipulator connector 71 comprises a bar portion 71a extending distally and parallel from the distal end 67c of the elongated member 67a and a pivot pin portion 71b which extends from the bar portion 71a and perpendicular to the distal end 67c of the elongated member 67a.

Figure 8:
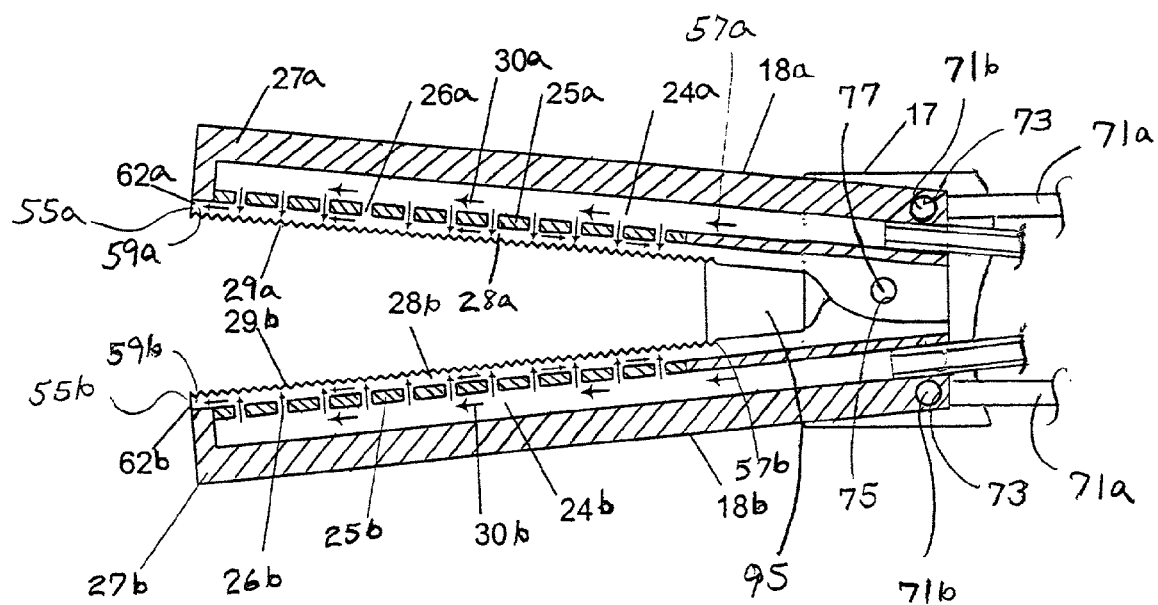
FIG. 8 is a schematic close-up section side view of the tip of the device bounded by circle shown in FIG. 7 and taken along line 8—8 of FIG. 10.

As shown in FIG. 8, the pivot pin portion 71b of the tissue manipulator connector 71 for each jaw 18a, 18b preferably extends into a moving pivot hole 73, with the axis of rotation for each moving pivot hole 73 configured parallel and of equal distance from the axis of rotation for a common fixed pivot hole 75 for each jaw 18a, 18b, the position of which is preferably being fixed by a pin 77 extending through the aligned holes in the jaws 18a, 18b and each opposite sides of shaft 17.

For the above configuration, the mechanical advantage of the actuation lever is preferably in the range between and including 4:1 (i.e. 4 to 1) to 10:1. In other words, when a force of 25 lbf (111 Newtons) is applied to the hand grip portion 66a of the actuation lever 21, the force which may be exerted on the movable flange 69g by head portion 66c is typically in the range between and including 100 lbf (445 Newtons) to 250 lbf (1112 Newtons).

With use of the above configuration, as the head portion 66c of the lever 21 moves distally from its extended or rest position, by virtue of the kinematics associated with substantially rigid mechanical components and couplings, the tabs 66e on the head portion 66c of the actuation lever 21 engage the movable flange 69g, which displaces portions of the actuation mechanism connector 69, the actuator 67, and the tissue manipulator connectors 71 distally, and beings closing the jaws 18a, 18b, by moving pivot pin 71b in pivot hole 73 radially around fixed pivot pin 77 in fixed pivot hole 75.

When compressible tissue is placed within the borders or confines of the jaws 18a, 18b, as the jaws 18a, 18b close the resistance to closure placed on the jaws 18a, 18b by the tissue increases as the tissue compresses. In other words, the more the tissue is compressed, the greater the resistance to compression. While a certain amount of compression force of the tissue is desirable to seal the blood vessels of the tissue being treated, it is equally desirable not to place so much force on the tissue such that the blood vessels are split prior to treatment.

In light of the above, in configuring the operation of the tissue manipulator operating mechanism for opening and closing jaws 18a, 18b as outlined above, a target force range was first established for the force to applied to the jaws 18a, 18b at the moving pivot holes 73 by the distal movement of the mechanism. In order to provide enough force perpendicular to the surfaces 29a, 29b of the jaws 18a, 18b at the distal ends 55a, 55b thereof for sealing, but without splitting tissue, an exemplary target force range for the force to applied to the jaws 18a, 18b at each of the moving pivot holes 73 was about 65 lbf (289 Newtons) per hole to 90 lbf (400.3 Newtons).

In order to achieve the above, preferably force manipulating member 69h comprises a coil compression spring which is preloaded to a exemplary first predetermined compression force of about 130 lbf (578.3 Newtons) and increases to a exemplary second predetermined compression force of about 180 lbf (800.7 Newtons) over an exemplary linear travel distance of the mechanism of about 3 mm.

As indicated above, as lever 21 travels distally from a first position, such as its extended or rest position, towards a second position, such as a latched position, the tissue manipulator operating mechanism described above is configured to correspondingly travel distally and close the jaws 18a, 18b. One advantage of the aforementioned mechanism is that prior to the attaining of the first predetermined compression force (e.g. preload of the spring), the operating mechanism behaves in a substantially rigid manner and exhibits a force versus displacement curve with a steep slope. In other words, the force increases quickly for a given displacement of the mechanism. Consequently, the tissue manipulator operating mechanism may attain the first predetermined compression force, and get into the target force range, with minimal distal travel of the tissue manipulator operating mechanism.

However, once the first predetermined compression force is attained, it is desirable to decrease the rate at which the force is further increased in order to attain the second (e.g. latched) position of the lever 21 prior to the force increasing beyond the second predetermined compression force. Thus, in the range between the first predetermined force and the second predetermined force, the rate of increase in the force is decreased as compared to the range between no force and the first predetermined force.

In the distal direction, the tissue manipulator operating mechanism draws the opposing jaws 18a, 18b toward each other, to close the jaws 18a, 18b on the tissue. However, when the actuation lever 21 is released, preferably the compression spring 69h, which compresses during closing of the jaws 18a, 18b, decompresses to apply an opening force of the jaws 18a, 18b and force the elongated member 67a and actuation lever 21 back to their jaw open position. Preferably, the elongated member 67a acts on the jaws 18a, 18b such that they open and close independently.

In other embodiments, the actuator may comprise, but is not limited to, other mechanical actuators or actuators such as electromechanical actuators, hydraulic actuators or pneumatic actuators (e.g. solenoids, motors, hydraulic pistons pneumatic pistons which may be coupled to the actuation mechanism and/or the tissue manipulator including, but not limited to, electrically, electromechanically, hydraulically or pneumatically. In one electromechanical embodiments, the actuation mechanism may comprise an electrical switch, the input from the actuation mechanism may comprise electric current and the actuation mechanism connector may comprise a wire conductor.

Once the jaws 18a, 18b of the tissue manipulator are closed, RF energy and conductive fluid, such as saline, are then applied through the device 5a and to the treatment site, thereby heating the tissue to coagulate, or achieve the desired treatment of the tissue. If desired, after coagulating the tissue between the jaws 18a, 18b, the jaws 18a, 18b can be held clamped together and the cutting mechanism 31 can be actuated to cut tissue.

FIG. 8 shows a schematic close-up section view of the two jaws 18a, 18b at the distal tip or end 45 of the electrosurgical device 5a at the distal end 53 of the shaft 17. In a preferred embodiment, each jaw 18a, 18b includes energy-providing member, such as an electrode 25a, 25b. In the embodiment of FIG. 8, the energy-providing member shown is an elongated U-shaped energy-providing member with an elongated U-shaped manifold 24a, 24b located beneath at least a portion of the energy-providing element, and at least one, and more preferably, plurality of circular through holes or other fluid outlets 26a, 26b provided through the electrode 25a, 25b. Each jaw 18a, 18b further includes a tissue manipulating jaw surface 29a, 29b that contacts the tissue to be treated. In the embodiment illustrated in FIG. 8, the jaw surface 29a, 29b is textured, so that it is capable of grasping the tissue to be treated. However, the jaw surface 29a, 29b need not be textured, and can include any type of desired surface configuration, such as serrations and the like, or can be provided with a smooth surface. In use, saline flows in a manifold 24a, 24b (i.e. passage) in the direction of arrows 30a, 30b, wherein the manifold 24a, 24b preferably distributes saline flow relatively evenly (i.e., relatively uniformly) to a plurality of spaced holes 26a, 26b, generally uniformly spaced, along the length of the electrode 25a, 25b that are made in the electrode 25a, 25b of the jaw 18a, 18b. Preferably, electrode 25a, 25b comprises an electrically conductive metal, which is preferably non-corrosive, such as stainless steel or titanium. Holes 26a, 26b of this exemplary embodiment preferably have a diameter in the range between and including about 0.10 mm to 2.0 mm and more preferably have a diameter in the range between and including about 0.15 mm to 0.020 mm.

Preferably, at least a portion (e.g. the portion of the jaw 18a, 18b in direct contact with the electrode 25a, 25b and the conductive fluid in the manifold 24a, 24b) and, more preferably, most, if not all, of the structural material of each jaw 18a, 18b comprises and is fabricated from a material that is non-conductive electrically. More preferably, the material comprises a non-conductive polymer such as polyamide (a/k/a nylon), polyphthalamide (PPA), polyamideimide (PAI), polyetherimide (PEI), polyetheretherketone (PEEK), polyphenylenesulfide (PPS), polysulfone (PSO), polyethersulfone (PES), syndiotactic polystyrene (SPS), polyimide (PI) or any other non-conductive polymer, thermoplastic or thermoset. Even more preferably, the polymer comprises a liquid crystal polymer and, more particularly, an aromatic liquid crystal polyester which is reinforced with glass fiber, such as Vectra® A130 from Ticona, 90 Morris Avenue, Summit, N.J. 07901-3914. This non-conductive material, or insulator, is shown in the figure as reference number 27a, 27b, and provides a combined housing for retaining the electrode 25a, 25b and forming a portion of the manifold 24a, 24b. Further, in some embodiments, the other portions of the jaw 18a, 18b such as jaw surface 29a, 29b can comprise and be fabricated from a non-conductive material.

In other embodiments, the non-conductive material of the jaw 18a, 18b may comprise a non-conductive coating over an electrically conductive material. For example, the non-conductive coating may comprise a polymer coating applied over an underlying metal, which is preferably non-corrosive, such as stainless steel or titanium.

In a preferred embodiment, each jaw 18a, 18b further includes a U-shaped groove 28a, 28b that is recessed as to form a recess from the jaw tissue-manipulating surface 29a, 29b to provide a fluid flow channel. In this embodiment, after the saline flows through the fluid exit holes 26a, 26b from the manifold 24a, 24b, it flows in the groove 28a, 28b. When tissue is grasped or otherwise manipulated between the jaws, saline can flow in the groove 28a, 28b between the electrode 25a, 25b and the tissue, and exit through at least one exit groove 62a, 62b that are open to the outside. Preferably, the electrode 25a, 25b comprises at least a portion of the bottom wasll of the groove 28a, 28b. Where groove 28a, 28b is not used, electrode 25a, 25b may be level with and comprise at least a portion of jaw surface 29a, 29b, or may protrude relative to jaw surface 29a, 29b, or may completely comprise jaw surface 29a, 29b.

Figure 10:
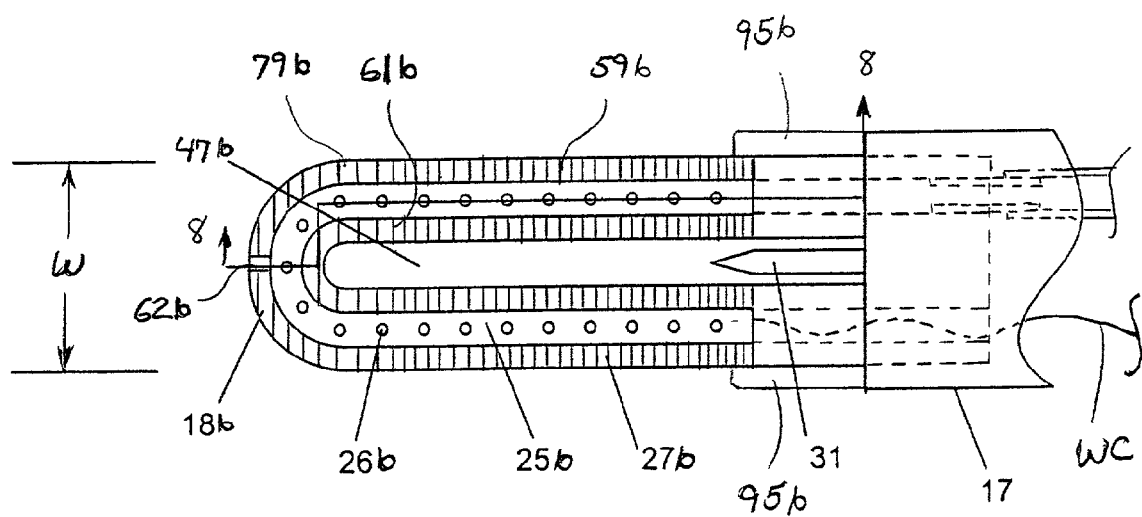
FIG. 10 is a schematic close-up section top view of the tip of the device bounded by circle 45 shown in FIG. 9 with jaw 18*a* removed.

As shown in FIGS. 8 and 10, the fluid exit is formed in the portion of the jaw 18a, 18b forming the outer wall 59a, 59b of the exit groove 62a, 62b and is located at the distal end 55a, 55b of the jaws 18a, 18b. However, in other embodiments, the fluid exit may be formed at any location along the length of the outer wall 59a, 59b, or may be formed in the portion of the jaw 18a, 18b forming the inner wall 61a, 61b of the exit groove 62a, 62b. Also as shown in FIG. 10, a sensor, such as a temperature sensor, pressure sensor or saline impedance sensor for sensing the phase change associated with the onset of boiling may be located in outer wall 59a, 59b. adjacent the electrode 25a, 25b and/or the tissue.

Figure 9:
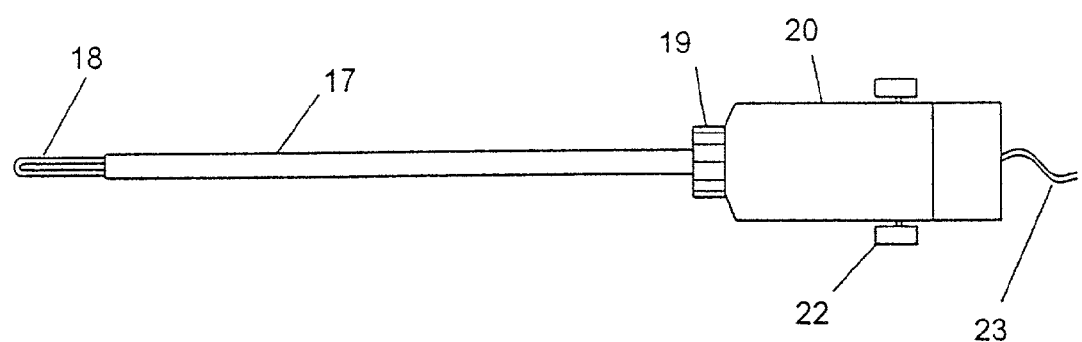
FIG. 9 is a schematic top view of the bipolar electrosurgical device shown in FIG. 7.

FIG. 9 shows an overall schematic top view of the electrosurgical device 5a shown in FIGS. 7 and 8. Preferably, as shown in FIG. 9, the jaws 18a, 18b can be provided in a U-shaped loop configuration. In other words, the jaws 18a, 18b can be formed such that the manifolds 24a, 24b, electrodes 25a, 25b, and/or grooves 28a, 28b initially extend away from the proximal ends 57a, 57b of the jaws 18a, 18b towards the distal ends 55a, 55b of the jaws 18a, 18b, then return from the distal ends 55a, 55b of the jaws 18a, 18b towards the proximal ends 57a, 57b of the jaws 18a, 18b to form a U-shaped configuration.

FIG. 10 shows a close-up section top view of one of the loop jaws 18b of the tip 45 of the electrosurgical device 5a. In this embodiment, the jaws 18a, 18b are provided in a loop configuration to create a space 47a, 47b that allows a cutting mechanism 31 to move proximally and distally within the space 47a, 47b. One can comprehend that the electrode configuration shown in FIG. 9 is simply an exemplary configuration, and the electrode need not be formed of two loops. For example, the electrosurgical device need not include a cutting mechanism, and the electrodes in these embodiments would not be required to include a space or recess for passage of the cutting mechanism. The invention contemplates any suitable electrode configuration which may be used to treat tissue, particularly with RF energy and conductive fluid.

As shown in FIG. 10, jaws 18a, 18b includes at least one tissue stop 95a, 95b. In use, tissue stop 95a, 95b inhibits tissue from extending within the confines of the jaw 18a, 18b proximally past the end of electrode 25a, 25b where it may not be treated.

Preferably jaws 18a, 18b comprise an interchangeable configuration such that to jaws 18a, 18b comprises the same components and can be used one for the other to reduce manufacturing costs and assembly complexity. However, in other embodiments, jaws 18a, 18b may comprise different components and configurations.

As indicated above, electrodes 25a, 25b of electrosurgical device 5a are preferably electrically coupled to generator 6 via wire conductors of cable 9 contained in handle 20. More specifically, one wire conductor, connected to electrode 25a, for example, comprises the positive terminal while the other wire conductor, connected to electrode 25b, for example comprises the negative terminal. The wire conductors WC are conductively attached, preferably via silver solder, to the electrodes 25a, 25b at one end of the U-shaped configuration as shown in FIG. 10.

Figure 11:
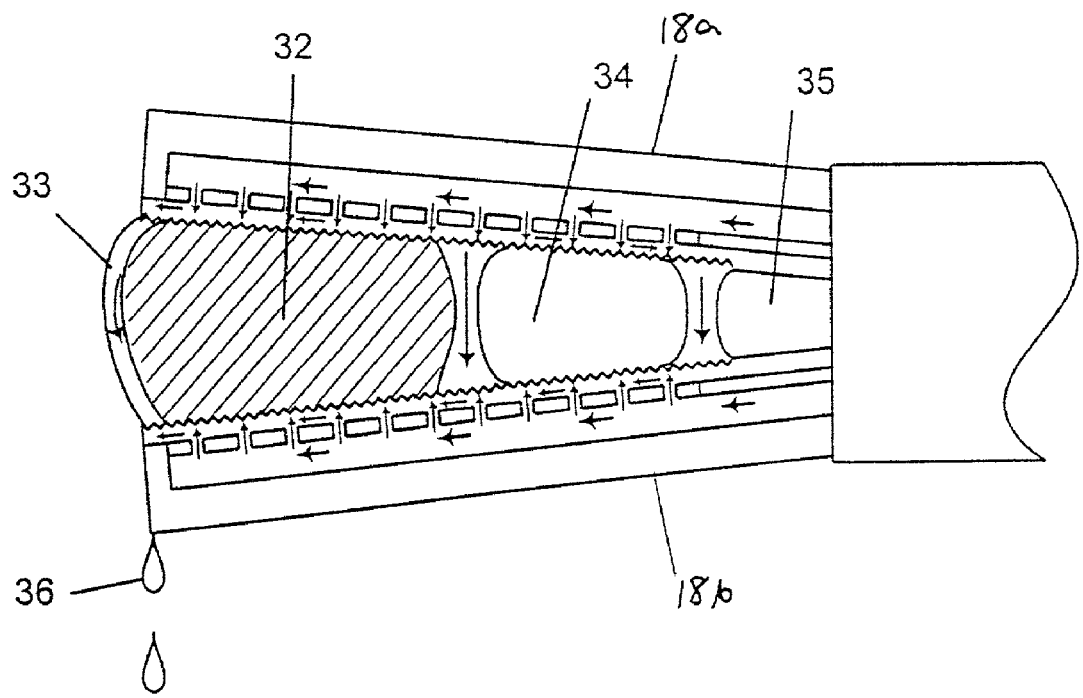
FIG. 11 is a schematic close-up section side view of the electrodes of the device shown in FIG. 9 showing saline shunting without boiling of the saline.

If the saline that flows from one electrode 25a to the other electrode 25b, for example, is not boiling in any significant manner (e.g. saline temperature below the boiling temperature), a large fraction of the RF energy can be diverted away from target tissue. This "stealing" of RF energy tends to dramatically slow down the process of coagulating tissue and producing the desired hemostasis or aerostasis of the tissue. This situation is illustrated in FIG. 11. In this embodiment, tissue 32 grasped between the jaws 18a, 18b only partially occupies the jaw surface 29a, 29b and does not fill the jaws 18a, 18b. Areas 34 and 35 show areas of air between the jaws 18a, 18b. Depending on orientation of the electrosurgical device 5a, saline liquid may flow from the top electrode jaw 18a to the lower electrode jaw 18b in several locations, for example, at area 33, located at the distal end 55a, 55b of the jaws 18a, 18b. Saline liquid may also flow from the top electrode jaw 18a to the lower electrode jaw 18b at locations between the distal end 55a, 55b and proximal end 57a, 57b of the jaws 18a, 18b and in contact with the proximal end of the tissue 32 (relative to the user of the electrosurgical device 5a), for example, at locations between tissue 32 and area 34. Saline liquid may also flow from the top electrode jaw 18a to the lower electrode jaw 18b at locations adjacent the proximal end 57a, 57b of the jaws 18a, 18b and removed (i.e. not in contact) with the proximal end of the tissue 32, for example, at locations between areas 34 and 35. These locations of saline flow between areas 34 and 35 represent the closest gap between jaws (area 35) and flow of saline along the tissue boundary 32, which are the most likely areas for saline flow between the jaws 18a, 18b. Since most of the saline is not boiled, excess saline 36 drips off the lower jaw.

Figure 11A:
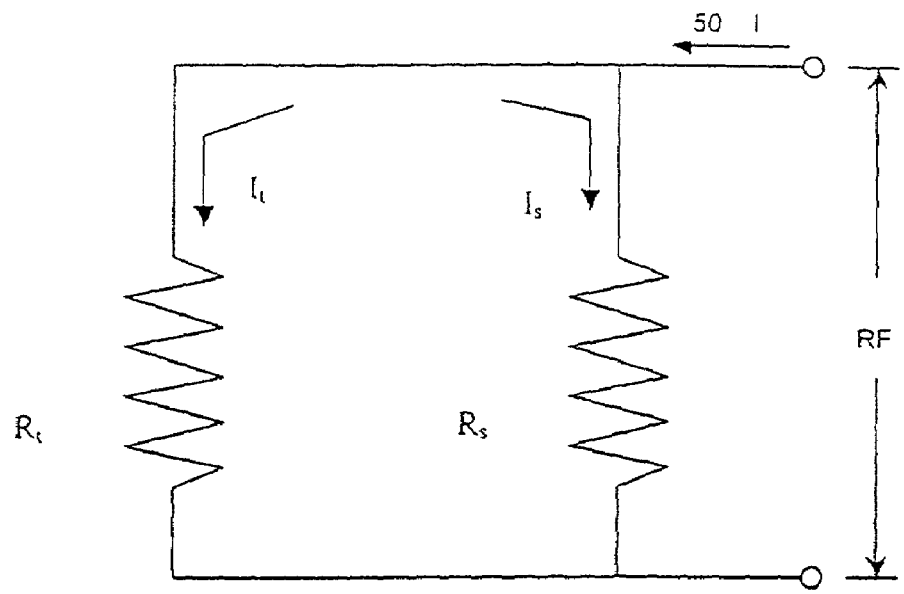
FIG. 11*a* is a diagram that describes the equivalent electrical circuit for tissue in parallel with a single saline shunt.

The saline shunting scenario can also be explained by using an electrical circuit as shown in FIG. 11a. Electrically, the tissue and the saline fluid shunt can be modeled as resistors in parallel. Using Ohm's Law one can calculate the percentage of total RF power that is dissipated in the saline shunt as:

$$\% \ RF \ \text{Power} = \frac{100}{[1 + R_s / R_t]}$$

Figure 11B:
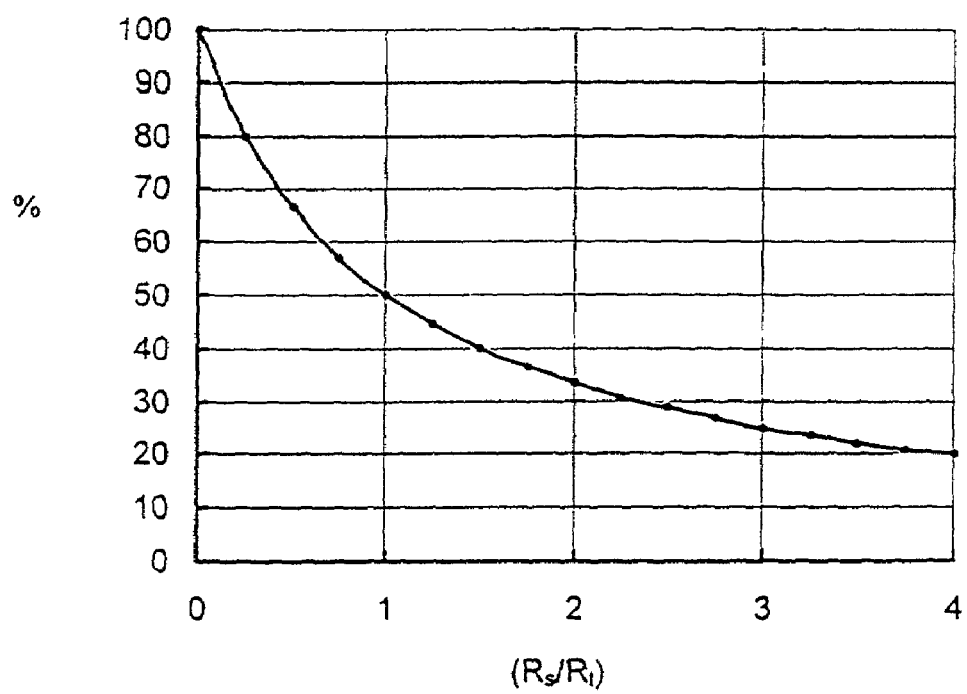
FIG. 11*b* is a graph that describes the relationship of ratio of saline to tissue resistance ($R_s/R_t$) and percent power shunted into saline.

In the embodiment illustrated in FIG. 11a, the total current (I) 50 from source 54 is split between two resistors, tissue electrical resistance ($R_t$), and saline shunt electrical resistance ($R_s$). This relationship is shown in the schematic graph of FIG. 11b, which shows the relationship of the ratio of saline to tissue resistance ($R_s/R_t$) (X-axis) to percent of power shunted into saline (Y-axis). As shown in the figure, when the resistance of the saline is equal to the tissue ($R_s/R_t$=1), half the power is shunted into the saline. For example, when the resistance of the saline is four times that of the tissue, then only 20% of the power is shunted into the saline.

Figure 12:
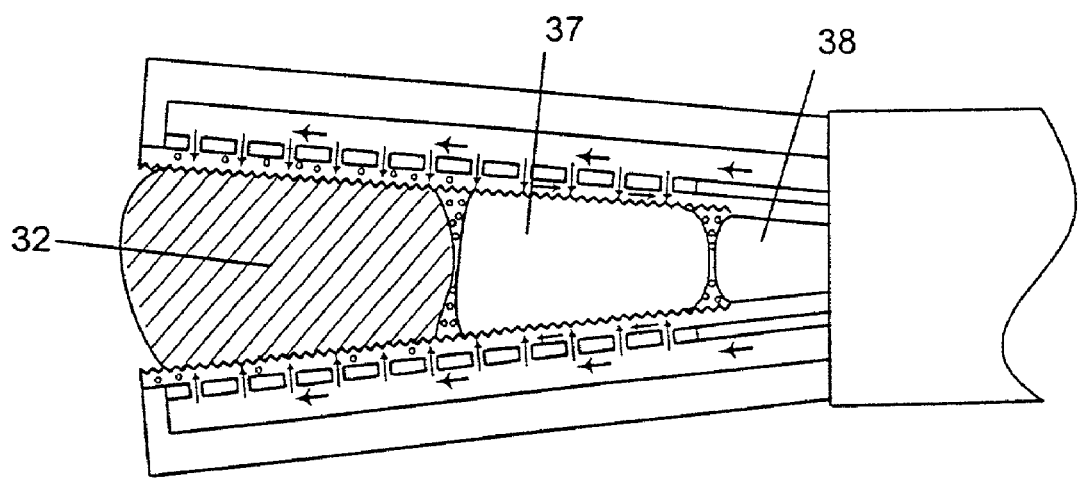
FIG. 12 is a schematic close-up side section view of the electrodes of the device shown in FIG. 9 showing a large percentage of the saline boiling at the tissue treatment site.

One benefit of the flow rate control strategy previously described herein, where a high % boiling is maintained, is that the flow of saline from, for example, one electrode 25a to the other electrode 25b is either eliminated altogether because all the flow boils off at the electrode/tissue interface between the electrode and the tissue, or a large fraction of the flow boils as it flows toward the other electrode. This second case is illustrated in FIG. 12, that is, where a large fraction of the saline flow boils as it flows toward the other electrode. Note that in comparison to FIG. 11, there is less saline flowing from the top jaw 18a to the lower jaw 18b, and where there is flow it is actively boiling, as indicated by the vapor bubbles shown in several locations 37 and 38. According to the invention, boiling of a large fraction of the saline assures that most of the RF power will be directed into the tissue to achieve coagulation in the fastest time. Stated another way, another control strategy of the present invention is to reduce the presence of a saline shunt by increasing the % boiling of the saline.

Another aspect of the control strategy of the invention is that the flow of saline is preferably primarily directed spatially against or very near the target tissue 32 that is to receive the RF power. If the flow rate is not near where the RF power is turned into heat, the saline is not capable of protecting the tissue 32 from desiccation by dissipating excess heat in the boiling process. Therefore, in a preferred embodiment, the flow of conductive fluid is directly primarily at the tissue treatment site.

Figure 13:
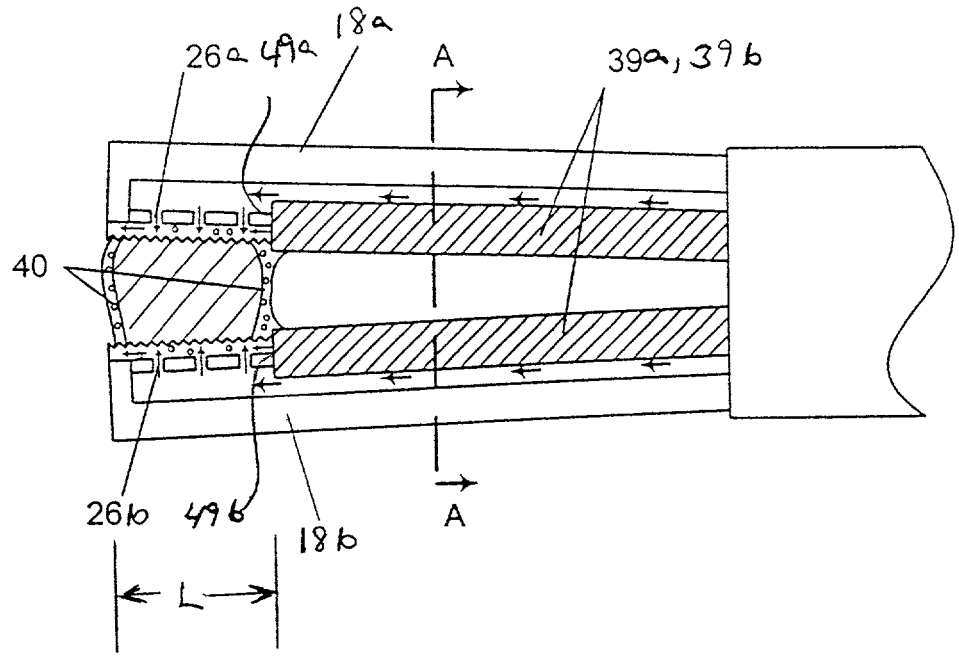
FIG. 13 is a schematic close-up side section view of electrodes of the device shown in FIG. 9 showing two gutters slid out to direct saline flow distally toward tissue.

With use of the electrosurgical device 5a, typically a surgeon will grasp a small amount of tissue 32 with the very tip 45 of the device 5a as shown in FIG. 13. If the electrode jaws 18a, 13b are long relative to the length of the tissue segment being grasped, resulting in tissue 32 being grasped only adjacent the distal ends 55a, 55b of the jaws 18a, 18b, then saline exiting of holes 26a, 26b in the middle and adjacent the proximal end 57a, 57b parts of the jaws 18a, 18b may not be able to flow towards the distal end 55a of the tip 45, but may leak out along the upper jaw 18a. Though surface tension of the upper surface 47 (i.e. facing the tissue) of the electrode 25a and the geometry of the groove 28a will act to keep saline flow in the groove 28a, gravity can tend to cause the saline which has collected to overcoming the effects of surface tension and flow down directly to the opposing jaw 18b. This would result in the undesirable effects mentioned above.

In another exemplary embodiment of the invention, by providing two slidable gutters 39a, 39b, the flow of saline can be collected and directed distally toward the tissue 32. In this embodiment, the saline can flow from one jaw 18a to the other jaw 18b in areas 33, located on each side of the tissue being grasped, but with a large percentage boiling before reaching the other jaw. According to this embodiment, the gutters 39a, 39b can be fabricated from any material that is non-conducting, for example, such as the plastic and plastic coated metals which may be used for the jaws 18a, 18b described above. The gutters 39a, 39b can slide toward the distal end 55a, 55b of the device 5a as part of the activation of lever 21 shown in FIG. 7, to be stopped automatically by the presence of tissue. Alternatively the gutters 39a, 39b can be slid forward towards the distal ends 55a, 55b as part of a separate mechanism action for moving the gutters 39a, 39b proximally and distally, such as with a spring. In other words, a spring may be provided which, in the decompression direction, distally moves the gutters 39a, 39b towards the distal ends 55a, 55b of the jaws 18a, 18b to cover the electrodes 25a, 25b. Conversely, in the compression direction of the spring, the presence of the tissue 32 biases the spring and proximally moves the gutters 39a, 39b towards the proximal ends 57a, 57b of the jaws 18a, 18b. The gutters 39a, 39b can be fabricated from any suitable material that is non-conducting, for example, plastic.

Figure 14:
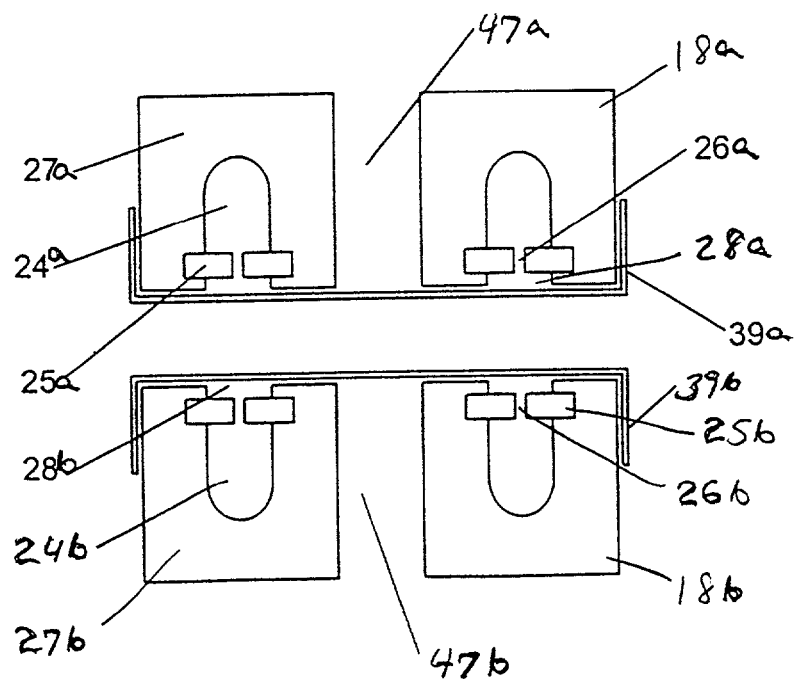
FIG. 14 is a schematic close-up cross-section view along line A—A of FIG. 13, showing the two gutters positioned to collect and direct saline flow distally.

FIG. 14 shows a schematic cross-sectional view of the gutters shown in FIG. 13. The cross-section in FIG. 14 illustrates the nonconducting portion 27a, 27b of the jaw 18a, 18b, the saline manifold 24a, 24b, the electrodes 25a, 25b, holes 26a, 26b, groove 28a, 28b, space 47a, 47b for the cutting mechanism 31, and gutters 39a, 39b. Near the distal end 49a, 49b of the gutters 39a, 39b, exit grooves 62a, 62b in the jaw 18a, 18b can allow saline to flow through and onto the edge of the tissue 32 even if the gutter 39a, 39b is pressed snuggly against the tissue 32 (shown in FIG. 8).

Figure 15:
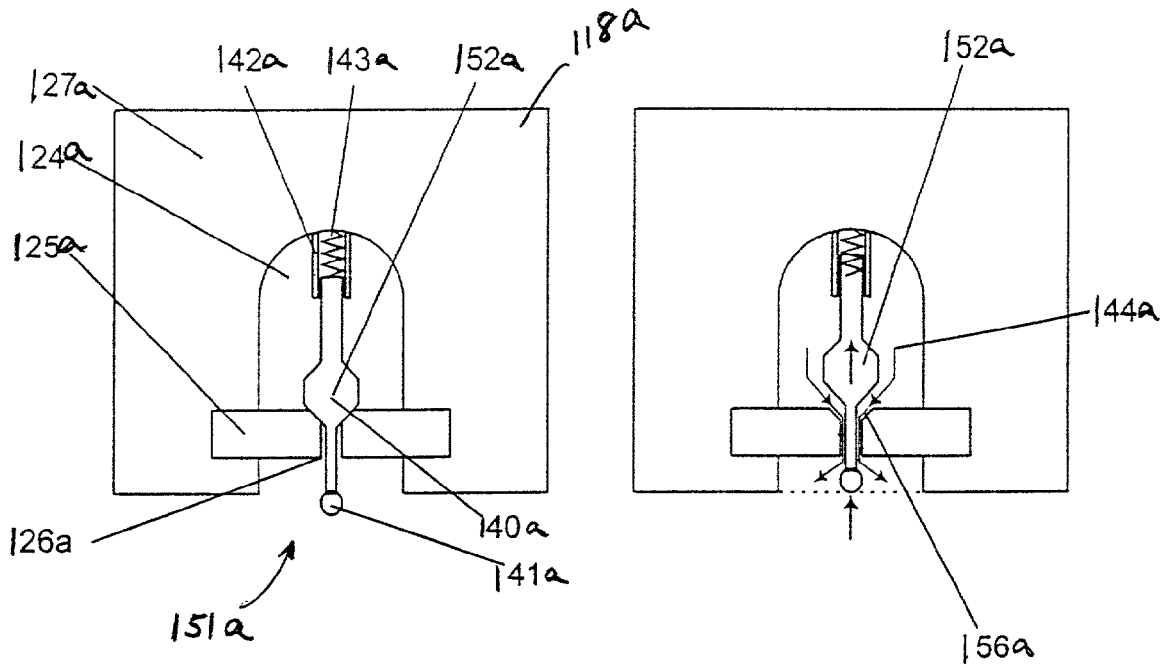
FIG. 15 is a schematic close-up cross-section view of one embodiment of the jaws of the device shown in FIG. 9, wherein the jaws include a tissue-activated valve.
Figure 16:
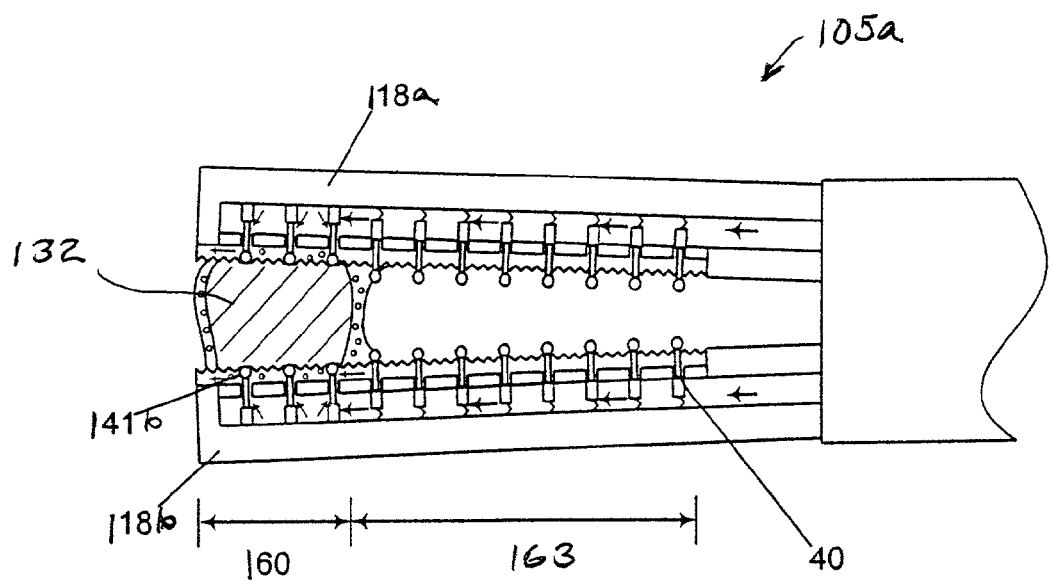
FIG. 16 is a schematic close-up side section view of one embodiment of the jaws of the device shown in FIG. 9, wherein the jaws include tissue-activated valves to direct flow distally.

FIG. 15 and FIG. 16 illustrate an alternative embodiment of the electrosurgical device of the invention. In this embodiment, similar to the preceding embodiment, the electrosurgical device also includes a mechanism for directing saline flow to where tissue is being heated using RF energy and providing a saline application mechanism which limits the application of saline to the area of the jaws 118a, 118b as directed by the presence of the tissue 132. Preferably, the mechanism for directing saline flow comprises one or more tissue activated valves 151a, 151b. In FIG. 15, the jaw 118a, 118b of the device 105a includes a pin 140a, 140b that is configured with a bulged portion 152a, 152b in the middle section of the plunger pin 140a, 140b, so that the pin 140a, 140b can seat into a counter-sunk hole 126a, 126b in the electrode 125a, 125b. Pin 140a, 140b preferably further includes a pin tip 141a, 141b that contacts tissue. Preferably, the pin tip 141a, 141b is rounded or atraumatic (i.e., blunt) to reduce tissue trauma. As illustrated in the figure, counter-sunk hole 126a, 126b includes a recessed portion 156a, 156b that is configured to receive the bulged portion 152a, 152b, such that when seated within the recessed portion 156a, 156b, the pin 140a, 140b inhibits conductive fluid flow from the manifold 124a, 124b to the tissue being treated. Preferably, a guide tube 142a, 142b holds the pin 140a, 140b in position, and spring 143a, 143b provides decompression force to push the bulged portion 152a, 152b of pin 140a, 140b into the recessed portion 156a, 156b and seal off the flow of saline from the manifold region 124a, 124b. In use, the pin tip 141a, 141b contacts tissue when the jaws 118a, 118b compress tissue. When tissue is compressed, the tissue contacts the tip 141a, 141b and overcomes the compression force of the spring 143a, 143b which pushes the pin 140a, 140b upwards, unseating the bulged portion 152a, 152b of the pin 140a, 140b from the recessed portion 156a, 156b, and allowing saline to flow in direction of arrows 144a, 144b through the annular space between the pin 140a, 140b and the counter-sunk hole 126a, 126b.

FIG. 16 shows a schematic view of one embodiment wherein a series of such tissue-activated valves 151a, 151b functions to deliver saline flow only to areas of the jaws 118a, 118b where tissue 132 is compressed and to be RF-heated. Referring to FIGS. 15 and 16, tissue 132 is compressed in the area labeled 160, and the holes 126a, 126b are open to allow saline flow to the tissue treatment site. As described above, tissue contacts tip 141a, 141b, thereby pushing pin 140a, 140b upwards, unseating the bulged portion 152a, 152b of the pin 140a, 140b from the recessed portion 156a, 156b (shown in FIG. 15). This interaction allows saline to flow from the device 105a to the tissue 132 being treated. In the area labeled 163 in the figure, tissue is not compressed between jaws 118a, 118b of the device 105a, and therefore the holes 126a, 126b are closed to the flow of saline from the device 105a. Because the tips 141a, 141b of pins 140a, 140b do not contact tissue 132, the pin 140a, 140b is not forced from its seated position within recessed portion 156a, 156b of the hole 126a, 126b (shown in FIG. 15).

In addition to providing a saline application mechanism which limits the application of saline to the area of the jaws as directed by the presence of the tissue, gutters 39a, 39b and pins 140a, 140b may provide an output related to the magnitude of a tissue within the jaws and, in doing so, be used as part of a mechanism to determine the dimensions, area or volume of the tissue located within the confines of the jaws.

It has been found that the volume of tissue within the confines of the jaws is directly related to, and may be correlated to, an estimated tissue treatment time period. Consequently, where the volume of tissue within the confines of the jaws is known, a predetermined treatment time period is also known from the established correlation. Consequently, during surgery, the actual tissue treatment time period may be compared to a predetermined tissue treatment time period, which is stored for example, in the memory of a microprocessor or on a printed table. Then, when the actual tissue treatment time period is determined to be equal to or greater than the predetermined tissue treatment time period, the user of the electrosurgical device is informed that the predetermined tissue treatment time period has been reached or exceeded, and can move to a new tissue treatment site.

In considering the width of the tissue within the confines of the jaw 18a, 18b, as shown in FIG. 10, the width W of the tissue can be approximated as being equal the width of the jaw 18a, 18b as, in a vast majority of instances, the tissue treatment site will span the width of the jaw 18a, 18b. An exemplary width W is about 8 mm or less.

In considering the length of the tissue 32 within the confines of the jaws 18a, 18b, as indicated above, the length L can be determined by comparing, for example, the location of the distal end 49a, 49b of gutter 39a, 39b relative to the distal end 55a, 55b of jaw 18a, 18b. When the distal end 49a, 49b of gutter 39a, 39b extends to the distal end 55a, 55b of jaw 18a, 18b, the tissue length within the confines is equal to zero. Then, as the distal end 49a, 49b of gutter 39a, 39b retracts proximally away from the distal end 55a, 55b of jaw 18a, 18b due to the interference of tissue 32, the linear displacement between the distal end 49a, 49b of gutter 39a, 39b and the distal end 55a, 55b of jaw 18a, 18b comprises the length L of the tissue 32. An exemplary length of tissue is about 30 mm or less.

The measurement of linear displacement between the distal end 49a, 49b of gutter 39a, 39b and the distal end 55a, 55b of jaw 18a, 18b may be correlated, preferably mechanically, to a measurement scale, such as a dimensional scale (e.g. ruler) or time scale preferably located on the device 5a, such as on the side of the gutter 39a, 39b or the jaw 18a, 18b or the handle. The measurement may be unitless or comprise an input for tissue dimension (e.g. length), tissue area or tissue volume. Alternatively, the linear displacement may be electromechanically correlated to a measurement scale by, for example, a linear sensor, such as a linear transducer, wherein an electrical output signal corresponding to linear displacement is stored in the memory of a microprocessor and manipulated by an algorithm to provide measurements of linear displacement.

Figure 13A:
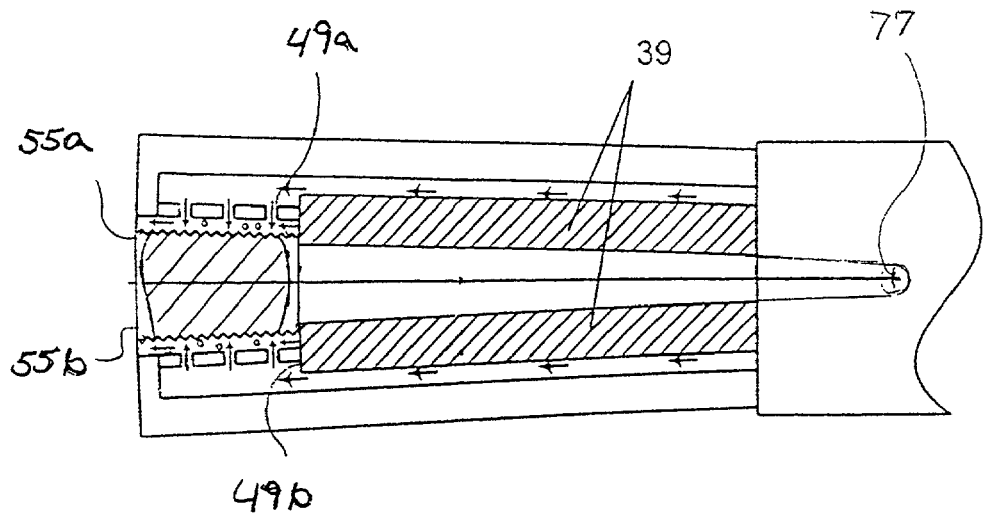
FIG. 13A is a schematic close-up side section view showing the gutters of FIG. 13 being used in conjunction with right triangles to determine the cross-sectional area of the tissue.

Once the length of the tissue 32 within the confines of the jaws 18a, 18b is known, the area of tissue within the confines of the jaws 18a, 18b and perpendicular to the jaw surfaces 29a, 29b may be determined via geometry as shown in FIG. 13A. More specifically, in the situation, for example, where jaws 18a, 18b are held about a common pivot, such as provided by pin 77, simple calculations involving the area of triangles may be performed to determine the area of tissue in question. For example, as shown in FIG. 8a, jaws 18a, 18b are preferably angularly positioned equally about the pivot's axis of rotation from their fully closed position forming a first upper and lower right triangles, each with a hypotenuse extending from the axis of rotation to the distal ends 55a, 55b of each of the jaws 18a, 18b. Within the area of each first upper triangle and first lower triangle are two smaller second upper and lower right triangles, each with a hypotenuse extending from the axis of rotation to the distal ends 49a, 49b of the gutters 39a, 39b. The area of the tissue within the confines of the jaws 18a, 18b can then be determined by subtracting the area of each of the second smaller upper and lower right triangles, which are void of tissue 32, from the area of each of the first larger upper and lower right triangles, respectively, with the remaining area representing the area of the tissue.

In order to determine the area of each of the first and second upper and lower right triangles as described above, preferably the length of each hypotenuse for each triangle is known along with the angular displacement of the jaws 18a, 18b from their fully closed position. With regards to the length of the hypotenuse for each of the first larger upper and lower triangles, the length of the hypotenuse is fixed by the length between the distal end 55a, 55b of jaw 18a, 18b and the pivot's axis of rotation, here, pin 77. An exemplary length is about 45 mm. With regards to the length of the hypotenuse for each of the first smaller upper and lower triangles, the length of each hypotenuse may be determined by subtracting the length of the tissue L as determined above from the length of hypotenuse for each of the first larger upper and lower triangles. As indicated above an exemplary length of tissue is about 30 mm. Consequently, where exemplary length of the hypotenuse for the first upper and lower triangles equals 45 mm, the length of the hypotenuse for each of the first smaller upper and lower triangles is about 15 mm (i.e. 45 mm−30 mm).

With regards to the angular displacement of the jaws 18a, 18b from their fully closed position, an exemplary angular displacement is about 6 degrees or less per jaw 18a, 18b. In an exemplary embodiment, jaws 18a, 18b are configured to provide an angular displacement of about 20 degrees per side, as in the case where both jaws 18a, 18b open and close, for a total angular displacement capability of about 40 degrees or less.

With an exemplary tissue length of 30 mm, an exemplary angular displacement of the jaws 18a, 18b of 6 degrees per side and an exemplary length between the distal end 55a, 55b of jaw 18a, 18b and the pivot's axis of rotation of 45 mm, the cross-sectional area of the tissue is estimated to comprise about 187 mm² (1.87 cm²). With regards to volume, with an exemplary jaw width of 8 mm, the volume of tissue within the confines of the jaws 18a, 18b comprises about 1496 mm³ (1.496 cm³).

Figure 17:
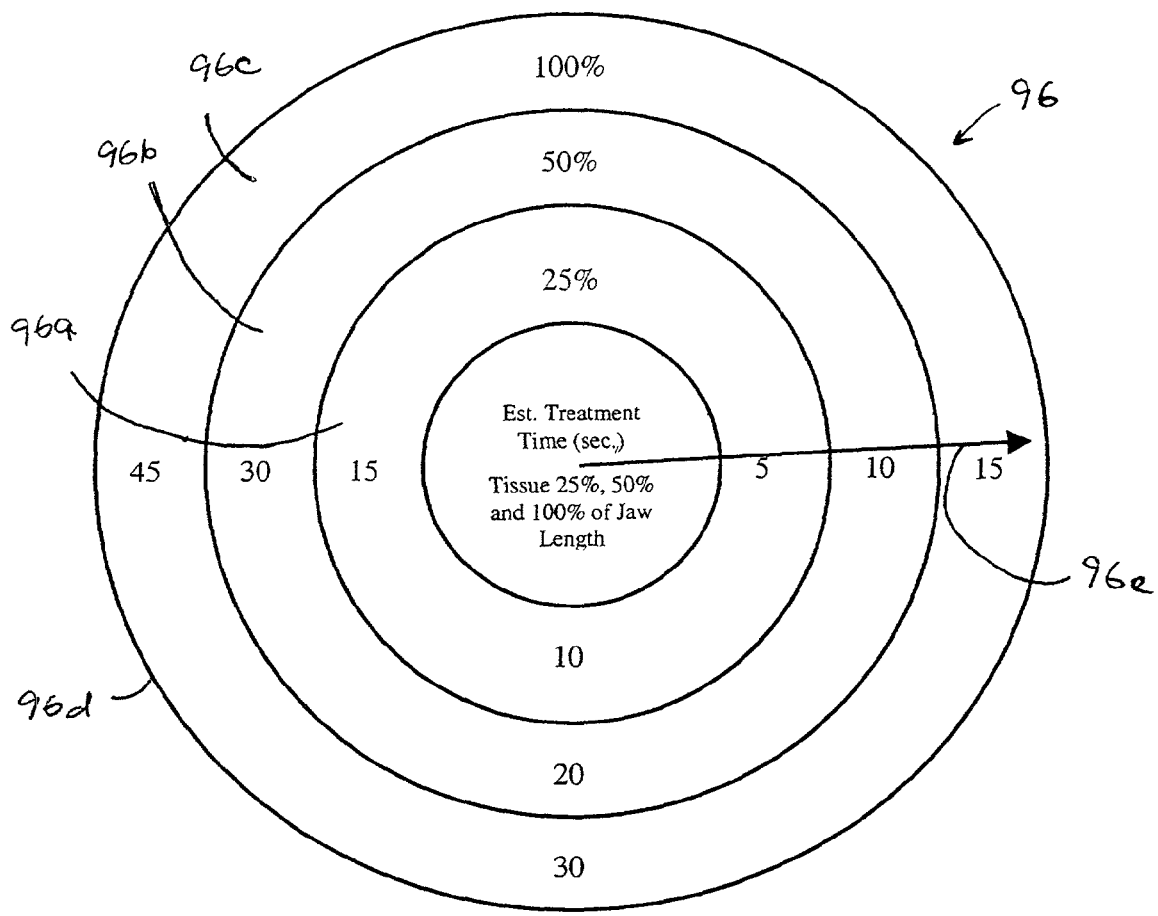
FIG. 17 is a close-up front view of a dial gauge which may be used with the electrosurgical device.

Given that jaws 18a, 18b are mechanically coupled to elongated member 67a, the angular position of the may be correlated to the linear distal displacement of elongated member. Thus, similar to gutters 39a, 39b, the linear displacement of the elongated member 67a may be correlated to a measurement scale. Furthermore, the measurement scale preferably considers both the length L of the tissue 32 and the angular position of the jaws. As shown in FIG. 17, in one exemplary embodiment the length L of tissue 32 within the confines of the jaws may be correlated to a percentage, such as 25%, 50% and 100% of jaw length, with the percentage readable or otherwise detectable, by the user of the device on the device, such as the side of the jaws 18a, 18b, for example. The given percentages may then be expressed in the form of concentric circles 96a–c forming a multi-dimensional dial scale 96d for a dial gauge 96 preferably located on the device. Thus, the a reading of the percentage of jaw length (which correlates to tissue length L) on the side of the jaws 18a, 18b may be directed correlated to one of the dial scales 96d on the device.

Figure 18:
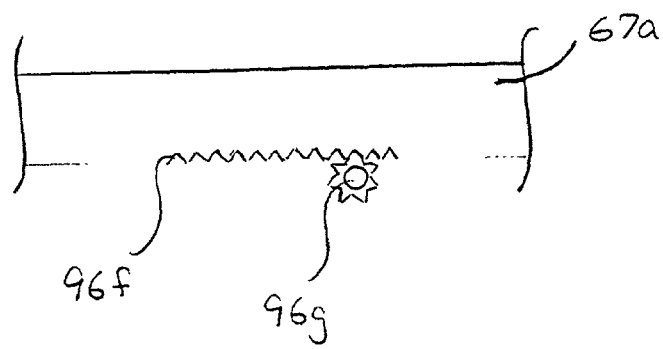
FIG. 18 is a side view of a rack and pinion which may be used to connect the dial gauge of FIG. 17 to the electrosurgical device.

With respect to the dial 96e of the dial gauge 96, the position of the dial 96e may be directly correlated to the position of the elongated member 67a (which is directly correlated to the angular position of the jaws 18a, 18b) via a rack and pinion. For example, as shown in FIG. 18, the rack 96f may be located on elongated member 67a which engages a pinion 96g to which dial 96e is connected. Thus, the displacement of elongated member 67a may be correlated to the position of the dial 96e of the dial gauge 96. Preferably, the dial scales 96d are correlated to an approximation of the time required to treat the tissue 32, rather than the volume of tissue within the confines of the jaws 18a, 18b. In this manner, the user of the device 5a may correlate the tissue treatment time approximated on the device 5a with an actual timing device, such as a clock, to establish when the actual time elapsed for tissue treatment time has met or exceeded the approximated tissue treatment time provided by the device 5a.

Figure 19:
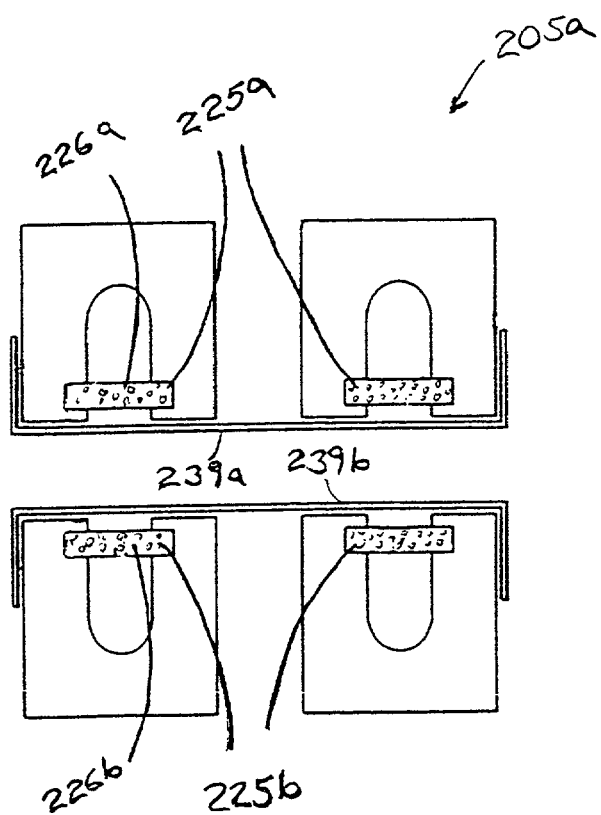
FIG. 19 is a schematic close-up cross-section view along line A—A of FIG. 13, showing and alternative form of the jaw.

Generally, substantially linear through holes 26a, 26b or 126a, 126b of the electrode 25a, 25b or 125a, 125b supply conductive fluid to the treatment site. However, in an alternative embodiment, as shown in FIG. 19, these holes are provided in the form of porous material such as metal. In this embodiment, the electrodes 225a, 225b preferably do not include discrete substantially linear holes through a solid non-porous material; rather, the electrode 225a, 225b and the electrode surface itself are made porous by a tortuous path to allow infusion of the conductive solution to the treatment site. Porous sintered metal is available in many materials (such as, for example, 316L stainless steel, titanium, Ni-Chrome, and the like) and shapes (such as cylinders, discs, plugs, and the like) from companies such as Porvair, located in Henderson, N.C.

Porous metal components can be formed by a sintered metal powder process or by injection molding a two-part combination of metal and a material that can be burned off to form pores that connect (open cell) to each other. With sintering, for example, typically solid particles of material are placed in a mold under heat and pressure such that the outer surface of the particles soften and bond to one another with the pores comprising the interstices between the particles. Alternatively, when porosity is formed by burning off material, it is not the interstice between the particles which provides the porosity as with sintering, but rather a partial evisceration of the material generally provided by the removal of a component with a lower melt temperature than the burn off temperature.

In this embodiment, conductive fluid will flow out of the electrode 225a, 225b everywhere the pores are open. Preferably, the exterior (that is, the portions of the components 225a, 225b that do not comprise the portion of the device 205a involved in tissue treatment) of such porous metal electrode components 225a, 225b can be covered with a material, such as a polymer coating, that fills the pores and inhibits both the flow of saline and the passing of electrical energy. Alternatively, the device 205a can include gutters 239a, 239b to inhibit the flow of saline in areas where it is desired to inhibit saline flow.

In yet another embodiment, a porous polymer is used in place of the porous metal. Although the polymer is generally non-conductive, the conductive solution provided will conduct the RF energy across the porous polymer wall and to the tissue to be treated. Suitable materials include high temperature open cell silicone foam and porous polycarbonates, among others. Different from sintering or evisceration of material, formation of porosity in open cell polymer foams is typically accomplished by the introduction of gas bubbles, either chemically or physically, into the polymer during its formation or melt phase which form a cellular structure. However, sintering or evisceration of material may also be used with polymer materials.

Porous ceramics also generally fall into the category of being non-conductive, since they could distribute conductive fluid flow, withstand high temperatures and be machinable or moldable for manufacturing purposes. Preferably, the material used transmits both fluid flow and electrical energy; thus, materials with properties between high-electrical conductivity metals and low electrical conductivity polymers are also contemplated, such as porous carbon-filled polymers. In these embodiments, conductive fluid flow is distributed along the length of the electrodes, where porous material is used to fabricate the electrodes. All or a portion of the electrodes can be porous according to the invention.

Preferably the holes 226a, 226b in the porous material have a pore size (cross-sectional dimension) in the range between and including about 2.5 micrometers (0.0025 mm) to 500 micrometers (0.5 mm) and more preferably has pore size in the range between and including about 10 micrometers (0.01 mm) to 120 micrometers (0.12 mm). Even more preferably, the porous material has a pore size in the range between and including about 20 micrometers (0.02 mm) to 80 micrometers (0.08 mm).

Figure 20:
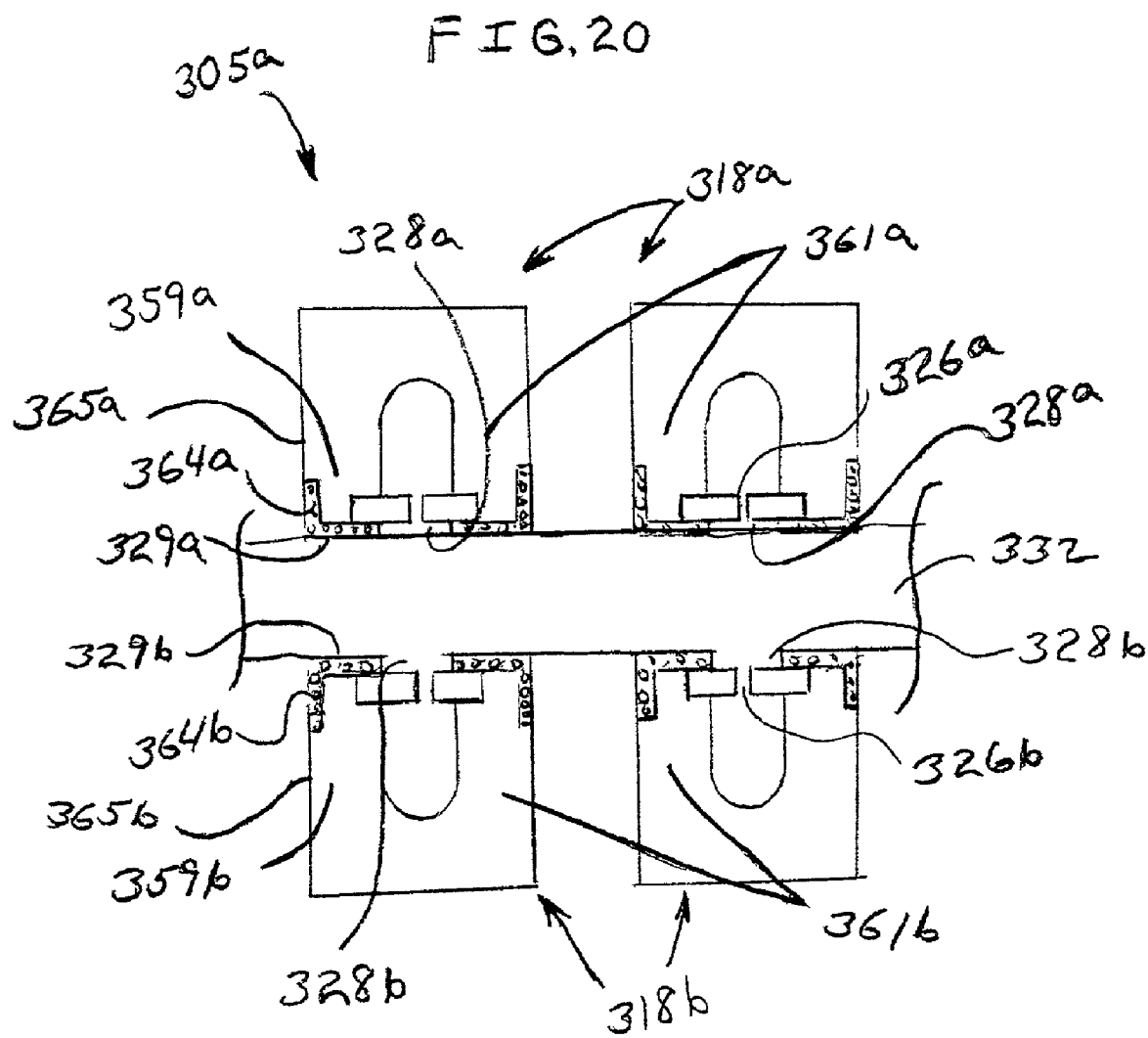
FIG. 20 is a schematic close-up cross-section view along line A—A of FIG. 13, showing and alternative form of the jaw.

As discussed above, exit grooves 62a, 62b of jaws 18a, 18b provide a fluid exit from the jaws 18a, 18b that is open to the outside of the jaws 18a, 18b. In an alternative embodiment, rather than discrete openings, the fluid exits from the jaws may be provided in the form of a porous structure as part of, for example, a porous material (such as metal, polymer or ceramic discussed above). For example, as shown in FIG. 20, preferably a least a wall portion 364a, 364b of the outer wall 359a, 359b of jaw 318a, 318b of device 305a may comprise the porous material. As shown, porous material of outer wall 364a, 364b has an inlet surface which comprises a side surface of the fluid flow channel provided by recess 328a, 328b and an outlet surface 356a, 365b which comprises a non-tissue-manipulating surface. Furthermore, the porous material also preferably comprises an additional fluid outlet surface comprising a tissue-manipulating surface 329a, 329b. The inlet surface and the outlet surface are connected by a plurality of tortuous paths in the porous material.

As shown, the porous material preferably terminates on the non-tissue-manipulating surface 365a, 365b distally away or remote from the tissue treatment site and tissue 332 such that the porous material fluid outlet surfaces may only partially be in contact with tissue 332 (i.e. tissue-manipulating surface 329a, 329b is in contact with tissue 332). If the complete fluid outlet surfaces of the porous material are in contact and become covered by tissue 332 with use, the pores of the porous material may become obstructed and no longer function as exits for fluid. As shown wall portion 364a, 364b also comprises at least a portion of the jaw surface 329a, 329b in contact with tissue 332 during treatment thereof. Also as shown, the porous material may at least partially overlie the electrode 325a as shown by jaw 318a. Also alternatively as shown, the porous material may comprise a least a wall portion of the inner wall 361a, 361b of jaw 318a, 318b of device 305a.

Preferably the porous material provides for the wicking (i.e. drawing in of fluid by capillary action or capillarity) of the fluid into the pores of the porous material. In order to promote wicking of the fluid into the pores of the porous material, preferably the porous member also comprises a hydrophilic material, which may be provided, for example, by the porous material itself with or without post treating (e.g. plasma surface treatment such as hypercleaning, etching or micro-roughening, plasma surface modification of the molecular structure, surface chemical activation or crosslinking), or by a coating provided thereto, such as a surfactant.

In addition to providing a more uniform distribution of fluid exits in the jaw 318a, 318b, the porous material of wall portion 364a, 364b also provides other advantages. For example, discrete openings such as exit groove 62a, 62b are difficult to mold or machine below a size of 0.276 millimeters (0.007 inches). Conversely, the porous material may provide exits of a smaller dimension. Furthermore, once exit groove 62a, 62b becomes filled with fluid, a surface tension flow barrier may be created by the fluid within the exit groove 62a inhibiting flow of additional fluid. Conversely, fluid may be conveyed in the porous material and away from groove 28a, 28b by wicking as described above.

In addition to providing exits for fluid along the outer surface 365a, 365b of the outer wall 359a, 359b, and outside the confines of the jaw 318a, 318b, the porous material also provides exits for fluid on jaw surfaces 329a, 329b which grasp or otherwise manipulate tissue 332. Consequently, because heated and/or electrified fluid can now be provided to jaw surface 329a, 329b, heat and/or electric current which may flow though the fluid (in the case of a conductive fluid) results in a wider tissue sealing region as compared to when the jaw surfaces do not dissipate fluid.

In addition to the above, when jaw surfaces 329a, 329b in contact with tissue 332 dissipate fluid, tissue 332 is less apt to stick to the jaw surfaces as compared to the situation where the jaw surfaces do not dissipate fluid. Furthermore, the roughness of the porous material may reduce the need for serrations of the jaw surface 329a, 329b (and the associated tissue damage) to adequately grasp the tissue 332.

Preferably, the wall portion 364a, 364b is joined to the remainder of the jaw 318a, 318b by an adhesive. Preferably, the adhesive comprises a thermoset polymer, and more preferably a thermoset one-component epoxy adhesive from Engineered Material Systems Inc. of Delaware Ohio sold under the designation EMS 502-09. In other embodiments, the adhesive may comprise a thermoplastic polymer. In still other embodiments wall portion 364a, 364b may be joined to the remainder of the jaw 318a, 318b by methods of joining other than adhesive bonding with a separate adhesive. For example, wall portion 364a, 364b may be autogenicly bonded to the remainder of the jaw 318a, 318b. In other words, bonded where the bonding substance comprises the material of the wall portion 364a, 364b and/or jaw 318a, 318b themselves, as apposed to the use of separate materials such as adhesives.

In order to achieve autogenic bonding of the wall portion 364a, 364b with the jaw 318a, 318b, preferably an interface (e.g. contact location) between the two materials is subjected to heat and pressure. By application of heat and pressure to the wall portion 364a, 364b and/or jaw 318a, 318b, at least the surface portion of the wall portion 364a, 364b and/or jaw 318a, 318b subjected to the heat softens and/or melts to give it adhesive properties. Typically, a thin layer of polymer melt (where at least one of the wall 364 of jaw 318 comprises a polymer) on at least one of the surfaces to be joined is created, at which time the wall portion 364a, 364b and jaw 318a, 318b may be pressed together. This material is subsequently cooled and bonds the surfaces, at which time the clamping force removed.

The above description may be more appropriately characterized as thermal autogenic bonding. In other words, autogenic bonding is achieved by the application of heat to at least one of the items to be bonded. Furthermore, the temperature at which thermal autogenic bonding occurs may be referred to as the "thermal autogenic bonding temperature".

Autogenic bonding may also be performed without heat, for example, by means of a suitable solvent applied to the item(s) to be bonded which "soften" the bonding surface. Adhesion is attained by evaporation of the solvent, absorption of it into adjacent material, and/or diffusion of liquefied polymer molecules or chain segments across the interface.

In addition to adhesive and autogenic bonding, it should be understood that joining of the wall portion 364a, 364b and jaw 318a, 318b may be accomplished by any suitable method, autogenic or not, such as, but not limited to, vibration welding, ultrasonic welding, high-frequency welding, electromagnetic welding, induction welding, friction welding, hot-gas welding, hot-plate welding, heat staking, adhesive bonding, or mechanical fastening, such as with mechanical fasteners comprising screws.

In describing the control strategy in relation for the electrosurgical devices of the present invention described thus far, focus has been drawn to a steady state condition. However, the heat required to warm the tissue to the peak temperature (T) may be incorporated into equation (1) as follows:

$$P = \Delta T/R + \rho c_p Q_1 \Delta T + \rho Q_t h_v + \rho c_p V \Delta T/\Delta t \quad (4)$$

where $\rho c_p V \Delta T/\Delta t$ represents the heat required to warm the tissue to the peak temperature (T) 68 and where:

$\rho$=Density of the saline fluid that gets hot but does not boil (approximately 1.0 gm/cm$^3$);

$c_p$=Specific heat of the saline (approximately 4.1 watt-sec/gm-° C.);

V=Volume of treated tissue $\Delta T = (T - T_\infty)$ the difference in temperature between the peak tissue temperature (T) and the normal temperature ($T_\infty$) of the body tissue (°C.). Normal temperature of the body tissue is generally 37° C.; and $\Delta t = (t - t_\infty)$ the difference in time to achieve peak tissue temperature (T) and the normal temperature ($T_\infty$) of the body tissue (° C.).

With an electrosurgical device such as 5a, when tissue 32 completely occupies the jaw surfaces 29a, 29b and the jaws 18a, 18b are closed into a typical use position, exemplary dimensions for length, width, and thickness of the tissue 32 which may be treated within the confines of jaws 18a, 18b may be approximated by 3 cm, 0.6 cm and 0.2 cm, respectively. As a result, the volume V of treated tissue can be approximated to 0.36 cm$^3$.

Through experimentation, it has been found that with an electrosurgical device 5a the time to heat the tissue to 100° C. from 37° C. is approximately 10 seconds. Thus, the heat required to warm the tissue to the peak temperature (T) 68 is equal to (1) (4.1) (0.36) (100−37)/(10)=9.3 watts. The inclusion of the heat required to warm the tissue to the peak temperature (T) in the control strategy is graphically represented at 68 in FIG. 2A.

With respect to the control strategy, the effects of the heat required to warm the tissue to the peak temperature (T) 68 should be taken into account before flow rate Q adjustment being undertaken to detect the location of the line of onset of boiling 76. In other words, the flow rate Q should not be decreased in response to a lack of boiling before at least a quasi-steady state has been achieved as the location of the line of onset of boiling 76 will continue to move during the transitory period. Otherwise, if the flow rate Q is decreased during the transitory period, it may be possible to decrease the flow Q to a point past the line of onset of boiling 76 and continue past the 100% boiling line 80 which is undesirable. In other words, as temperature (T) is approached the heat 68 diminishes towards zero such that the lines of constant boiling shift to the left towards the Y-axis.

Figure 28:
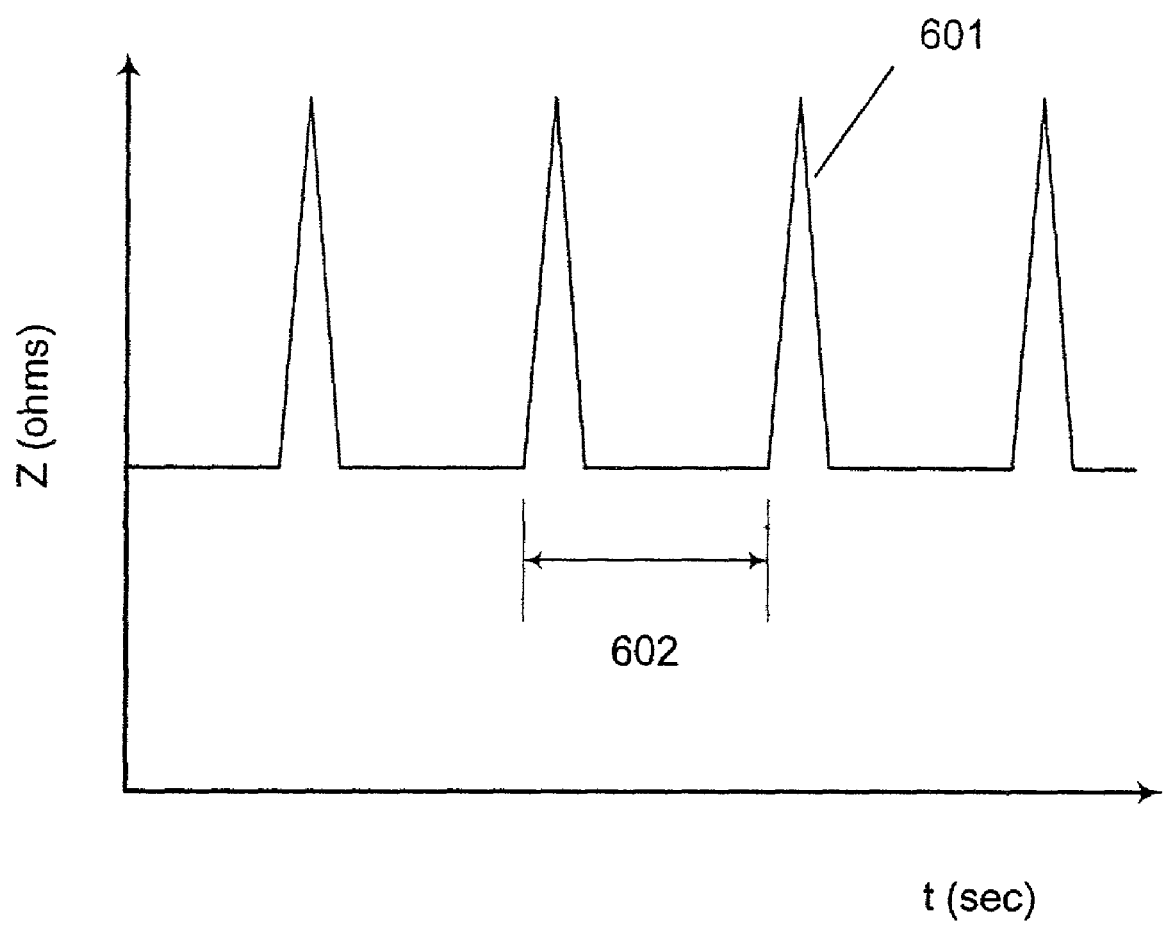
FIG. 28 is a schematic graph of impedance Z versus time t showing changes in impedance represented by impedance spikes.

Another means to detect boiling in a device is to detect changes in the electrical impedance that occur as a result of the presence of vapor at the electrode/tissue interface. When the jaws of a bipolar device are fully clamped on tissue and boiling occurs in the recess (e.g. 28a, 28b of FIG. 8) the resulting vapor escapes toward exits 62a, 62b. As the vapor moves along the recesses, 28a, 28b, toward the exits 62a, 62b the vapor may disrupt the conduction of electrical energy from the electrodes 26a, 26b, through the conductive fluid to the tissue 32. Once the electrical pathway is broken, with the conductive fluid acting as a liquid "fuse", the RF energy and heating to the tissue 32 is turned off, the tissue cools, boiling stops, and liquid conductive fluid once again flows into the recesses 28a, 28b. However, if the conditions are right for boiling, it will occur once again, and repeatedly. This periodic boiling and venting of vapor has been observed experimentally, and is represented as shown in FIG. 28, as a plot of impedance Z versus time t. The impedance spikes 601 shown in FIG. 28 occur at a frequency of about 1 cycle per second and with an amplitude that is on the same order as the baseline impedance. This frequency is shown in FIG. 28 as the interval 602 between successive impedance spikes. Impedance is directly measurable by dividing the voltage by the current as previously described. The use of electrical impedance to detect the onset of tissue dessication when impedance rises dramatically as a result of being heated to the point of smoking and charring, but not to detect the presence of boiling, is described above.

Figure 29:
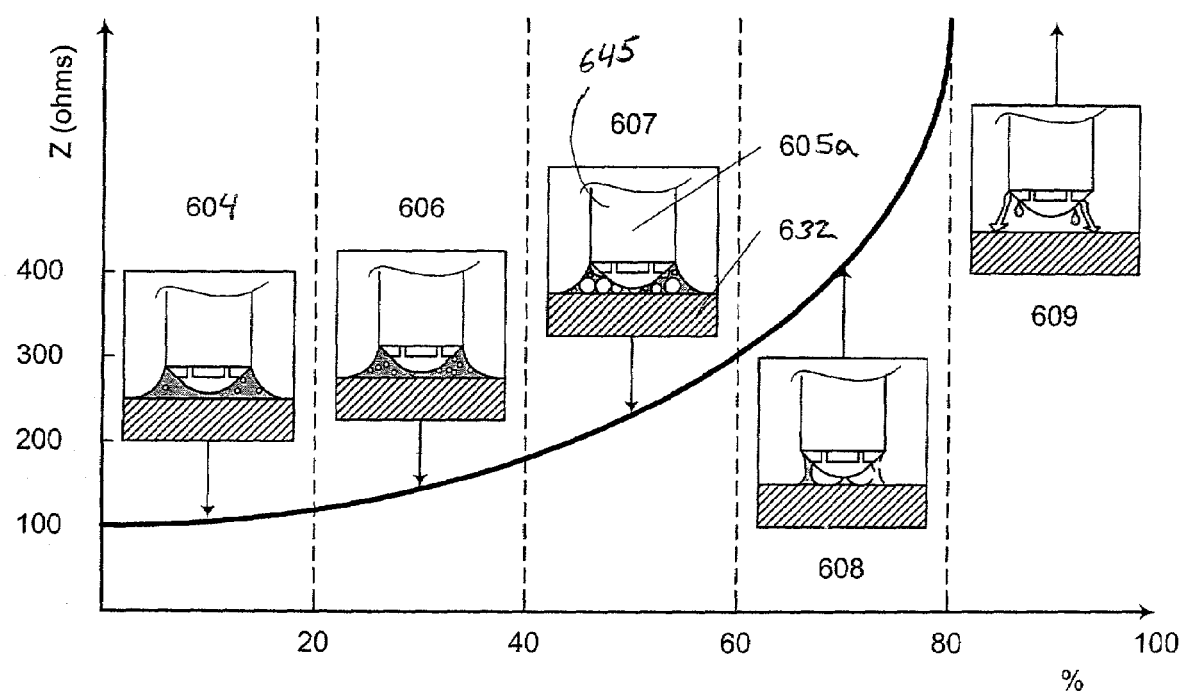
FIG. 29 is a schematic graph of the impedance Z versus boiling of fluid %.

For a monopolar device the presence of various fractions of boiling can be visually estimated by the naked eye, or by detecting changes in electrical impedance. As shown in FIG. 29, the impedance Z may change from a level of about 100 ohms with no boiling, to a level of about 400 ohms or more with a large fraction of the conductive fluid boiling. The percentages of boiling shown are exemplary as are the levels of impedance. Also shown in FIG. 29 is the qualitative nature of the boiling as the % boiling increases, indicated by the small figures for each of five exemplary "regimes" of boiling. In each small figure the tip 645 of the device 605a is shown in close proximity to tissue 632. As boiling begins in regime 604, there are few small bubbles of vapor in the conductive fluid, here saline. As the percentage of boiling increases at regime 606 there are a larger number of small bubbles. As the percentage boiling increases further at regime 607, the bubbles become much larger. At even higher percentage boiling at regime 608 intermittent threads of saline form and are quickly boiled off. Finally, at the highest level of regime 609, boiling drops of saline are instantly boiled and arcing occurs from the metal to the tissue.

While the invention insofar has been described in relation to a bipolar electrosurgical device, it will be readily apparent that other electrosurgical devices can be easily adapted to be used in connection with the invention. For example, the electrosurgical device 5 in FIG. 1 can, in another embodiment, be provided as a monopolar device. In this embodiment, one of the wires going to the bipolar device would instead go to a ground pad dispersive electrode located on the patient's back or other suitable anatomical location. Minimally, the electrosurgical device will be capable of delivering RF power and conductive solution to tissue. For example, the device can comprise a straight needle having an interior lumen for transmitting conductive solution to the tissue. Alternatively, the electrosurgical device can comprise other configurations such as loops, forceps, blades, and the like.

Figure 21:
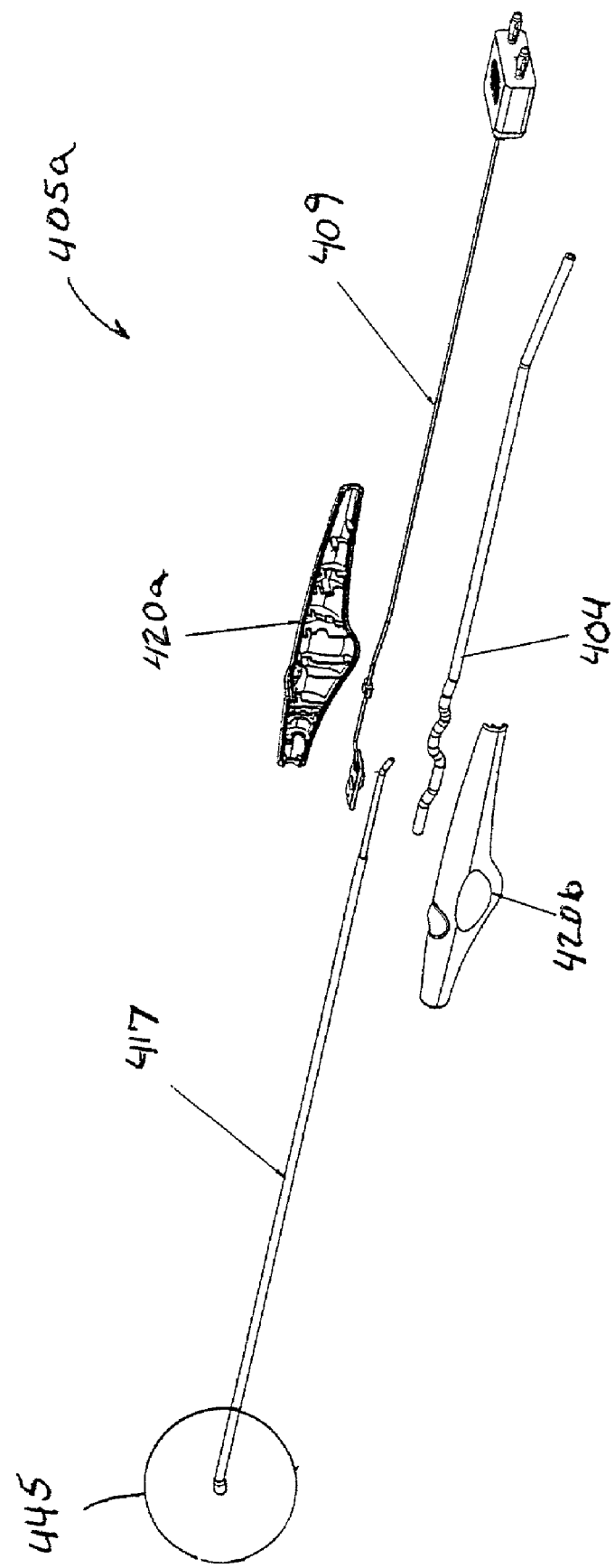
FIG. 21 is a schematic exploded perspective view of one embodiment of a monopolar electrosurgical device.

Referring to FIG. 21, there is shown a perspective view of another electrosurgical device 405a in accordance with another embodiment of the invention. As shown, electrosurgical device 405a comprises a monopolar electrosurgical device. As shown in FIG. 201, electrosurgical device 405a includes a hollow shaft 417, a proximal handle 420a, 420b and a tip 445. As best shown in FIG. 22, tip 445 includes a contact element preferably comprising an electrode 425. In the embodiment shown in FIG. 22, electrode 425 has a generally spherical shape.

Preferably the relationship between the material for electrode 425 and the fluid should be such that the fluid wets the surface of the electrode 425 to form a continuous thin coating thereon and does not form isolated rivulets or beads. Contact angle, θ, is a quantitative measure of the vetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $\gamma_{lv} \cos \theta = \gamma_{sv} - \gamma_{sl}$ where $\gamma_{lv}$, $\gamma_{sv}$, and $\gamma_{sl}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle represents complete wetting.

As shown in FIGS. 22 and 23, electrode 425 is preferably located in a receptacle of a cylindrical sleeve 482 comprising a cavity 481, which guides movement of the electrode 425 and also functions as a housing for retaining the electrode 425. As shown, a portion of the electrode 425 is retained within the cavity 481 while another portion extends distally through the fluid outlet opening 426. Also as shown sleeve 482 is connected, preferably via welding with silver solder, to the distal end 453 of shaft 417. Electrode 425, sleeve 482 and shaft 417 preferably comprise an electrically conductive metal, which is preferably non-corrosive, such as stainless steel or titanium.

When electrode 425 is in the form of a sphere, the sphere may have any suitable diameter. However, the sphere preferably has a diameter of about 1 mm to about 7 mm, and more preferably has a diameter of about 2.5 mm to about 3.5 mm. Even more preferably, the sphere has a diameter of about 3 mm. It is understood that shapes other than a sphere can be used; examples of such shapes include oblong or elongated shapes.

As for cavity 481, the internal diameter of cavity 481 surrounding the sphere has a diameter slightly larger than the diameter of the sphere, typically about 0.25 mm. This permits the sphere to freely rotate within the cavity 481. Consequently, cavity 481 of sleeve 482 also preferably has a diameter in the range between an including about 1 mm to about 7 mm.

Similar to the electrodes of the bipolar electrosurgical devices discussed above, electrode 425 may also comprise any of the porous materials (e.g. metal, polymer or ceramic). In this embodiment, similar to the other porous electrode embodiments, the porous structure of electrode 425 allows fluid to not only pass around electrode 425 to be expelled, but also allows fluid to pass through the electrode 425 to be expelled.

In order to retain the electrode 425 within the cavity 481 of sleeve 482, preferably the hole 426, which ultimately provided a fluid outlet opening, of cavity 481 at its distal end 483 comprises a distal pinched region 486 which is reduced to a size smaller than the diameter of the electrode 425 to inhibit escape of the electrode 425 from the sleeve 482. More preferably, the hole 426 comprises a diameter smaller than the diameter of the electrode 425. Hole 426 is preferably made to have a diameter smaller than the diameter of the electrode 425 by at least one crimp 484 located at the distal end 483 of the sleeve 482 which is directed towards the interior of the sleeve 482 and distal to the portion of the electrode 425 confined in cavity 481. Where one crimp 484 is employed, the crimp may comprise a single continuous circular rim pattern. In this manner, the contact element portion extending distally through the fluid outlet opening has a complementary shape to the fluid outlet opening, here both circular.

However, the crimp 484 may also comprise a discontinuous circular rim pattern where the crimp 484 is interrupted by at least one rectangular hole slot 485 formed at the distal end 483 of the sleeve 482. Thus, the fluid outlet opening may comprise a first portion (e.g. the circular portion) and a second portion (e.g. the slot). As shown in FIG. 24, preferably, crimp 484 comprises at least four crimp sections forming a circular rim pattern separated by four discrete slots 485 radially located there between at 90 degrees relative to one another and equally positioned around the fluid outlet opening first portion. Slots 485 are preferably used to provide a fluid outlet opening or exit adjacent the electrode 425 when the electrode 425 is fully seated (as discussed below) and when the electrode 425 is not in use (i.e. not electrically charged) to keep the electrode surface wet. Preferably, slots 485 have a width in the range between and including about 0.1 mm to 1.0 mm, and more preferably have a width in the range of 0.2 mm to 0.3 mm, As for length, slots 485 preferably have a length in the range between and including 0.1 mm to 1.0 mm, and more preferably have a length in the range of 0.4 mm to 0.6 mm.

As shown in FIG. 24, the contact element portion extending distally through the fluid outlet opening 426 extends distally through the fluid outlet opening first portion (e.g. the circular portion) and does not extend distally through the fluid outlet opening second portion (e.g. the slot). In this manner an edge of the slot remains exposed to tissue to provide a tissue separating edge as discussed below.

It should be understood that the particular geometry of fluid exit to the electrode is not critical to the invention, and all that is required is the presence of a fluid exit which provides fluid as required. For example, hole 426 may comprise an oval shape while electrode 425 comprises a round shape.

In addition to slot 485 providing a fluid exit, at least one edge 491 of slot 485 may provide a tissue separating edge adjacent a blunt surface which may be used for blunt dissection when the electrosurgical device 405a is manipulated, particularly by twirling or impacting. When edge 491 is used in such regard, it is preferred that the edge comprise a sharp edge with a sharp angle which has not been rounded by, for example, a fillet.

Turning to the proximal end of the electrode 426, preferably the portion of the sleeve proximal to the electrode 426 also has a proximal pinched region 487 which retains the electrode 426 in the sleeve and inhibits escape of the electrode 425 from the sleeve 482, such as a diameter smaller than the diameter of the electrode 425.

While distal pinched region 486 and proximal pinched region 487 may be used solely to support the electrode 425 in its position of use, the electrode may be further supported by a compression spring 488 as shown in FIG. 21. The use of spring 488 is preferred to provide a variable length support within the working length of the spring 488 for overcoming manufacturing tolerances (e.g. length) between the fixed supports (i.e. pinched regions 486 and 487) of the sleeve 482. As for maintaining proper location of the spring 488, sleeve 482 also comprises a lumen 489 (i.e. the cavity of an elongated hollow structure, such as a tube or tube like structure; typically cylindrical) which, in addition to providing a direct passage for fluid, provides a guide tube for spring 488. Furthermore, the surface portion of the electrode 425 which contacts the spring 488 may comprise a flat surface rather than a curvilinear surface to better seat the spring against the electrode 425.

In addition to the above, spring 488 provides a multitude of functions and advantages. For example, spring 488 offers the ability to move electrode 425 distally and proximally within sleeve 482. As shown in FIG. 21, spring 488 is located proximal to the electrode 425 between a first load bearing surface comprising the electrode surface and a second load bearing surface comprising the distal end 453 of shaft 417. In this manner, spring 488 can be configured to provide a decompression force to seat the electrode 425 against the distal pinched region 486, in this case the perimeter edge of crimp 484, prior to use of the electrosurgical device 405a. Conversely, upon application of the electrode 425 of the device 405a against tissue with sufficient force to overcome the compression force of the spring 488, spring 488 compresses and the electrode 425 retracts proximally away from distal pinched region 486, in this case perimeter edge 492 of crimp 484, changing the position thereof. In the above manner, the contact element comprising electrode 425 is retractable into the cavity 481 of the housing upon the application of a proximally directed force against the portion of the electrode extending distally beyond the distal opening located at the distal end of the housing and spring 488 functions as a retraction biasing member.

By making the electrode 425 positionable in the above manner via spring 488, in various embodiments the electrosurgical device 405a can be provided with a damper mechanism which dampens the force of the electrode 425 on tissue being treated.

Furthermore, in various embodiments the electrosurgical device 405a, an electrode 425 which can be positioned as outlined above can comprise a fluid flow rate adjustment mechanism which incrementally increases the area of the hole 426 and the corresponding fluid flow rate in response to the incremental proximal retraction of the electrode 425. In such an instance the electrode 425 functions as a valve in regulating flow of the fluid through hole 426.

In various embodiments, spring 488 may be used in conjunction with the distal pinched region 486 (e.g. crimp 484 comprising a single continuous circular pattern) to provide a fluid seal between the electrode 425 and the distal pinched region 486 which stops fluid flow from the electrosurgical device 405a. In this manner, the electrosurgical 405a device may be used to provide both a wet electrode and dry electrode (i.e. when the fluid flow is on and off, respectively) with the energy and fluid provided sequentially in addition to simultaneously. The incorporation of a dry electrode function into the device of the current invention may be desirable to provide a mechanism for electrosurgical cutting.

Furthermore, in various embodiments of electrosurgical device 405a, an electrode 425 which can be positioned as outlined above can comprise a declogging mechanism which retracts to provide access for unclogging fluid exit holes, such as fluid exit holes 426 and 485, which may become flow restricted as a result of loose debris (e.g. tissue, blood) becoming lodged therein. For example, when a biasing force, such as from a handheld cleaning device (e.g. brush) or from pushing the tip against a hard surface such as a retractor, is applied to electrode 425 which overcomes the compression force of the spring 488 causing the spring 488 to compress and the electrode 425 to retract, the tip of the handheld cleaning device may by extended into the hole 426 for cleaning the hole 426 and perimeter edge 492. Stated another way, an electrode 425, which can be positioned as outlined, provides a method declogging hole by increasing the cross-sectional area of the fluid exit to provide access thereto.

Also, in various embodiments the electrosurgical device 405a the spring 488 comprises an electrical conductor, particularly when the electrode 425 is retracted to a non-contact position (i.e. not in contact with) the sleeve 482.

In other embodiments, proximal pinched region 487 may comprise one or more crimps similar to distal pinched region 486, such that electrode 425 is retained in sleeve 482 both distally and proximally by crimps. Also, in other embodiments, sleeve 482 may be disposed within shaft 417 rather than being connected to the distal end 453 of shaft 417. Also, in still other embodiments, sleeve 482 may be formed unitarily (i.e. as a single piece or unit) with shaft 417 as a unitary piece.

As best shown in FIGS. 22 and 23, the electrode 425 is retained in the sleeve 482 such that a portion of the electrode 425 extends distally beyond distal end 483 of the sleeve 482. As shown, preferably the surface of this exposed portion of the electrode 425 is blunt and does not comprise any sharp corners.

The portion of the electrode 425 which extends distally beyond the distal end 483 of the sleeve is controlled by the shape of the hole 426 in sleeve 482 in relation to the shape of the electrode 425. Also an electrical insulator 490 (i.e. non-conductive material) preferably surrounds shaft 417 and sleeve 482 along substantially its entire exposed length (e.g. the portion outside the confines of the handle 420), terminating a short distance (e.g. at the proximal onset of the crimp 484 or less than about 3 mm) from distal end 483 of the sleeve 482.

As with the other electrosurgical devices described within, a fluid line 404 and a power source, preferably comprising generator 406 preferably providing RF power via a cable 409, are preferably fluidly and electrically coupled, respectively, to the electrosurgical device 405a.

As indicated above for a monopolar electrosurgical device, one of the wires going to a bipolar device instead goes to a ground pad dispersive electrode located on the patient's back or other suitable anatomical location. The remaining terminal (e.g., positive) of the generator 406 is electrically coupled to the electrode 425 preferably via a wire conductor from insulated wire cable 409 attached, preferably via silver solder, to the outer surface of the shaft 417 within the confines of the handle 417. Contact between electrode 425, sleeve 482, shaft 417 and spring 488 each comprising electrically conductive metal, for example, provides electrical potential to the electrode 425.

In other embodiments, the shaft 417 may be made of an electrical non-conducting material except for a portion at its distal end that comes in contact with sphere sleeve 482. This portion of shaft 417 that contacts the sleeve 482 should be electrically conducting. In this embodiment, the wire conductor from insulated wire cable 409 extends to this electrically conducting portion of shaft 417. In still other embodiments, the shaft may completely comprises a non-conducting material as where the wire conductor from insulated wire cable 409 extends directly to the sleeve 482.

With respect to the fluid coupling, similar to above, fluid from the fluid source 401 for use with electrosurgical device 405a preferably is communicated from fluid source 401 through a flexible, polyvinylchloride (PVC) outlet fluid line 404 to a flexible, polyvinylchloride (PVC) inlet fluid line connected to the electrosurgical device 405a. The outlet fluid line 404 and the inlet fluid line are preferably connected via a male and female mechanical fastener configuration, preferably comprising a Luer-Lok® connection from Becton, Dickinson and Company. The lumen of the inlet fluid line preferably has an inside diameter of 2 mm. The lumen of the inlet line is then preferably interference fit over the outside diameter of the shaft 417 of about 2.4 mm of to provide a press fit seal there between. Additionally an adhesive may be disposed there between to strengthen the seal. Fluid is then communicated down the lumen of the shaft 417 through the lumen 489 and cavity 481 of the sleeve 482 where it is expelled from around and on the surface of the electrode 425. This provides a wet electrode for performing electrosurgery.

As shown in FIG. 25, during use of the monopolar electrosurgical device 405a, typically a coupling bead 490 of fluid is provided between the tissue 432 and the electrode 425. When the user of electrosurgical device 405a places the electrode 425 at a tissue treatment site and moves the electrode 425 across the tissue, fluid is expelled around and on the surface of the electrode 425 at the distal end 483 of the sleeve 482 and onto the tissue 432. The fluid, in addition to providing an electrical coupling between the electrosurgical device 405a and the tissue 432 when electrically conductive, lubricates the tissue 432 and facilitates the movement of electrode 425 across the tissue 432. During movement of the electrode 425, the electrode 425 typically slides across the tissue 432, but also may rotate as the electrode 425 moves across the tissue 432.

When the electrode 425 is placed directly in contact with tissue 432, it may be possible for the tissue 432 to occlude fluid flow from the holes 426 and 485. Thus, in yet another embodiment of the invention as shown in FIGS. 26A, 26B, fluid exit holes may be located in the cylindrical side of the sleeve 582, either proximal or adjacent to the electrode 525 and either in addition to or as an alternative to fluid exit holes 526 and 585. As shown in FIGS. 26A–B, at least one fluid exit hole 593 is formed in the cylindrical longitudinal side surface and wall of the sleeve 582 adjacent to electrode 525 when electrode 525 is fully seated, while at least one fluid exit hole 594 is formed in the cylindrical side of the sleeve 582 proximal to electrode 525 when electrode 525 is fully seated. Alternatively, holes may be provided in sleeve 582 by porous materials as already discussed herein. In the above manner, the tip portion 545 comprises a first tissue treating surface (e.g. distal end) and a second tissue treating surface (e.g. side surface). As discussed above, preferably the first tissue treating surface is configured for blunt dissection while the second tissue treating surface is configured for coagulation.

Preferably, holes 593 and 594 each comprise more than one hole which are equally spaced radially in a circular pattern around the longitudinal axis of the tip 545, and more particularly sleeve 582. More preferably, holes 593 and 594 each comprise four discrete holes equally spaced 90 degrees around the cylindrical side of the sleeve 582. Preferably holes 593, 594 have a diameter in the range between and including 0.1 mm to 1.0 mm, and more preferably have a length in the range of 0.20 mm to 0.6 mm. Also preferably, as shown, each set of holes 593 and 594 are radially offset from one another, and more preferably offset 45 degrees to better disperse fluid over the entire surface of the electrode.

An electrode 525 which can be positioned as outlined above can comprise not only a valve for regulating fluid flow from the fluid exit holes, but also comprise a valve which while opening one fluid flow exit simultaneously closes another fluid flow exit. For example, as electrode 525 retracts proximally, fluid exit hole 526 is opened while fluid exit hole 593 is closed. Stated another way, an electrode 525 which can be positioned as outlined above can provide a mechanism for altering the size and/or location of the fluid exit holes during use of the electrosurgical device 505a which may be necessary, for example, to direct fluid to a particular tissue location or balance fluid flow among the fluid exit outlets.

In FIGS. 26A, 26B the cylindrical part of the sleeve 582, the crimp 584 that retains the sphere in cavity 581, and the sphere 525 are all active electrode surfaces and can provide electrical energy to tissue. This combined electrode surface can be wet by fluid flow from holes 594 or 593, as well as from the slots 585 in the crimp 584 adjacent the sphere 525. The effects of gravity and surface tension tend to wick the fluid, here saline, around the circumference of the cylindrical sleeve 582 to preferably cover the entire active electrode surface. It is not necessary that saline is present between the metal electrode surface and tissue at all points of tissue contact, since the convective cooling of the metal electrode by flowing saline is often sufficient to keep the metal electrode and tissue contacting the metal electrode at or below a temperature of 100° C.

In this embodiment electrical insulator 590 preferably terminates proximally to both holes 593 and 594 as well as sleeve 582 where sleeve 582 is connected to the distal end 553 of shaft 517. In certain instances where the sleeve is formed unitary with the shaft 517, the electrical insulator 590 preferably terminates proximally to proximal pinched region 587. In this manner, the electrode 525 now comprises both a sphere portion and a cylindrical portion, with the cylindrical portion substantially increasing the surface area of the electrode 525. As a result, the electrode now also comprises surfaces which are parallel and perpendicular to the longitudinal axis of the tip 545, and more particularly sleeve 582, of the electrosurgical device 505a.

The electrode configuration shown in FIGS. 26A, 26B is particularly useful to a surgeon performing a liver resection. Once the outer capsule of the liver is scored with a bovie blade along the planned line of resection the tip 545 is painted back and forth along the line, resulting in coagulation of the liver parenchyma. As the tissue is coagulated under and around the electrode surfaces, the electrode 525 is used to blunt dissect into the coagulated parenchyma, with the sharper slots 585 around the crimp 584 providing roughness elements that aid in disrupting the tissue and enabling the parting of the tissue.

Figure 27:
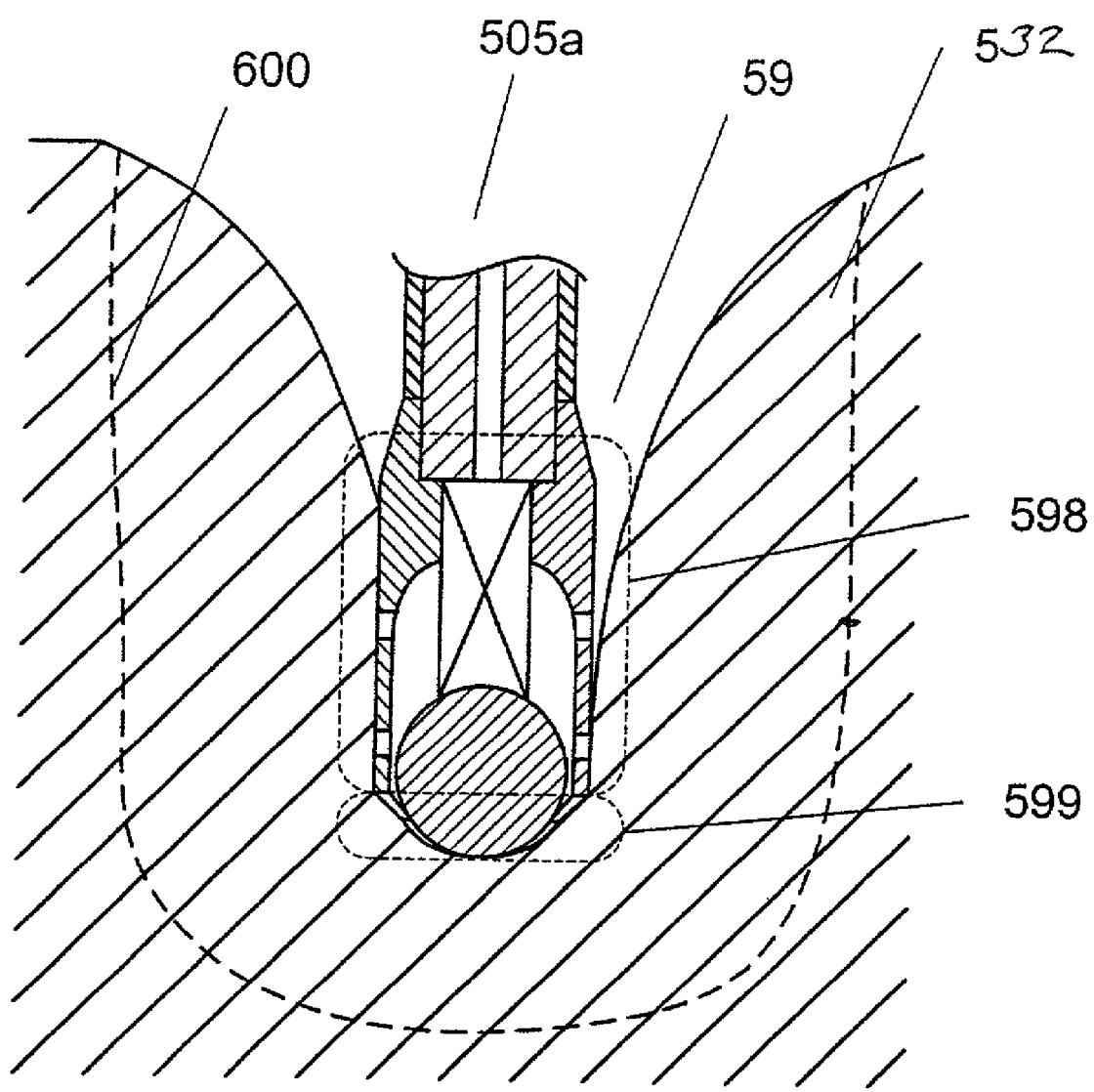
FIG. 27 is a schematic close-up view of the alternative tip of FIG. 26A disposed in a tissue crevice.

As shown in FIG. 27, the device 505a can be used deeply in a crevice 597 of tissue 532 to blunt dissect the tissue and coagulate it at the same time. Blunt dissection is preferred over sharp dissection, such as with a blade or scissors, since blunt dissection is less likely to tear or damage the larger blood vessels or other vessels. Once identified by blunt dissection, larger vessels can be safely clipped, tied with suture or sealed with some other device. If the larger vessels are not thus first "skeletonized" without being damaged by blunt dissection, they may bleed profusely and require much more time to stop the bleeding. The device can also be used to coagulate first without simultaneous blunt dissection, and then blunt dissect in a separate step.

This technique can also be used on other parenchymal organs such as the pancreas, the kidney, and the lung. In addition, it may also be useful on muscle tissue and subcutaneous fat. It's use can also extend to benign tumors, cysts or other tissue masses found in the urological or gynecological areas. It would also enable the removal of highly vascularized tumors such as hemangiomas.

Thus, the holes 594 and 593 in the cylindrical sleeve 582 of the overall electrode surface are intended to assure that saline is provided to the smooth, less rough, atraumatic sides of the electrode that are used to produce tissue coagulation and hemostasis rather than blunt dissection. The most distal portion of the device may have a more rough, but also wetted, electrode surface that can blunt dissect as well as coagulate tissue.

In FIG. 27 the zone 599 identifies the part of the electrode that has the ability to blunt dissect and coagulate, and the zone 598 identifies the part that is intended primarily for coagulation. The line 600 indicates the depth of the zone of tissue that is coagulated, typically from 3 mm to 5 mm deep.

Figure 30:
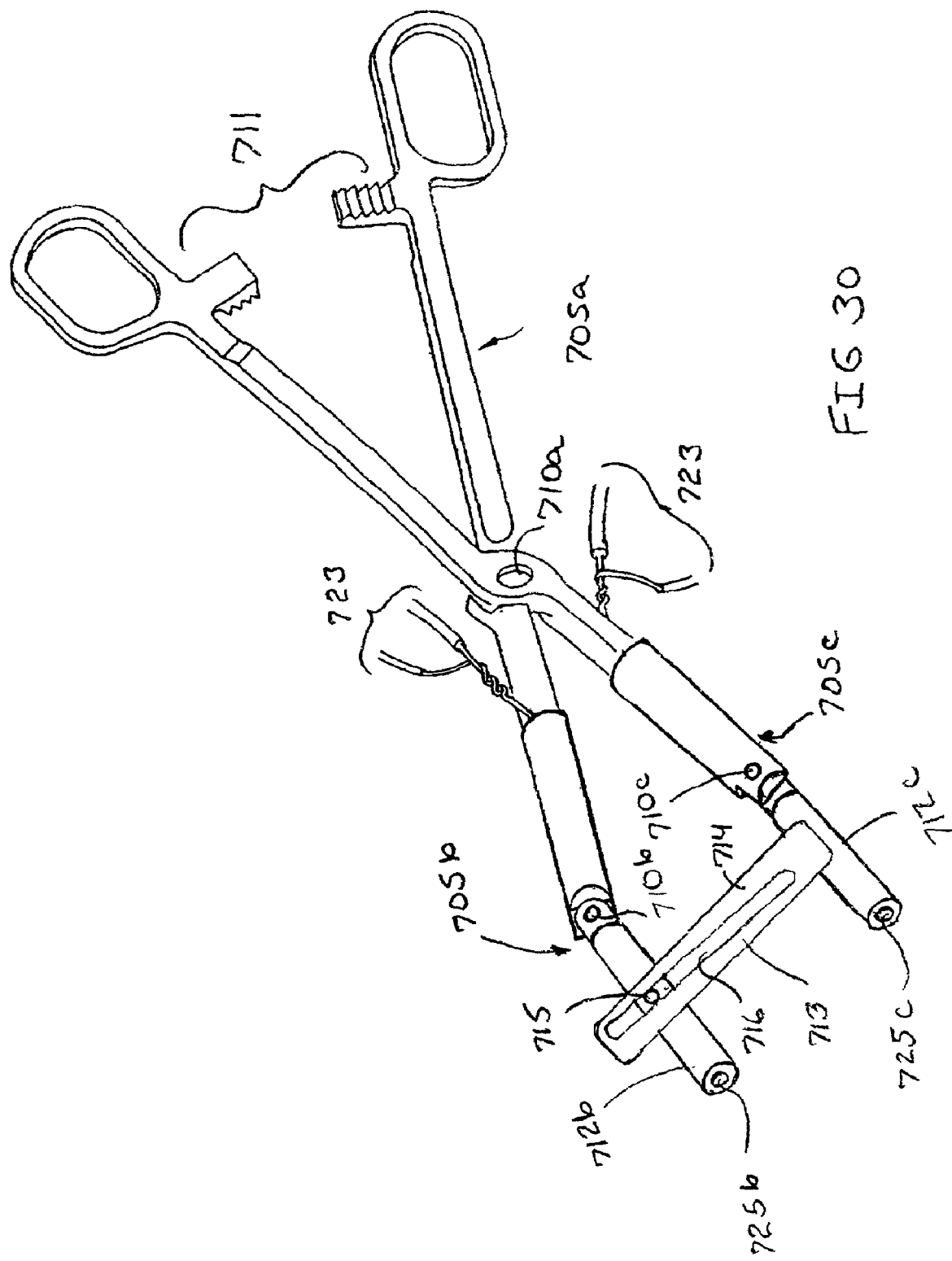
FIG. 30 is a schematic side view schematic side view of another embodiment of an electrosurgical device.

In other embodiments, exemplary surgical devices such as forceps 705a may also comprise tissue treatment portions 705b, 705c as shown at in FIG. 30 which are configured similar to 405a and 505a. Preferably the tissue treatment portions 705b, 705c each comprise contact elements 725b, 725c of different poles (positive and negative) such that the device 705a functions as a bipolar device. A bipolar device of this type is particularly useful as a surface coagulator and not as a coaptive device since the device 705a does not grasp tissue. Due to its configuration, device 705a provides a very narrowly defined but intense tissue effect with current directed between the two poles in the case of a bipolar device. The tissue effect is related to the contact element size and separation between the elements and therefore it is desirable to make the separation of the two contact elements adjustable relative to one another. As shown, the opening apart and closing together of the two tissue treatment portions 705b, 705c may be provided by a pivot 710a. Device 705a may also comprise a latching mechanism 711 which fixes the position of the elements 725b, 725a relative to one another during tissue treatment. Device 705a is particularly useful for straddling blood vessels located between the elements 725b, 725c and their subsequent sealing. Tissue treatment portions 705b and 705c also preferably comprise pivots 710b and 710c and pivot portions 712b and 712c. Pivot portions 712b and 712c are preferably connected by a linkage 713 which permits adjustment of the separation or displacement distance between pivot portions 712b and 712c. Furthermore, linkage 713 also preferably keeps pivot portions 712b, 712c parallel to one another with use of the device 705a. A shown, linkage 713 comprises a bar 714 fixed to pivot portion 712c and having an elongated opening 716 therein. Linkage also comprises a pin 715 fixed to pivot portion 712b which moves along the opening 716 during use of the device 705a with open and closure of the pivot portions 712b, 712c relative to one another.

Other suitable electrosurgical devices that can be used in connection with the invention described herein include, but are not limited to, devices described in U.S. patent application Ser. No. 09/668,403 (filed 22 Sep. 2000), U.S. Pat. No. 5,897,553 entitled "Ball Point Fluid-Assisted Electrocautery Device to Mulier et al., U.S. Pat. No. 6,063,081 entitled "Fluid-Assisted Electrocautery Device to Mulier et al., and U.S. Pat. No. 6,096,037 entitled "Tissue Sealing Electrosurgery Device and Methods of Sealing Tissue to Mulier et al.

Moreover, it will be readily apparent that other means can be used to provide heat to the tissue, in addition to the radio frequency power described herein.

One or more of the features of the previously described system can be built into a custom RF generator. This embodiment can provide one or more advantages. For example, this type of system can save space and reduce overall complexity for the user. This system can also enable the manufacturer to increase the power delivered into low impedance loads, thereby further reducing the time to achieve the desired tissue effects. This changes the curve of FIG. 5, by eliminating or reducing the slope of the low impedance ramp 48 of power versus impedance.

To effectively treat thick tissues, it can be advantageous to have the ability to pulse the RF power on and off. Under some circumstances, the temperature deep in tissue can rise quickly past the 100° C. desiccation point even though the electrode/tissue interface is boiling at 100° C. This manifests itself as "popping," as steam generated deep in the tissue boils too fast and erupts toward the surface. In one embodiment of the invention, a switch is provided on the control device or custom generator to allow the user to select a "pulse" mode of the RF power. Preferably, the RF power system in this embodiment is further controlled by software.

In some embodiments, it can be desirable to control the temperature of the conductive fluid before it is released from the electrosurgical device. In one embodiment, a heat exchanger is provided for the outgoing saline flow to either heat or chill the saline. The heat exchanger may be provided as part of the electrosurgical device or as part of another part of the system, such as within the enclosure 14. Pre-heating the saline to a predetermined level below boiling reduces the transient warm-up time of the device as RF is initially turned on, thereby reducing the time to cause coagulation of tissue. Alternatively, pre-chilling the saline is useful when the surgeon desires to protect certain tissues at the electrode/tissue interface and treat only deeper tissue. One exemplary application of this embodiment is the treatment of varicose veins, where it is desirable to avoid thermal damage to the surface of the skin. At the same time, treatment is provided to shrink underlying blood vessels using thermal coagulation. The temperature of the conductive fluid prior to release from the surgical device can therefore be controlled, to provide the desired treatment effect.

In another embodiment, the flow rate controller is modified to provide for a saline flow rate that results in greater than 100% boiling at the tissue treatment site. For example, the selection switch 12 of the flow rate controller 11 (shown in FIG. 1) can include settings that correspond to 110%, 120% and greater percentages of boiling. These higher settings can be of value to a surgeon in such situations as when encountering thick tissue, wherein the thickness of the tissue can increase conduction away from the electrode jaws. Since the basic control strategy neglects heat conduction, setting for 100% boiling can result in 80% of 90% boiling, depending upon the amount of conduction. Given the teachings herein, the switch of the flow rate controller can accommodate any desirable flow rate settings, to achieve the desired saline boiling at the tissue treatment site.

Some embodiments of the invention can provide one or more advantages over current electrosurgical techniques and devices. For example, the invention preferably achieves the desired tissue effect (for example, coagulation, cutting, and the like) in a fast manner. In a preferred embodiment, by actively controlling the flow rate of saline, both in quantity (Q vs. P) and location (for example, using gutters to direct fluid distally to tissue, using holes to direct flow of fluid, or other similar methods) the electrosurgical device can create a hot non-desiccating electrode/tissue interface and thus a fast thermally induced tissue coagulation effect.

The use of the disclosed devices can result in significantly lower blood loss during surgical procedures such as liver resections. Typical blood loss for a right hepatectomy can be in the range of 500–1,000 cubic centimeters. Use of the devices disclosed herein to perform pre-transection coagulation of the liver can result in blood loss in the range of 50–300 cubic centimeters. Such a reduction in blood loss can reduce or eliminate the need for blood transfusions, and thus the cost and negative clinical consequences associated with blood transfusions, such as prolonged hospitalization and a greater likelihood of cancer recurrence. Use of the device can also provide improved sealing of bile ducts, and reduce the incidence of post-operative bile leakage, which is considered a major surgical complication.

The use of the devices as disclosed herein can result in a lower frequency of post-operative air leaks after lung resection, compared with linear staplers. This reduction in air leaks can reduce the length of hospitalization and the length of time that a chest tube must remain in place. The use of the devices disclosed herein can also reduce the frequency of expectorated staples (staples coughed up by the patient), since no foreign body is needed to seal lung tissue against air leaks and blood loss. The use of the devices disclosed herein can also speed up and simplify the histopathological examination of lung tissue removed for biopsy as part of a wedge resection, since the pathologist does not have to carefully remove dozens of small staples from the tissue sample.

The invention can, in some embodiments, deliver fast treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

In another aspect, the invention preferably provides an electrosurgical device design that is capable of quickly and effectively sealing a wide variety of tissue segment sizes. The electrosurgical device provides a number of characteristics that improve the ability to treat a wide variety of tissue size and thickness. For example, a preferred embodiment provides the ability to control the saline flow towards a high percentage boiling, for example, 80–100%. This reduces shunting of the RF by boiling off saline before it could flow to the other electrode, or by boiling the saline as it is in the process of flowing to the other electrode. In another aspect, one preferred embodiment includes gutters in connection with the electrodes. In this embodiment, saline flow is directed toward the tissue treatment site, thereby providing all or substantially all of the conductive fluid to the treatment site. Thus, the tissue being treated is sufficiently "protected" from desiccation by utilizing the controlled conductive fluid boiling described herein. Preferably, the tissue-activated jaws offer another way to provide the conductive fluid in proximity to where the RF power is turned into heat.

For purposes of the appended claims, the term "manipulate" includes, but is not limited to, the functions of grasping, holding, fixing, cutting, dissecting, exposing, removing, extracting, retrieving, coagulating, ablating and otherwise manipulating or similarly treating tissue. Also for purposes of the appended claims, the term "tissue" includes, but is not limited to, organs (e.g. liver, lung, spleen, gallbladder), highly vascular tissues (e.g. liver, spleen), soft and hard tissues (e.g. adipose, areolar, bone, bronchus-associated lymphoid, cancellous, chondroid, chordal, chromaffin, cicatricial, connective, elastic, embryonic, endothelial, epithelial, erectile, fatty, fibrous, gelatiginous, glandular, granulation, homologous, indifferent, interstitial, lymphadenoid, lymphoid, mesenchymal, mucosa-associated lymphoid, mucous, muscular, myeloid, nerve, osseous, reticular, scar, sclerous, skeletal, splenic, subcutaneous), tissue masses (e.g. tumors), etc.

Although the above description is given with respect to specific bipolar and monopolar devices disclosed herein, it should be readily appreciated that devices according to the present invention may be constructed and arranged to grasp, hold, fix, cut, dissect, expose, remove, extract, retrieve, and otherwise manipulate and treat organs, tissues, tissue masses, and objects.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes.

We claim:

1. A method for treating tissue comprising:
providing a monopolar electrosurgical device;
providing radio frequency power and an electrically conductive fluid to the electrosurgical device;
providing the electrically conductive fluid from the electrosurgical device at a fluid flow rate;
forming a localized fluid coupling with the electrically conductive fluid which couples the tissue and the electrosurgical device, the fluid coupling localized at a tip portion of the electrosurgical device;
providing the radio frequency power from the electrosurgical device at a power level;
applying the radio frequency power to the tissue, at least a portion of the radio frequency power applied through the fluid coupling to the tissue;
heating the tissue with the radio frequency power;
heating the fluid coupling with heat from the tissue sufficient to cause a boiling of the fluid coupling; and
using the boiling of the fluid coupling as a visual indicator of a temperature of the tissue.

2. The method according to claim 1 wherein:
the step of using the boiling of the fluid coupling as a visual indicator of a temperature of the tissue further comprises using the boiling of the fluid coupling as a visual indicator of a temperature of the tissue being at about a boiling temperature of the conductive fluid.

3. The method according to claim 1 wherein:
the step of using the boiling of the fluid coupling as a visual indicator of a temperature of the tissue further comprises at least one of using an increase and a decrease of the boiling of the fluid coupling as a visual indicator of a temperature of the tissue.

4. The method according to claim 1 wherein:
the step of using the boiling of the fluid coupling as a visual indicator of a temperature of the tissue further comprises using an amount of boiling of the fluid coupling as a visual indicator of a temperature of the tissue.

5. The method according to claim 1 wherein:
the step of using the boiling of the fluid coupling as a visual indicator of a temperature of the tissue further comprises using an onset of boiling of the fluid coupling as a visual indicator of a temperature of the tissue.

6. The method according to claim 1 wherein:
the step of using the boiling of the fluid coupling as a visual indicator of a temperature of the tissue further comprises using the boiling of the fluid coupling as a visual indicator of a temperature of the tissue being at about 100° C.

7. The method according to claim 1 wherein:
the tissue further comprises a tissue surface;
the electrosurgical device further comprises an electrode, the electrode having an electrode surface, the electrode surface comprising a spherical surface forming a distal end surface of the device;
the localized fluid coupling couples the tissue surface and the electrode; and
the step of heating the tissue with the radio frequency power further comprises heating the tissue with the radio frequency power while moving the electrode spherical surface along the tissue surface.

8. The method according to claim 1 wherein:
the tissue comprises at least one blood vessel; and
the step of heating the tissue with the radio frequency power further comprises heating the tissue with the radio frequency power sufficiently to shrink the blood vessel.

9. The method according to claim 1 wherein:
the tissue comprises collagen; and
the step of heating the tissue with the radio frequency power further comprises heating the tissue with the radio frequency power sufficiently to shrink the collagen.

10. The method according to claim 1 wherein:
the tissue comprises a tissue surface; and
using the boiling of the fluid coupling to control a temperature of the tissue surface.

11. The method according to claim 10 wherein:
the step of using the boiling of the fluid coupling to control a temperature of the tissue surface further comprises using the boiling of the fluid coupling to control a temperature of the tissue surface to about a boiling temperature of the conductive fluid.

12. The method according to claim 10 wherein:
the step of-using the boiling of the fluid coupling to control a temperature of the tissue surface further comprises at least one of using an increase and a decrease of the boiling of the fluid coupling to control a temperature of the tissue surface.

13. The method according to claim 10 wherein:
the step of using the boiling of the fluid coupling to control a temperature of the tissue surface further comprises using an amount of boiling of the fluid coupling to control a temperature of the tissue surface.

14. The method according to claim 10 wherein:
the step of using the boiling of the fluid coupling to control a temperature of the tissue surface further comprises using an onset of boiling of the fluid coupling to control a temperature of the tissue surface.

15. The method according to claim 1 wherein:
the monopolar electrosurgical device has a proximal end and a distal end and comprises:
a handle;
a tip portion provided at an ending of a shaft extending from the handle, the shaft supporting the tip portion in rigid relation to the handle;
the tip portion comprising an electrode and at least one fluid outlet opening;
a fluid passage; and
the at least one fluid outlet opening in fluid communication with the fluid passage.

16. The method according to claim 15 wherein:
the distal end of the monopolar electrosurgical device comprises a blunt distal end.

17. The method according to claim 16 wherein:
the blunt distal end of the monopolar electrosurgical device is provided by a spherically shaped portion of the electrode.

18. The method according to claim 17 wherein:
the electrode of the monopolar electrosurgical device comprises a cylindrically shaped portion proximal to the spherically shaped portion.

19. The method according to claim 17 wherein:
the at least one fluid outlet opening of the monopolar electrosurgical device is proximal to the spherically shaped portion of the electrode.

20. The method according to claim 15 wherein:
the shaft of the monopolar electrosurgical device comprises a rigid hollow shaft; and
a portion of the fluid passage of the monopolar electrosurgical device is contained within the shaft.

21. The method according to claim 15 wherein:
the at least one fluid outlet opening is at least partially defined by the electrode.

22. The method according to claim 1 wherein:
the tissue comprises at least one of soft tissue and vascular tissue.

23. The method according to claim 1 wherein:
the tissue comprises tumor tissue.

24. The method according to claim 1 wherein:
the tissue comprises at least one of hard tissue, bone tissue and cancellous tissue.

25. The method according to claim 1 wherein:
the tissue comprises at least one of organ tissue, liver tissue, lung tissue, spleen tissue, gallbladder tissue, kidney tissue and pancreas tissue.

26. The method according to claim 1 wherein:
the electrically conductive fluid comprises at least one of saline solution and electrolyte solution.

27. A method for treating tissue, the method comprising:
providing a monopolar electrosurgical device;
providing radio frequency power and an electrically conductive fluid to the electrosurgical device;
providing the electrically conductive fluid from the electrosurgical device at a fluid flow rate;
forming a localized fluid coupling with the electrically conductive fluid which couples the tissue and the electrosurgical device, the fluid coupling localized at a tip portion of the electrosurgical device;
providing the radio frequency power from the electrosurgical device at a power level;
applying the radio frequency power to the tissue, at least a portion of the radio frequency power applied through the fluid coupling to the tissue;
heating the tissue with the radio frequency power;
heating the fluid coupling with heat from the tissue;
visually observing the fluid coupling for a boiling of the fluid coupling; and
adjusting the fluid flaw rate based on visually observing the fluid coupling for a boiling of the fluid coupling.

28. The method according to claim 27 wherein:
the step of adjusting the fluid flow rate based on visually observing the fluid coupling for a boiling of the fluid coupling further comprises decreasing the fluid flow rate based on visually observing a lack of boiling of the fluid coupling.

29. The method according to claim 27 wherein:
the step of adjusting the fluid flow rate based on visually observing the fluid coupling for a boiling of the fluid coupling further comprises increasing the fluid flow rate based on visually observing a boiling of the fluid coupling.

30. The method according to claim 27 wherein:
the step of adjusting the fluid flow rate based on visually observing the fluid coupling for a boiling of the fluid coupling further comprises decreasing the fluid flow rate based on visually observing a boiling of the fluid coupling.

31. The method according to claim 27 wherein:
the tissue comprises at least one blood vessel; and
the step of beating the tissue with the radio frequency power further comprises heating the tissue with the radio frequency power sufficiently to shrink the blood vessel.

32. The method according to claim 27 wherein:
the tissue comprises collagen; and
the step of heating the tissue with the radio frequency power further comprises heating the tissue with the radio frequency power sufficiently to shrink the collagen.

33. The method according to claim 27 wherein:
the monopolar electrosurgical device has a proximal end and a distal end and comprises:
a handle;
a tip portion provided at an ending of a shaft extending from the handle, the shaft supporting the tip portion in rigid relation to the handle;
the tip portion comprising an electrode and at least one fluid outlet opening;
a fluid passage; and
the at least one fluid outlet opening in fluid communication with the fluid passage.

34. The method according to claim 33 wherein:
the distal end of the monopolar electrosurgical device comprises a blunt distal end.

35. The method according to claim 34 wherein:
the blunt distal end of the monopolar electrosurgical device is provided by a spherically shaped portion of the electrode.

36. The method according to claim 35 wherein:
the electrode of the monopolar electrosurgical device comprises a cylindrically shaped portion proximal to the spherically shaped portion.

37. The method according to claim 35 wherein:
the at least one fluid outlet opening of the monopolar electrosurgical device is proximal to the spherically shaped portion of the electrode.

38. The method according to claim 33 wherein:
the shaft of the monopolar electrosurgical device comprises a rigid hollow shaft; and
a portion of the fluid passage of the monopolar electrosurgical device is contained within the shaft.

39. The method according to claim 33 wherein:
the at least one fluid outlet opening is at least partially defined by the electrode.

40. The method according to claim 27 wherein:
the tissue comprises at least one of soft tissue and vascular tissue.

41. The method according to claim 27 wherein:
the tissue comprises tumor tissue.

42. The method according to claim 27 wherein:
the tissue comprises at least one of hard tissue, bone tissue and cancellous tissue.

43. The method according to claim 27 wherein:
the tissue comprises at least one of organ tissue, liver tissue, lung tissue, spleen tissue, gallbladder tissue, kidney tissue and pancreas tissue.

44. The method according to claim 27 wherein:
the electrically conductive fluid comprises at least one of saline solution and electrolyte solution.

45. The method according to claim 27 wherein:

the tissue further comprises a tissue surface;

the electrosurgical device further comprises an electrode, the electrode having an electrode surface, the electrode surface comprising a spherical surface forming a distal end surface of the device;

the localized fluid coupling couples the tissue surface and the electrode; and the step of heating the tissue with the radio frequency power further comprises heating the tissue with the radio frequency power while moving the electrode spherical surface along the tissue surface.

* * * * *

UNITED STATES PATENT AND TRADEMARK OFFICE
CERTIFICATE OF CORRECTION

PATENT NO. : 7,115,139 B2
APPLICATION NO. : 09/947658
DATED : October 3, 2006
INVENTOR(S) : McClurken et al.

It is certified that error appears in the above-identified patent and that said Letters Patent is hereby corrected as shown below:

Title page, item (75) Inventors: "Mark T. Charbonneau, Reading, MA (US)" should read --Mark T. Charbonneau, Portsmouth, NH (US)--

Col. 24, line 1: "or in conduction with" should read --or in conjunction with--

Col. 30, line 50: "jaws 18$a$, 13$b$ are" should read --jaws 18$a$, 18$b$ are--

Col. 39, line 47: "the vetting of" should read --the wetting of--

Col. 44, line 16: "is filly seated," should read --is fully seated,--

Col. 51, line 48, claim 27: "the fluid flaw rate" should read --the fluid flow rate--

Col. 52, line 3, claim 31: "step of beating the" should read --step of heating the--

Signed and Sealed this

Sixteenth Day of January, 2007

JON W. DUDAS
*Director of the United States Patent and Trademark Office*